US010113172B2

(12) United States Patent
Giangrande et al.

(10) Patent No.: US 10,113,172 B2
(45) Date of Patent: *Oct. 30, 2018

(54) NUCLEIC ACID APTAMERS

(71) Applicant: UNIVERSITY OF IOWA RESEARCH FOUNDATION, Iowa City, IA (US)

(72) Inventors: Paloma Giangrande, Iowa City, IA (US); Francis Miller, Iowa City, IA (US); William Thiel, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/489,373

(22) Filed: Apr. 17, 2017

(65) Prior Publication Data
US 2017/0226512 A1 Aug. 10, 2017

Related U.S. Application Data

(62) Division of application No. 14/829,451, filed on Aug. 18, 2015, now Pat. No. 9,624,497, which is a division of application No. 13/964,904, filed on Aug. 12, 2013, now Pat. No. 9,139,835.

(60) Provisional application No. 61/682,055, filed on Aug. 10, 2012, provisional application No. 61/792,723, filed on Mar. 15, 2013.

(51) Int. Cl.
A61L 27/54 (2006.01)
C12N 15/115 (2010.01)
C12N 15/113 (2010.01)
A61L 31/10 (2006.01)
A61L 29/08 (2006.01)
A61L 27/34 (2006.01)
A61L 27/50 (2006.01)
A61K 31/7105 (2006.01)
A61K 47/48 (2006.01)
A61L 31/16 (2006.01)
A61L 29/16 (2006.01)

(52) U.S. Cl.
CPC ........ C12N 15/115 (2013.01); A61K 31/7105 (2013.01); A61K 47/48092 (2013.01); A61L 27/34 (2013.01); A61L 27/507 (2013.01); A61L 27/54 (2013.01); A61L 29/085 (2013.01); A61L 29/16 (2013.01); A61L 31/10 (2013.01); A61L 31/16 (2013.01); C12N 15/1137 (2013.01); A61L 2430/24 (2013.01); C12N 2310/14 (2013.01); C12N 2310/16 (2013.01); C12N 2310/322 (2013.01); C12N 2310/33 (2013.01); C12N 2310/3519 (2013.01); C12N 2320/32 (2013.01); C12N 2330/31 (2013.01); C12Y 106/03001 (2013.01)

(58) Field of Classification Search
CPC .......... A61L 27/54; A61L 31/10; A61L 31/16; C12N 15/115; C12N 15/1137; C12N 2310/16; C12N 2320/32
USPC ............... 435/6.1, 91.1, 91.31, 455; 514/44; 536/23.1, 24.5
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,800,159 | A | 1/1989 | Mullis et al. |
| 4,965,188 | A | 10/1990 | Mullis et al. |
| 9,139,835 | B2 | 9/2015 | Giangrande |
| 9,163,242 | B2* | 10/2015 | Giangrande ....... C12N 15/1135 |
| 9,624,497 | B2 | 4/2017 | Giangrande et al. |

FOREIGN PATENT DOCUMENTS

| WO | 2007143086 A2 | 12/2007 |
| WO | 2010019446 A1 | 2/2010 |
| WO | WO 2011/142970 | * 11/2011 |

OTHER PUBLICATIONS

Rockey, et al., "Synthesis and radiolabeling of chelator-RNA aptamer bioconjugates with copper-64 for targeted molecular imaging", Bioorganic & Medicinal Chemistry 19, 4080-4090 (2011).
Ruckman, et al., "2'-Fluoropyrimidine RNA-based Aptamers to the 165-Amino Acid Form of Vascular Endothelial Growth Factor (VEGF165)", Journal of Biological Chemistry 273 (32), 20556-20567 (1998).
Rusconi, et al., "RNA aptamers as reversible antagonists of coagulation factor IXa", Nature 419, 90-94 (2002).
Schutze, et al., "A calibrated diversity assay for nucleic acid libraries using DiStRO—a Diversity Standard of Random Oligonucleotides", Nucleic Acids Res 38 (4), e23, 5 pages (2010).
Schutze, et al., "Probing the SELEX Process with Next-Generation Sequencing", PLoS One 6 (12), e29604, 10 pages (2011).
Sefah, et al., "Molecular recognition of acute myeloid leukemia using aptamers", Leukemia 23, 235-244 (2009).
Shaman, et al., "Complex Target SELEX", Accounts of Chemical Research 41 (1), 130-138 (2008).
Shangguan, et al., "Identification of liver cancer-specific aptamers using whole live cells", Anal Chem 80, 721-728 (2008).
Sousa, et al., "A mutant T7 RNA polymerase as a DNA polymerase", EMBO J 14, 4609-4621 (1995).
Thiel, et al., "Aptamer-siRNA Chimera Inhibitors of Intimal Hyperplasia", American Society of Gene & Cell Therapy 15th Annual Meeting, Abstract No. 350727, 2 pages (2012).
Thiel, et al., "Delivery of chemo-sensitizing siRNAs to HER2+ breast cancer cells using RNA aptamers", Nucl Acids Res. vol. 40 (13), 6319-6337 (2012).
Thiel, et al., "Nucleotide bias observed with a short SELEX RNA aptamer library", Nucleic Acid Ther 21, 253-263 (2011).

(Continued)

Primary Examiner — Jane J Zara
(74) Attorney, Agent, or Firm — Viksnins Harris Padys Malen LLP

(57) ABSTRACT

The present invention relates to optimized aptamers and methods of using these aptamers.

16 Claims, 109 Drawing Sheets
Specification includes a Sequence Listing.

(56) References Cited

OTHER PUBLICATIONS

Thiel, et al., "Rapid Identification of Cell-Specific, Internalizing RNA Aptamers with Bioinformatics Analyses of a Cell-Based Aptamer Selction", Plos One, 7(9), e43836 (2012).
Thiel, "RNA Inhibitors of Intimal Hyperlasia", American Society of Gene & Cell Therapy 14th Annual Meeting, Abstract No. 350574, 2 pages (2011).
Thiel, et al., "Therapeutic Applications of DNA and RNA Aptamers", Oligonucleotides 19, 209-222 (2009).
Thiel, et al., "VSMC-Targeted Aptamer-siRNA Chimeras as Inhibitors of Intimal Hperplasia", American Heart Association, Scientific Sessions, Abstract, 1 page (2012).
Thies, et al., "Discriminatory aptamer reveals serum response element transcription regulated by cytohesin-2", Proc Natl Acad Sci 101, 11221-11226 (2004).
Tuerk, et al., "Systematic evolution of ligands by exponential enrichment: RNA ligands to bacteriophage T4 DNA polymerase", Science 249, 505-510 (1990).
Wullner, et al., "Cell-specific induction of apoptosis by rationally designed bivalent aptamer-siRNA transcripts silencing eukaryotic elongation factor 2", Curr Cancer Drug Targets 8, 554-565 (2008).
Zimmermann, et al., "Monitoring Genomic Sequences during SELEX Using High-Throughput Sequencing: Neutral SELEX", PLoS One 5 (2), e9169, 7 pages (2010).
Zuker et al., "Optimal computer folding of large RNA sequences using thermodynamics and auxiliary information", Nucleic Acids Res 9, 133-148 (1981).
Ahmad, et al., "Probing the limits of aptamer affinity with a microfluidic SELEX platform", PLoS One 6 (11), e27051, 8 pages (2011).
Allen, et al., "Isolation of high-affinity RNA ligands to HIV-1 integrase from a random pool", Virology 209, 327-336 (1995).
Berezhnoy, et al., "Isolation and Optimization of Murine IL-10 Receptor Blocking Oligonucleotide Aptamers Using High-throughput Sequencing", Mol Ther. vol. 20 (6), 1242-1250 (2012).
Binkley, et al., "RNA ligands to human nerve growth factor", Nucleic Acids Res 23(16), 3198-3205 (1995).
Blank, et al., "Systematic evolution of a DNA aptamer binding to rat brain tumor microvessels. selective targeting of endothelial regulatory protein pigpen", Journal of Biological Chemistry vol. 276 (19), 16464-16468 (2001).
Bock, et al., "Selection of single-stranded DNA molecules that bind and inhibit human thrombin", Nature 355, 564-566 (1992).
Bompfunewerer, et al., "Variations on RNA folding and alignment: lessons from Benasque", J Math Biol 56, 129-144 (2008).
Cerchia, et al., "Differential SELEX in human glioma cell lines", PLoS One 4 (11), e7971, 10 pages (2009).
Cerchia, et al., "Neutralizing aptamers from whole-cell SELEX inhibit the RET receptor tyrosine kinase", PLoS Biol 3 (4), e123, 8 pages (2005).
Cerchia, et al., "Targeting cancer cells with nucleic acid aptamers", Trends Biotechnol 28 (10), 517-525 (2010).
Charlton, et al., "Highly potent irreversible inhibitors of neutrophil elastase generated by selection from a randomized DNA-valine phosphonate library", Biochemistry 36, 3018-3026 (1997).
Chen, et al., "Aptamer from whole-bacterium SELEX as new therapeutic reagent against virulent *Mycobacterium tuberculosis*", Biochem Biophys Res Commun 357, 743-748 (2007).
Chen, et al., "Inhibition of heregulin signaling by an aptamer that preferentially binds to the oligomeric form of human epidermal growth factor receptor-3", PNAS 100 (16), 9226-9231 (2003).
Cho, et al., "Quantitative selection of DNA aptamers through microfluidic selection and high-throughput sequencing", Proc Natl Acad Sci 107 (35), 15373-15378 (2010).
Daniels, et al., "A tenascin-C aptamer identified by tumor cell SELEX: systematic evolution of ligands by exponential enrichment", Proc Natl Acad Sci 100 (26), 15416-15421 (2003).
Ellington, et al., "In vitro selection of RNA molecules that bind specific ligands", Nature 346, 818-822 (1990).

Fukuda, et al., "Isolation and characterization of RNA aptamers specific for the hepatitis C virus nonstructural protein 3 protease", Eur J Biochem 267, 3685-3694 (2000).
Giangrande, et al., "Distinct roles of E2F proteins in vascular smooth muscle cell proliferation and intimal hyperplasia", Proc Natl Acad Sci U S A.104 (32), 12988-93 (2007).
Giver, et al., "Selection and design of high-affinity RNA ligands for HIV-1", Gene 137, 19-24 (1993).
Green, et al., "Inhibitory DNA ligands to platelet-derived growth factor B-chain", Biochemistry 35, 14413-14424 (1996).
Guo, et al., "CELL-SELEX: Novel perspectives of aptamer-based therapeutics", Int J Mol Sci 9, 668-678 (2008).
Hernandez, et al., "Degradation of nuclease-stabilized RNA oligonucleotides in Mycoplasma-contaminated cell culture media", Nucleic Acid Ther 22, 58-68 (2012).
Hicke, et al., "Tenascin-C aptamers are generated using tumor cells and purified protein", J Biol Chem 276, 48644-48654 (2001).
Hofacker, et al., "Fast folding and comparison of RNA secondary structures", Monatshefte für Chemie / Chemical Monthly 125, 167-188 (1994).
Homann, et al., "Combinatorial selection of high affinity RNA ligands to live African trypanosomes", Nucleic Acids Res 27, 2006-2014 (1999).
Huang, et al., "Mechanism of ribose 2'-group discrimination by an RNA polymerase", Biochemistry 36, 8231-8242 (1997).
Jellinek, et al., "High-affinity RNA ligands to basic fibroblast growth factor inhibit receptor binding", Proc Natl Acad Sci U S A 90, 11227-11231 (1993).
Keefe, et al., "Aptamers as therapeutics", Nat Rev Drug Discov 9, 537-550 (2010).
Khati, et al., "Neutralization of infectivity of diverse R5 clinical isolates of human immunodeficiency virus type 1 by gp120-binding 2'F-RNA aptamers", J Virol 77, 12692-12698 (2003).
Kraus, et al., "Cutting edge: novel RNA ligands able to bind CD4 antigen and inhibit CD4+ T lymphocyte function", J Immunol 160, 5209-5212 (1998).
Kubik, et al., "Isolation and characterization of 2'-fluoro-, 2'-amino-, and 2'-fluoro-/amino-modified RNA ligands to human IFN-gamma that inhibit receptor binding", J Immunol 159, 259-267 (1997).
Layzer, et al., "Simultaneous generation of aptamers to multiple gamma-carboxyglutamic acid proteins from a focused aptamer library using DeSELEX and convergent selection", Oligonucleotides 17, 1-11 (2007).
Lebruska, et al., "Selection and characterization of an RNA decoy for transcription factor NF-kappa B", Biochemistry 38, 3168-3174 (1999).
Li, et al., "Label-free aptamer-based calorimetric detection of mercury ions in aqueous media using unmodified gold nanoparticles as colorimetric probe", Anal Bioanal Chem 393, 2051-2057 (2009).
Liu, et al., "Targeting inhibition of GluR1 Ser845 phosphorylation with an RNA aptamer that blocks AMPA receptor trafficking", J Neurochem 108, 147-157 (2009).
Lorenz, et al., "ViennaRNA Package 2.0", Algorithms Mol Biol 6, 26 (2011).
Lundberg, et al., "Delivery of short interfering RNA using endosomolytic cell-penetrating peptides", FASEB J 21, 2664-2671 (2007).
Lupold, et al., "Identification and Characterization of Nuclease-stabilized RNA Molecules That Bind Human Prostate Cancer Cells via the Prostate-specific Membrane Antigen", Cancer Research 62, 4029-4033 (2002).
Mallikaratchy, et al., "Selection of DNA ligands for protein kinase C-delta", Chem Commun, 3229-3231 (2006).
Martell, et al., "Optimizing aptamer activity for gene therapy applications using expression cassette SELEX", Mol Ther 6 (1), 30-34 (2002).
Mayer, et al., "Controlling small guanine-nucleotide-exchange factor function through cytoplasmic RNA intramers", Proc Natl Acad Sci U S A 98 (9), 4961-4965 (2001).
McCaskill, "The equilibrium partition function and base pair binding probabilities for RNA secondary structure", Biopolymers 29, 1105-1119 (1990).

(56) References Cited

OTHER PUBLICATIONS

McNamara, et al., "Cell type-specific delivery of siRNAs with aptamer-siRNA chimeras", Nature Biotechnology 24 (8), 1005-1015 (2006).

McNamara, et al., "Multivalent 4-1BB binding aptamers costimulate CD8+ T cells and inhibit tumor growth in mice", Journal of Clinical Investigation 118, 376-386 (2008).

Meyer, et al., "Cell-specific aptamers as emerging therapeutics", J Nucleic Acids 2011, 904750, 18 pages (2011).

Mi, et al., "In vivo selection of tumor-targeting RNA motifs", Nat Chem Biol 6, 22-24 (2010).

Mi, et al., "RNA aptamer blockade of osteopontin inhibits growth and metastasis of MDA-MB231 breast cancer cells", Mol Ther 17, 153-161 (2009).

Mi, et al., "Targeted inhibition of alphavbeta3 integrin with an RNA aptamer impairs endothelial cell growth and survival", Biochem Biophys Res Commun 338, 956-963 (2005).

Morris, et al., "High affinity ligands from in vitro selection: complex targets", Proc Natl Acad Sci 95, 2902-2907 (1998).

Rockey, et al., "Rational truncation of an RNA aptamer to prostate-specific membrane antigen using computational structural modeling", Nucleic Acid Ther 21 (5), 299-314 (2011).

* cited by examiner

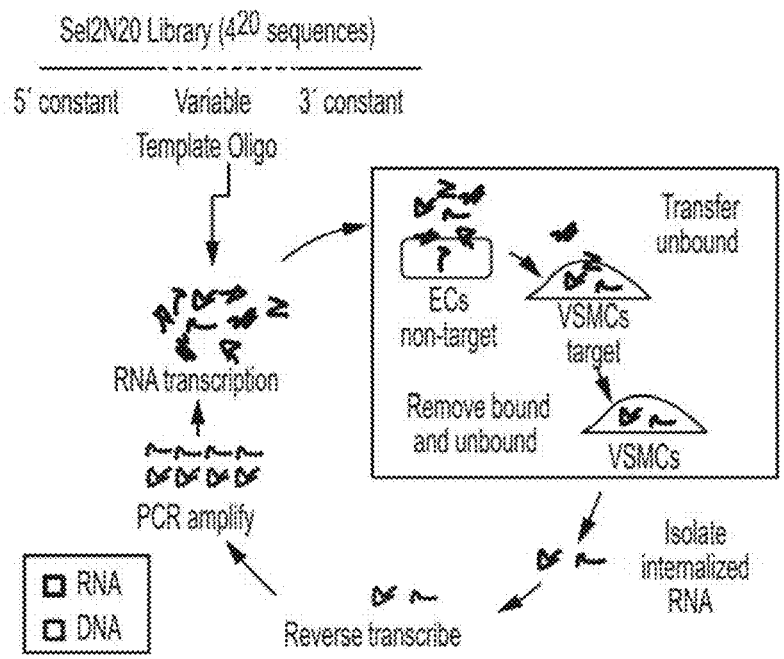
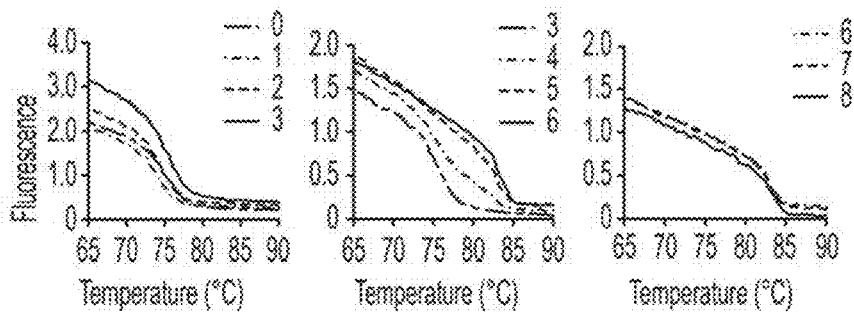
FIG. 1B  FIG. 1C  FIG. 1D
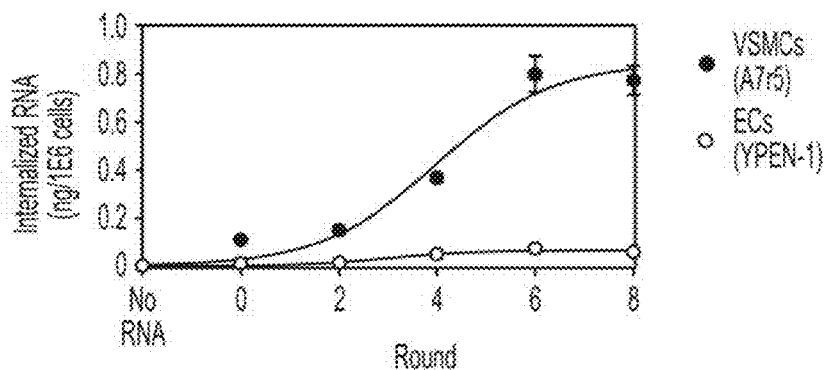
FIG. 1E

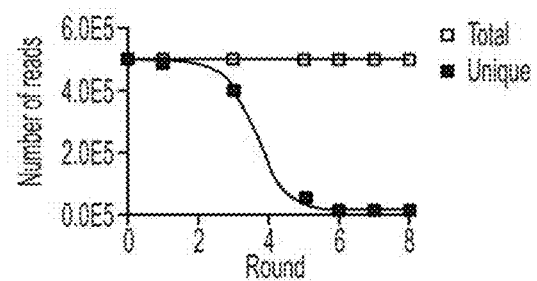
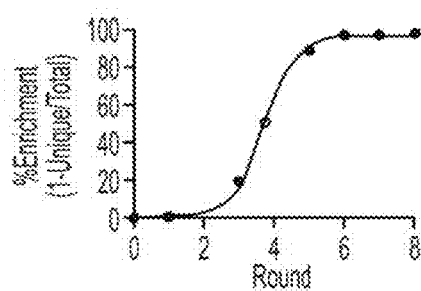
FIG. 2A  FIG. 2B
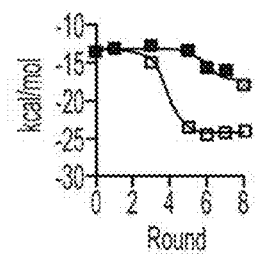
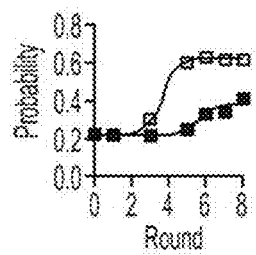
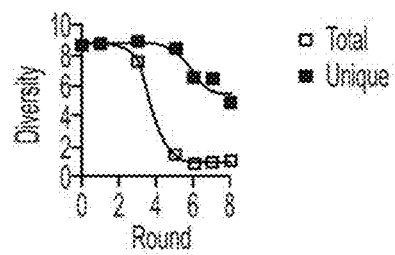
FIG. 2C  FIG. 2D  FIG. 2E

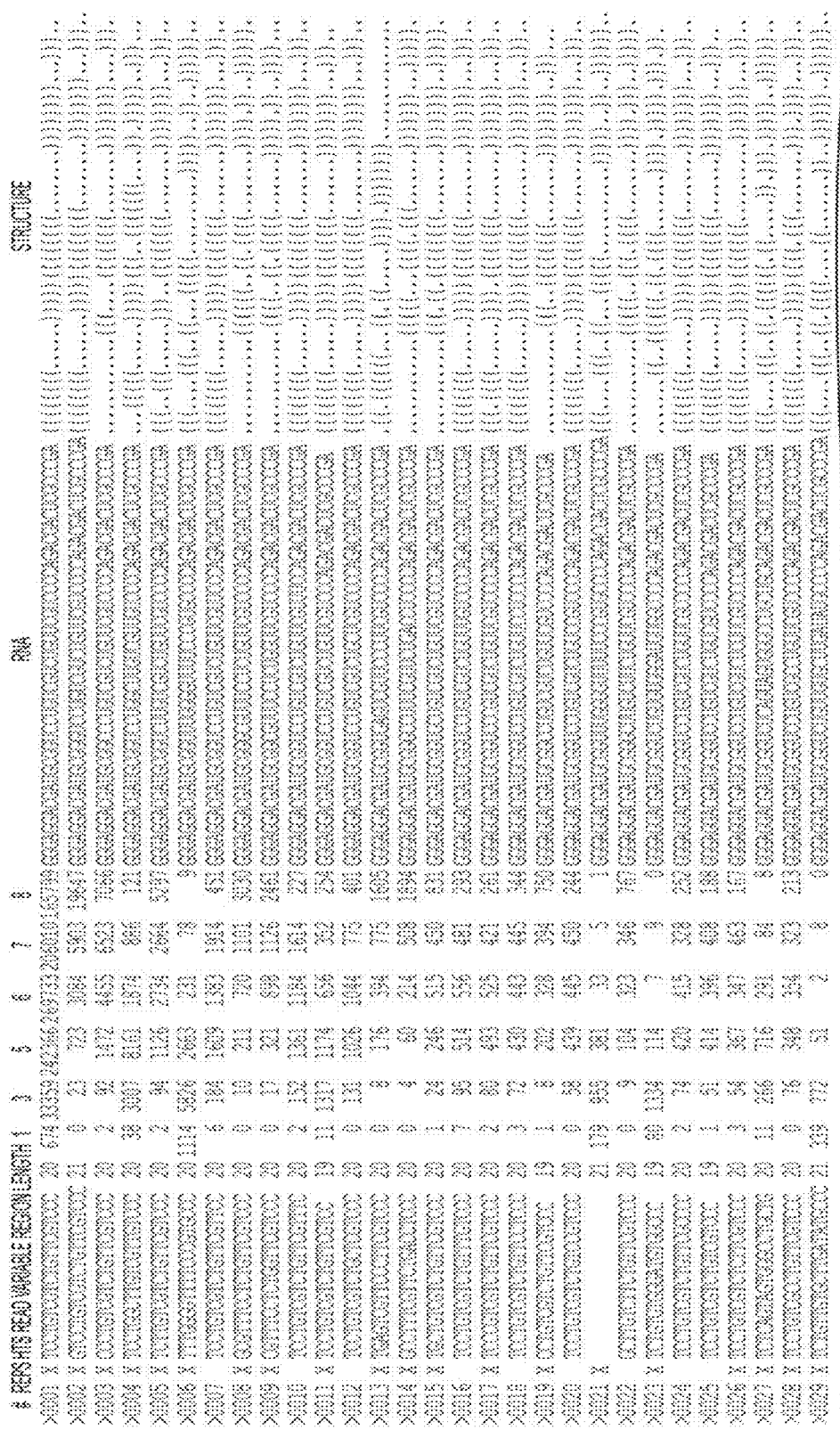

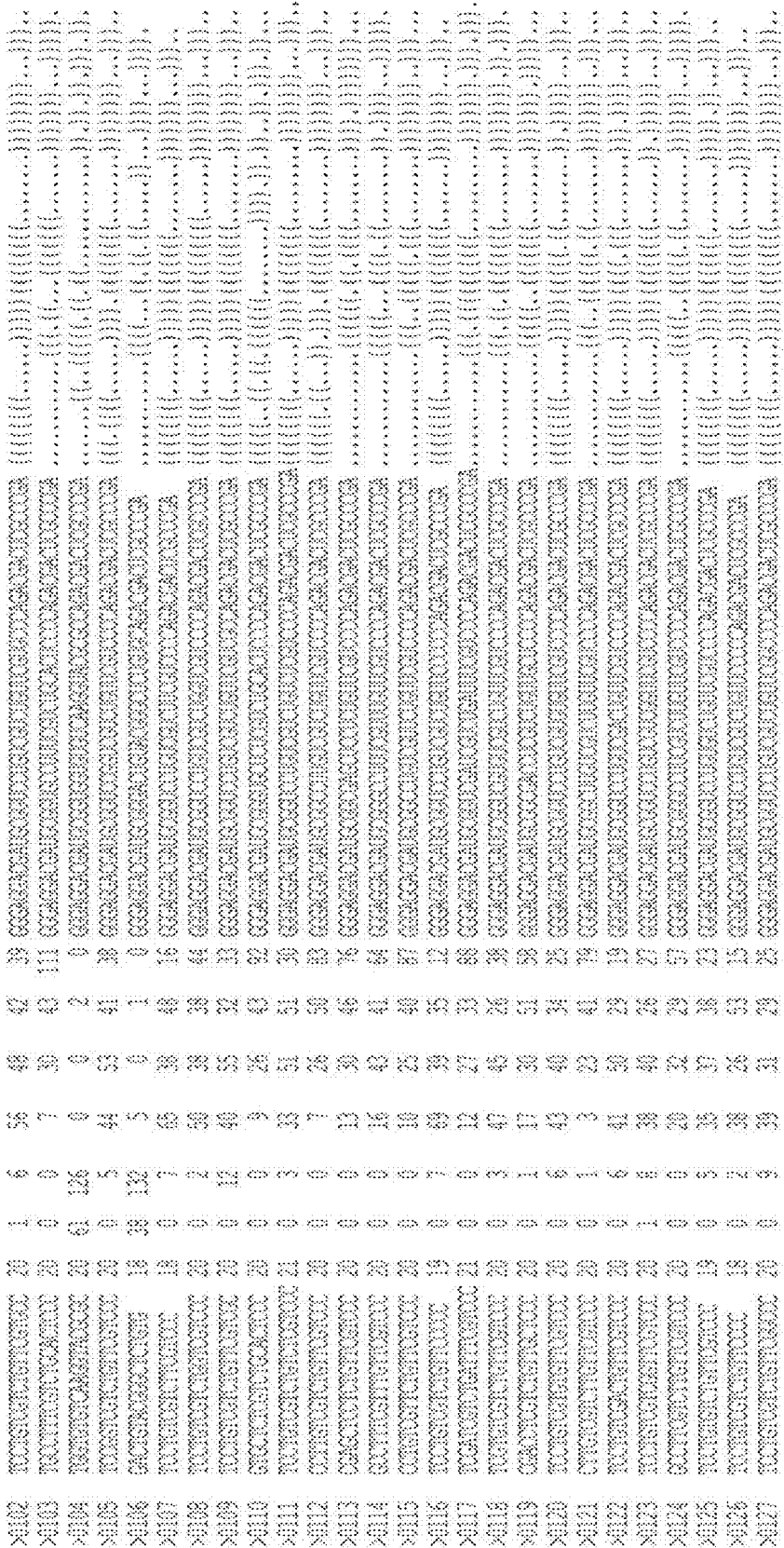

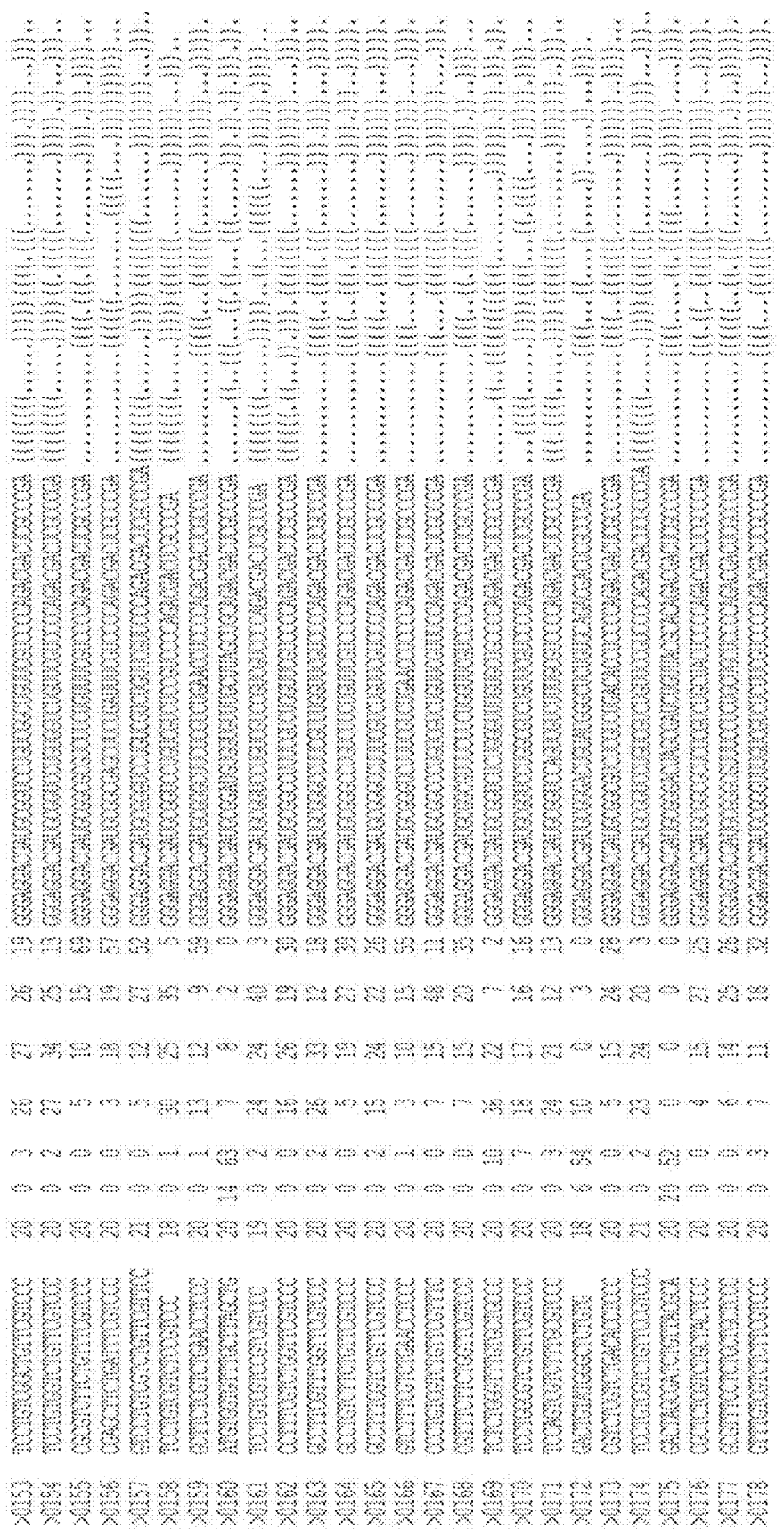

TO FIG. 12-6B

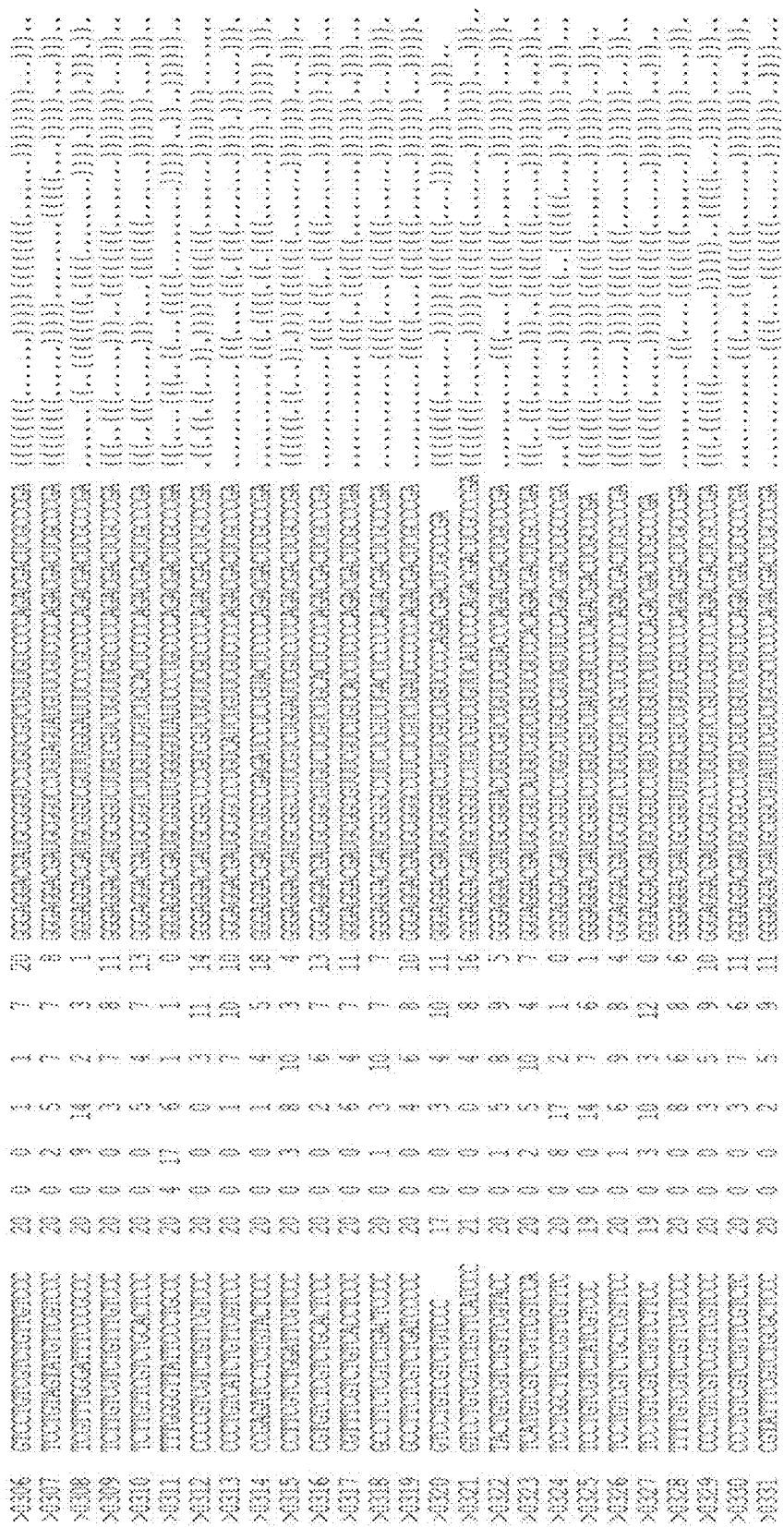

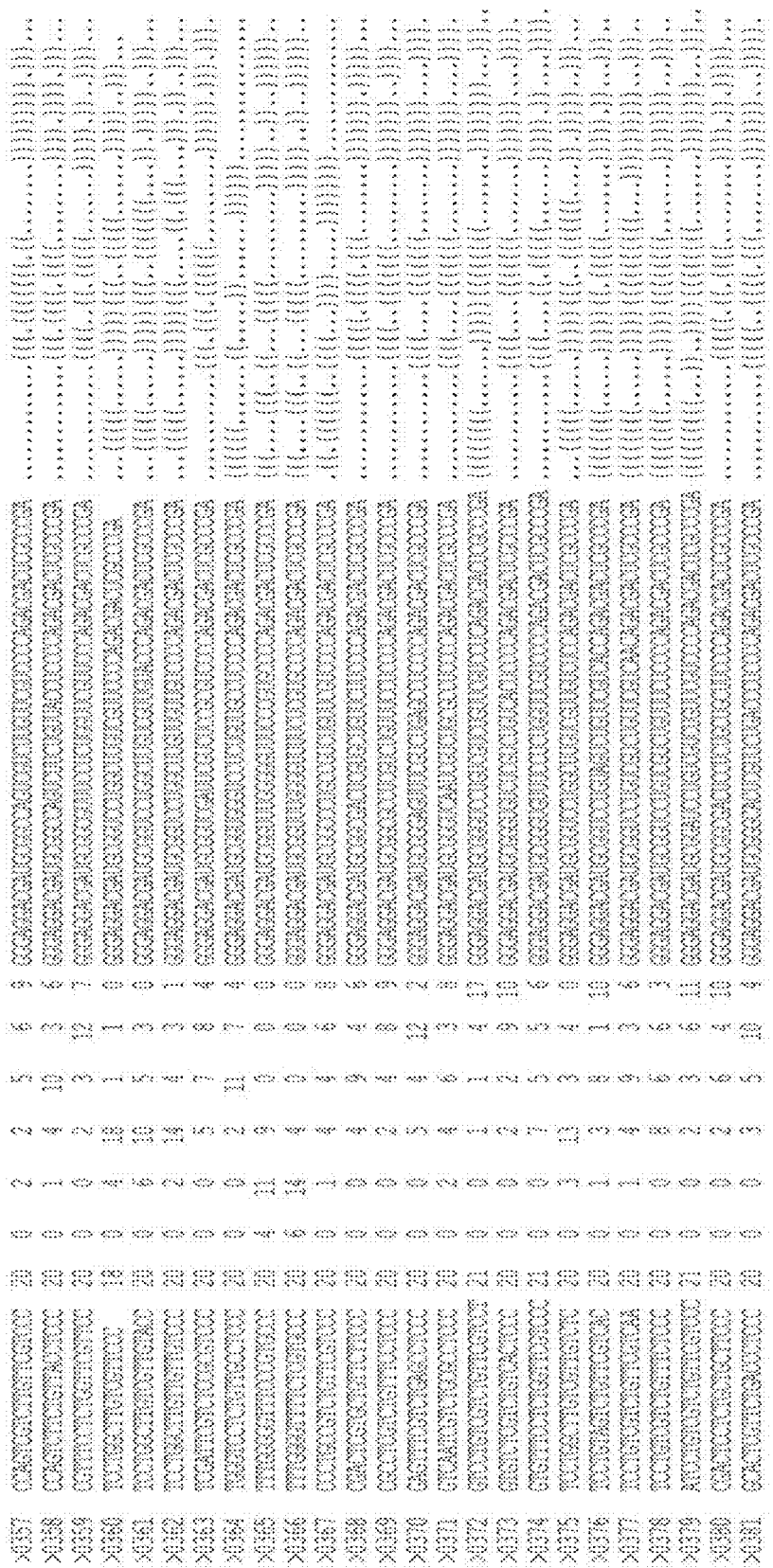

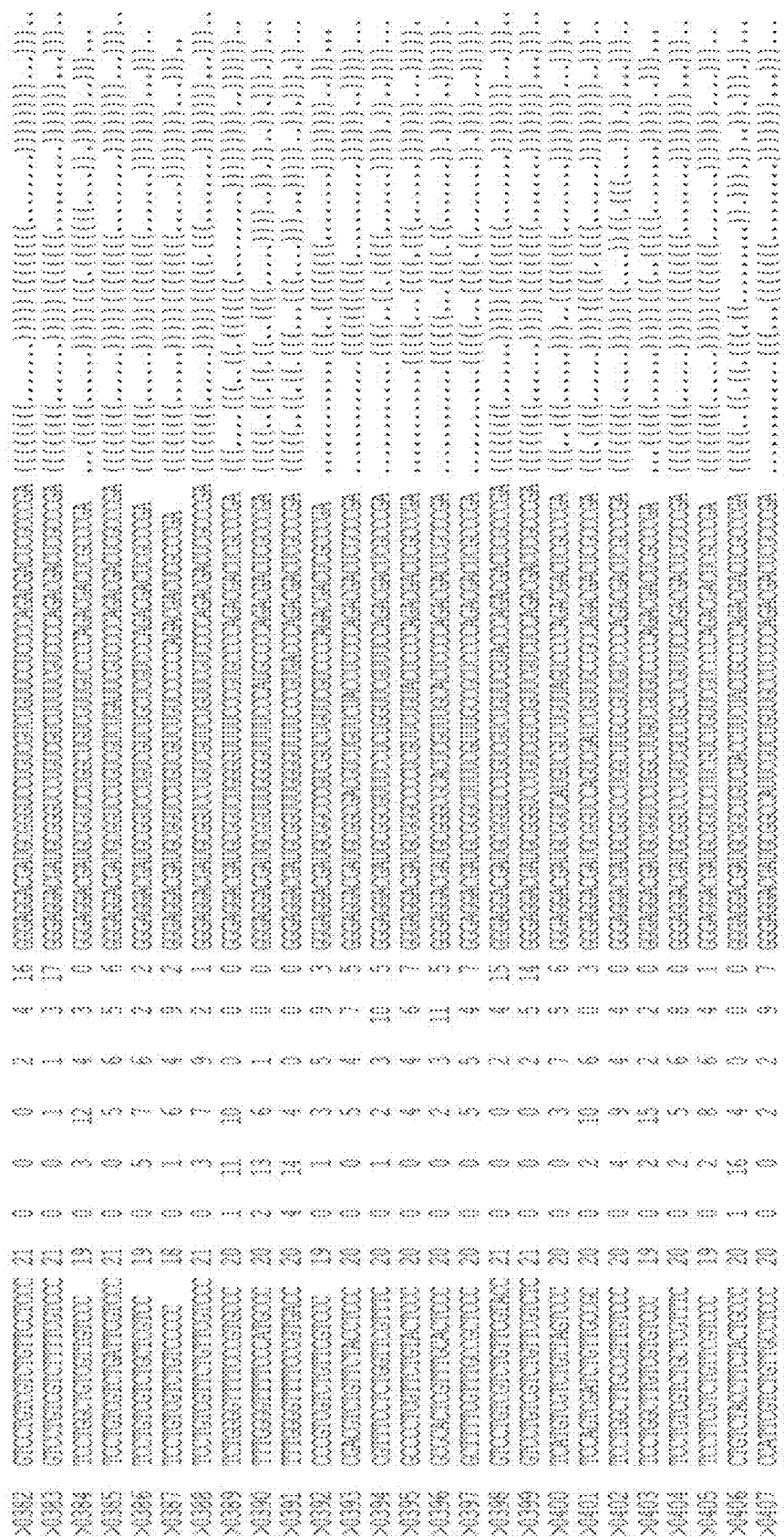

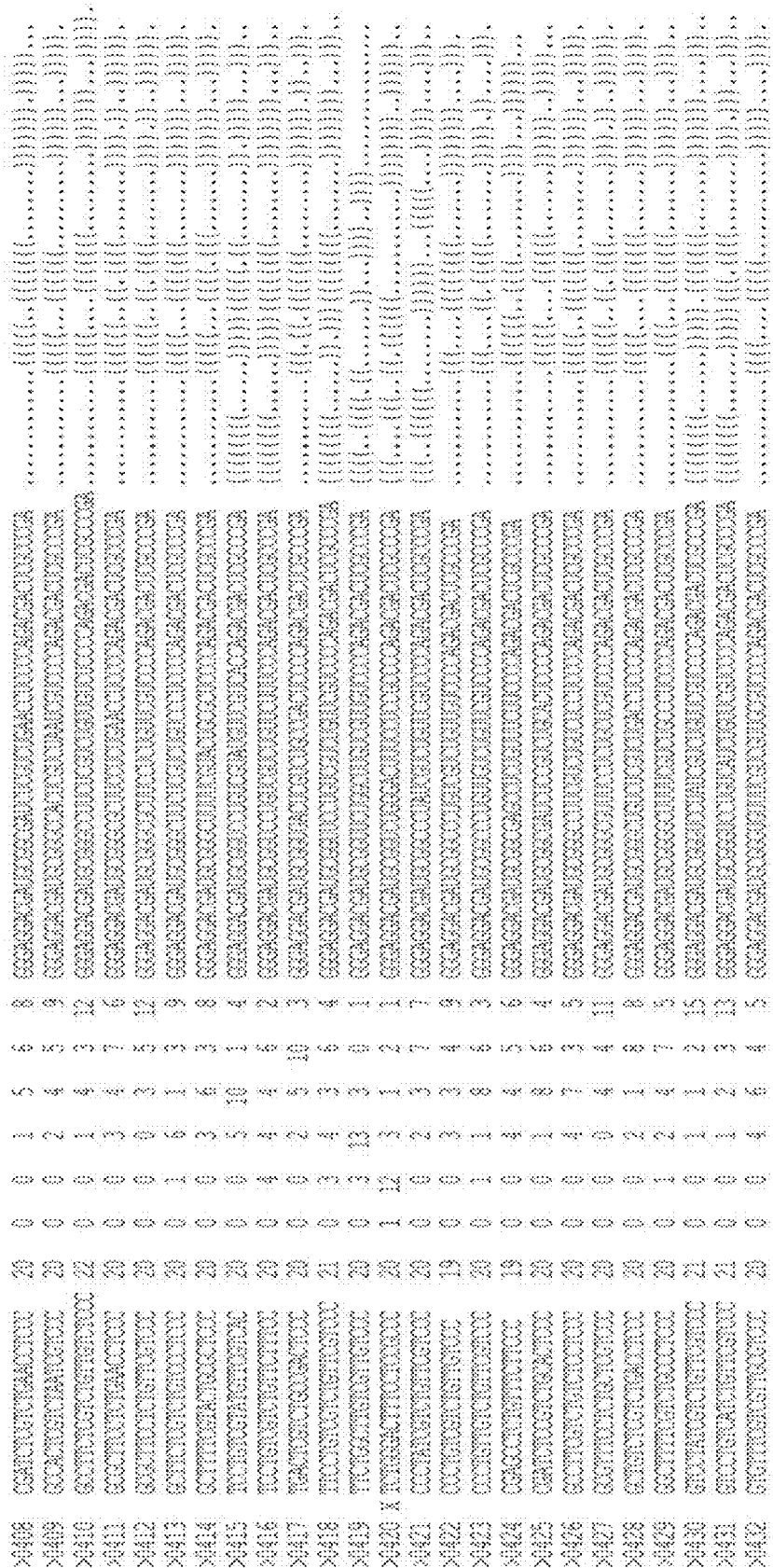

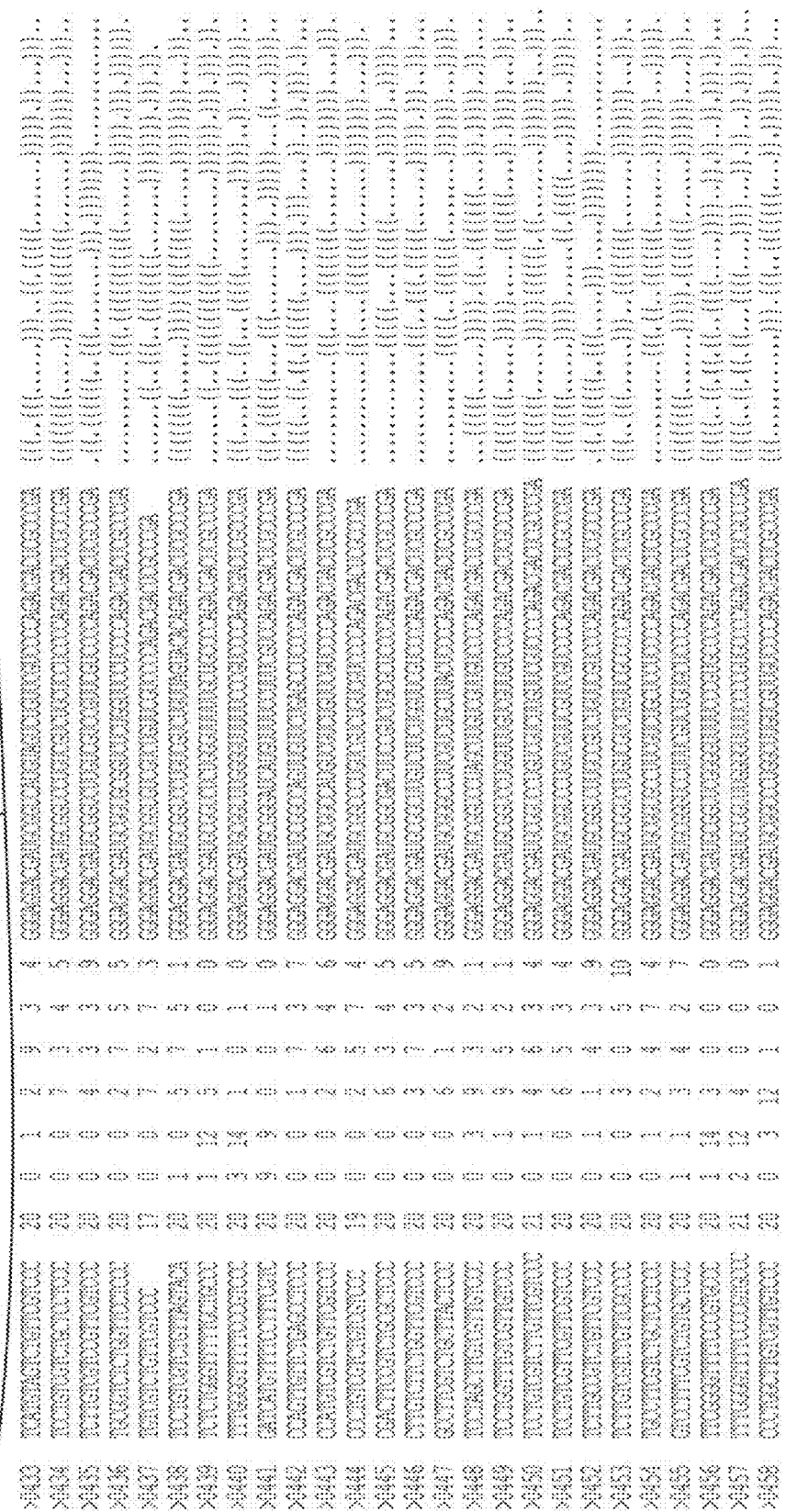

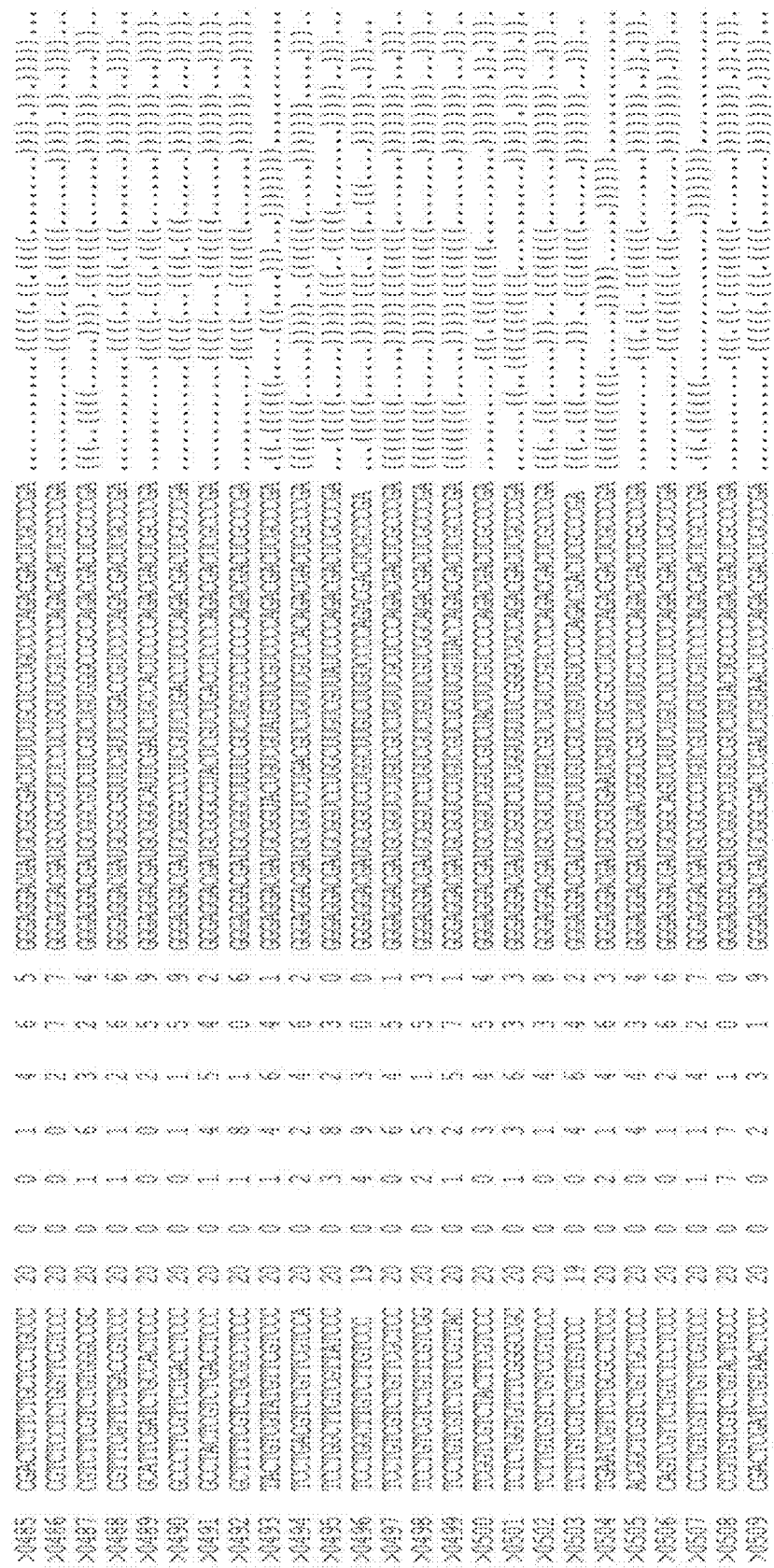

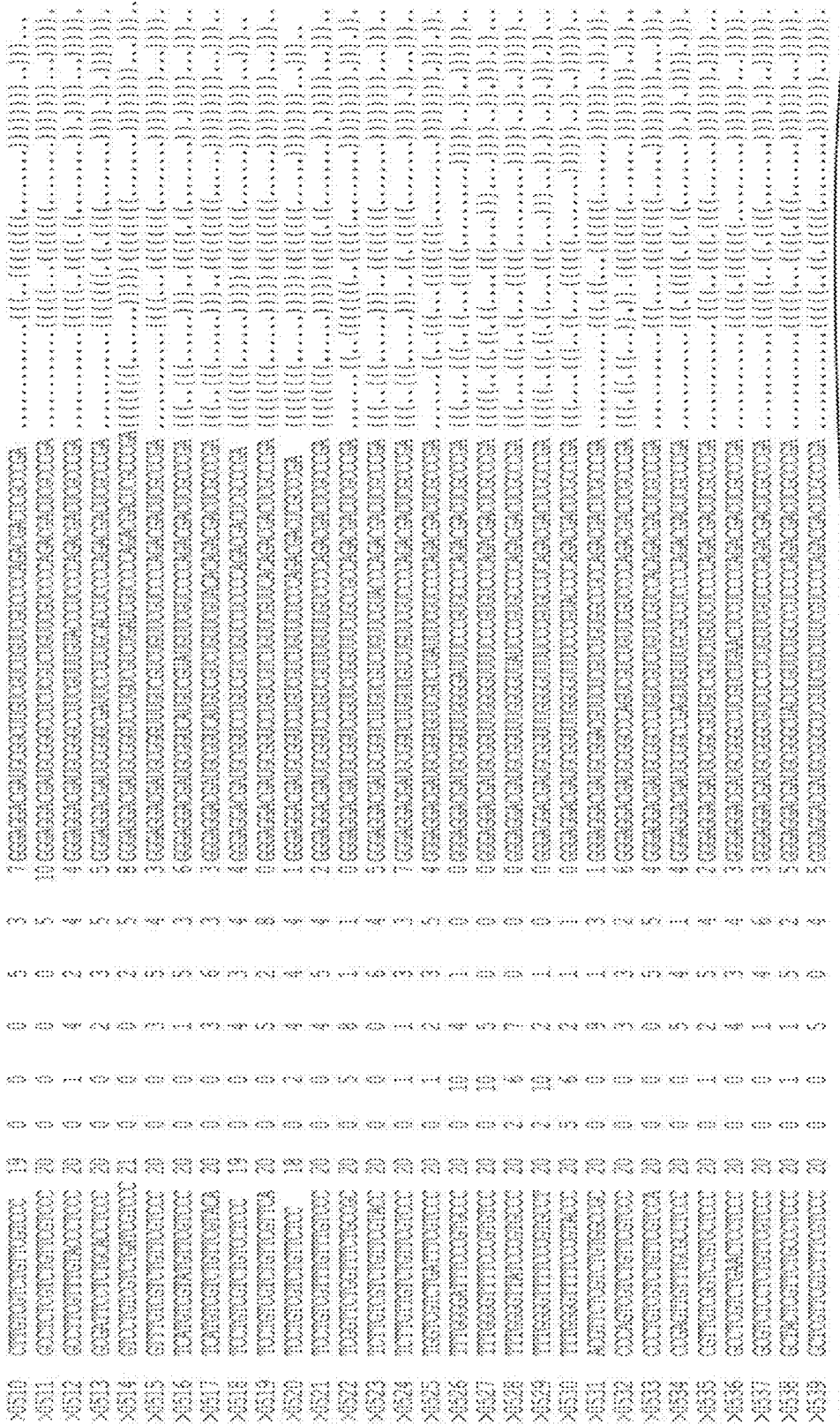

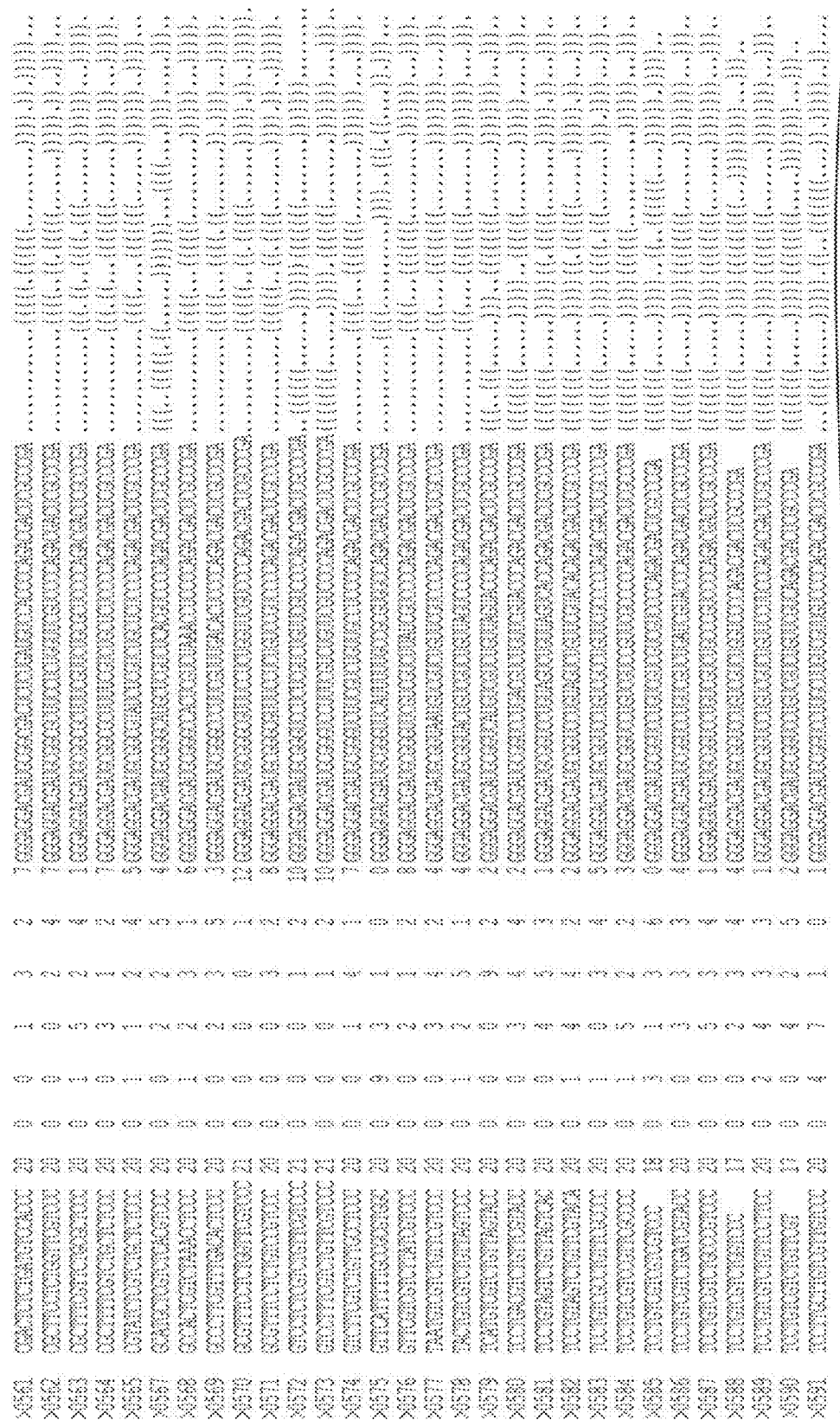

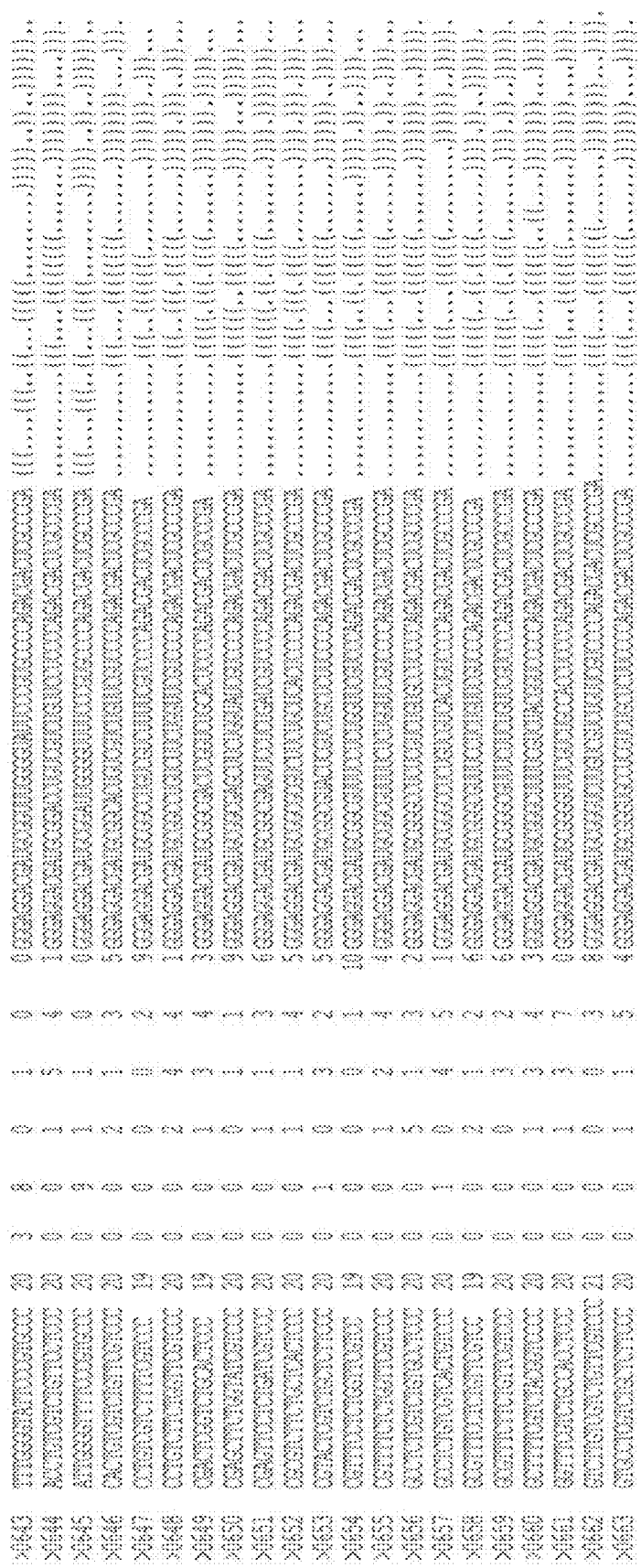

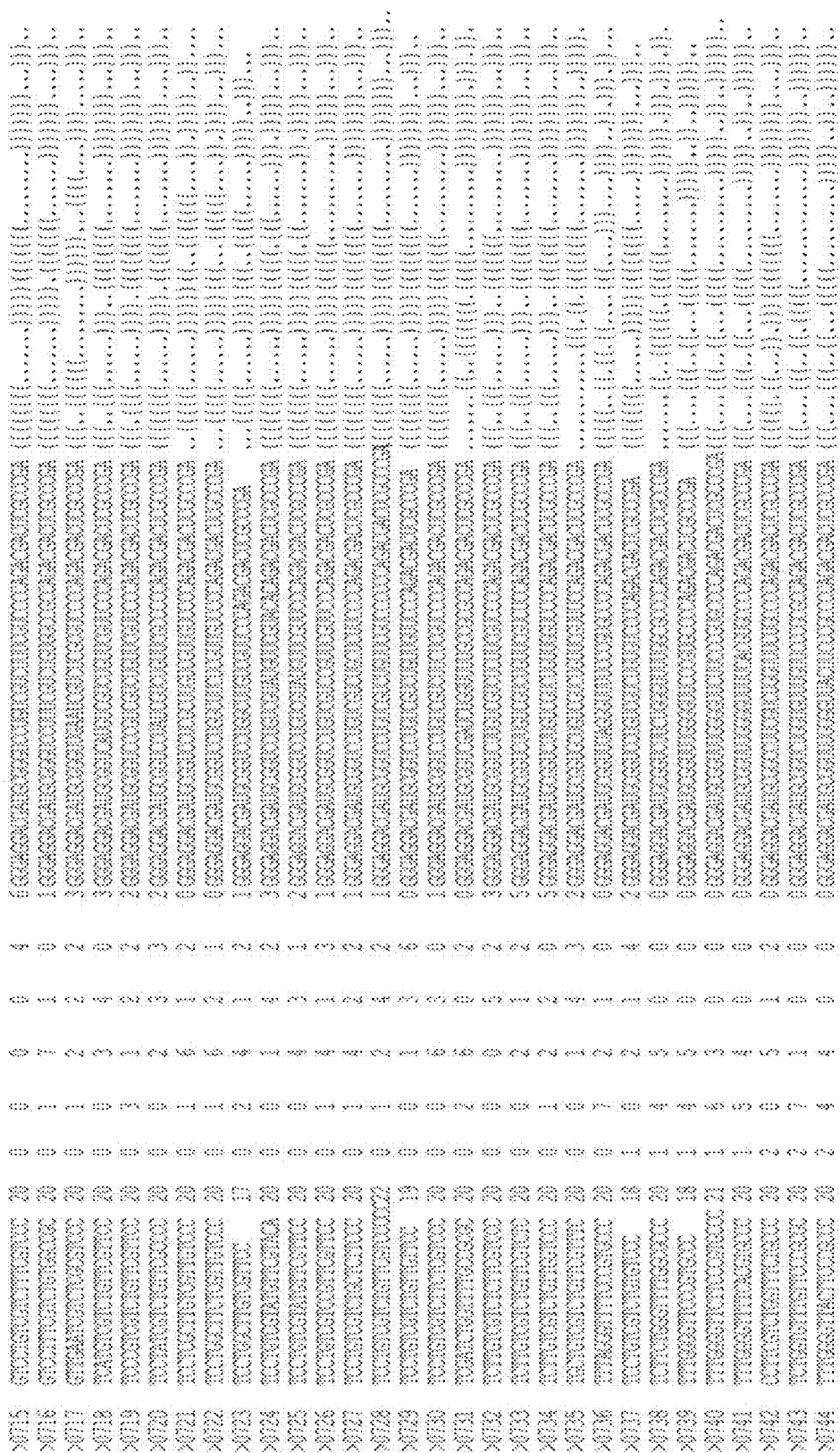

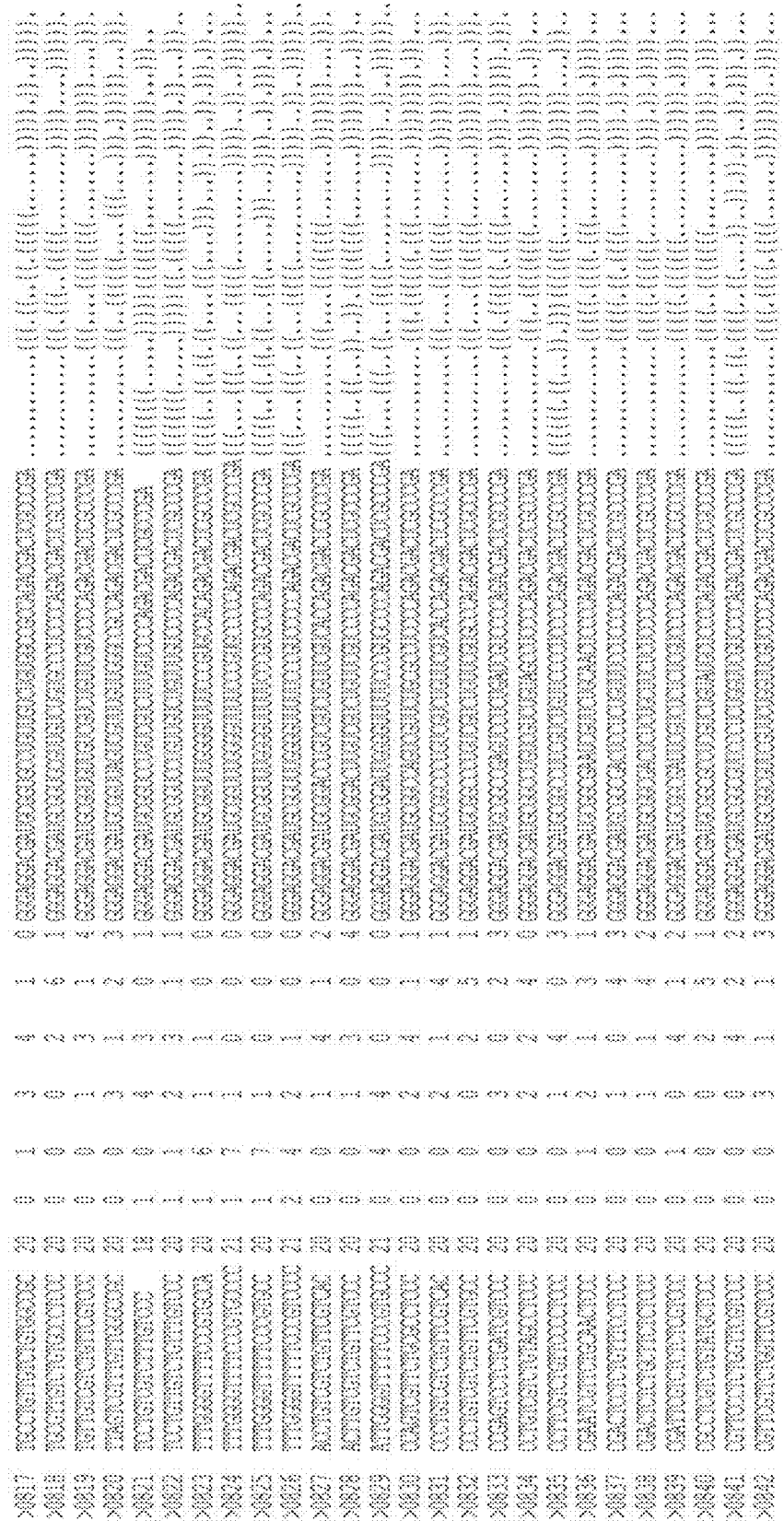

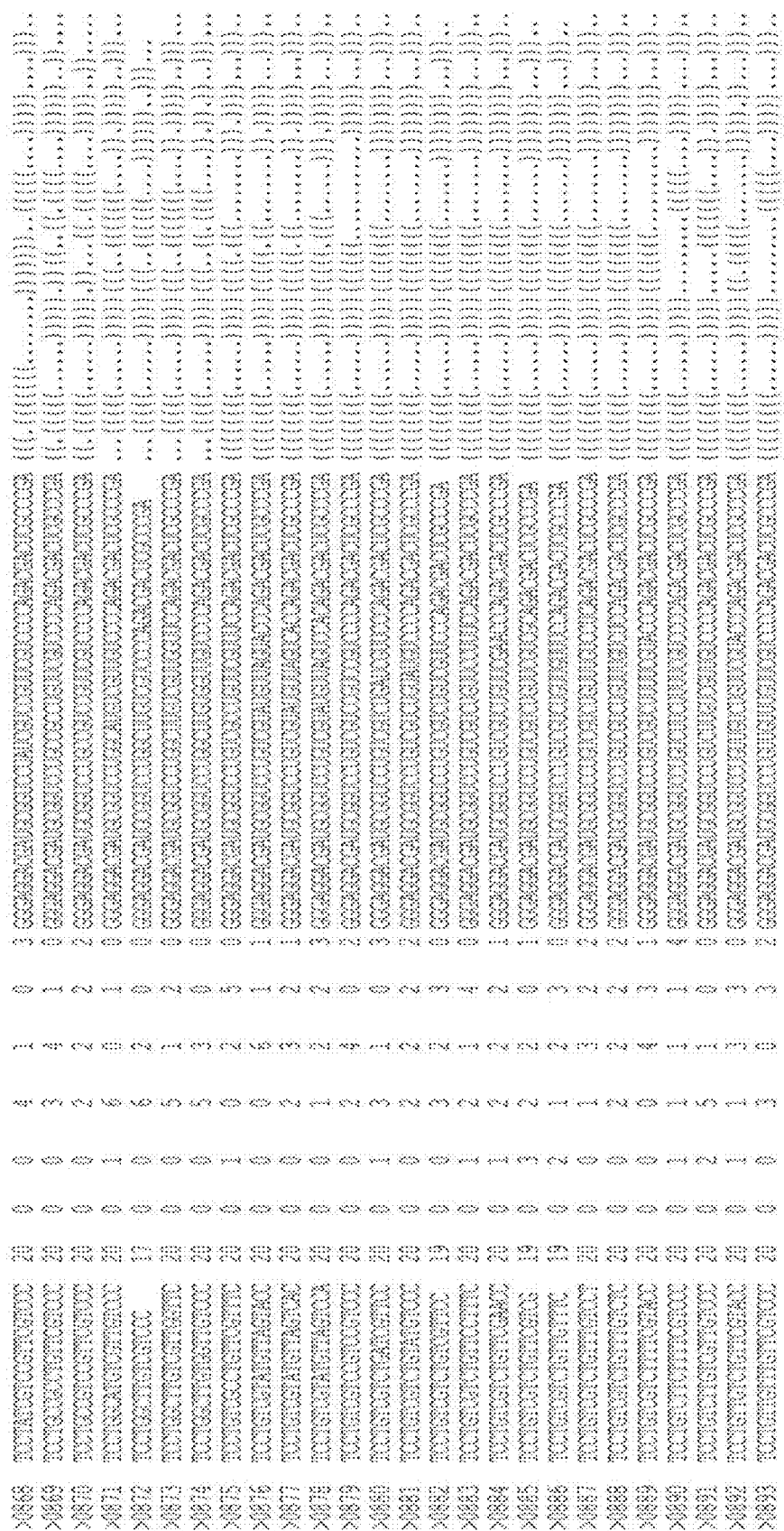

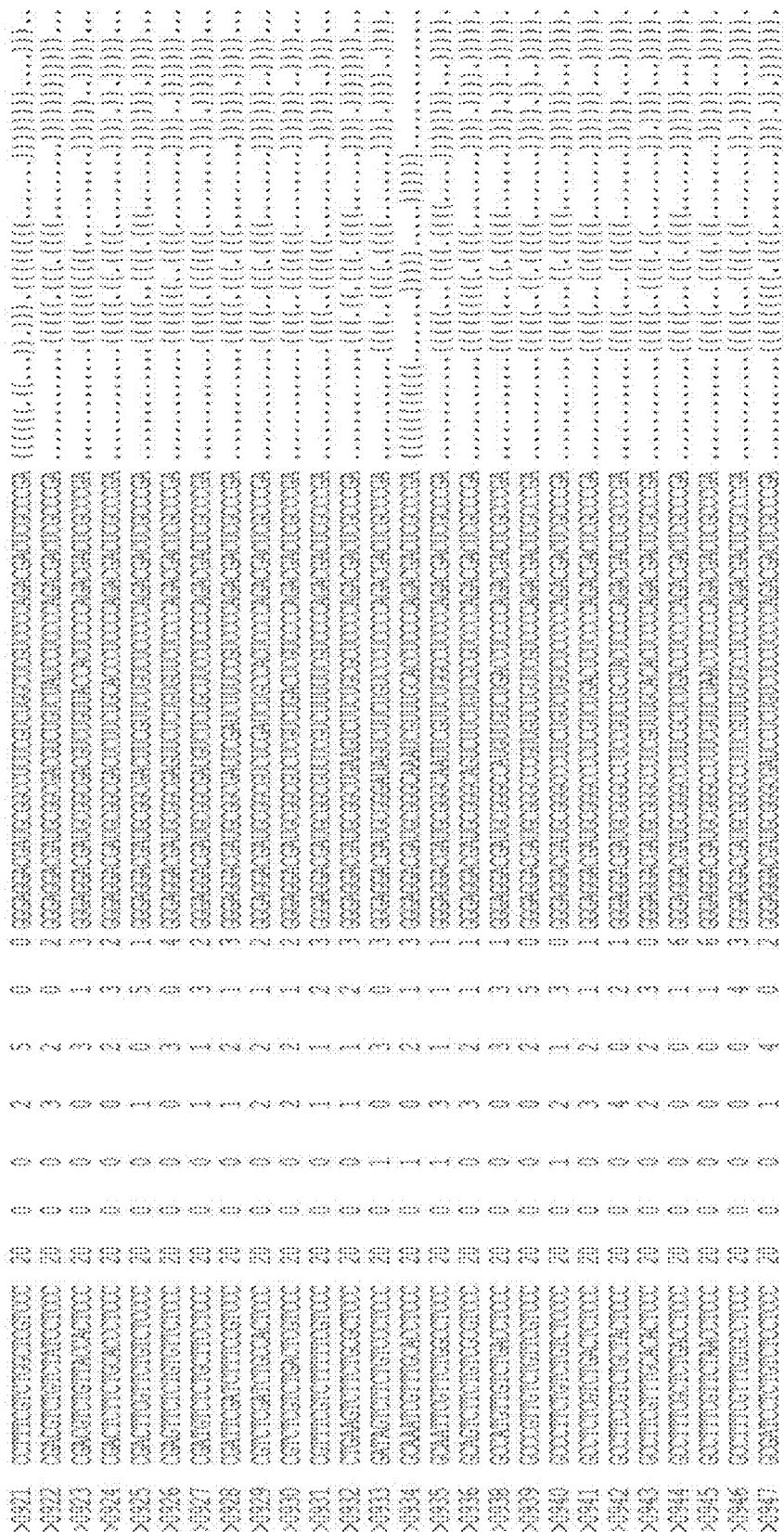

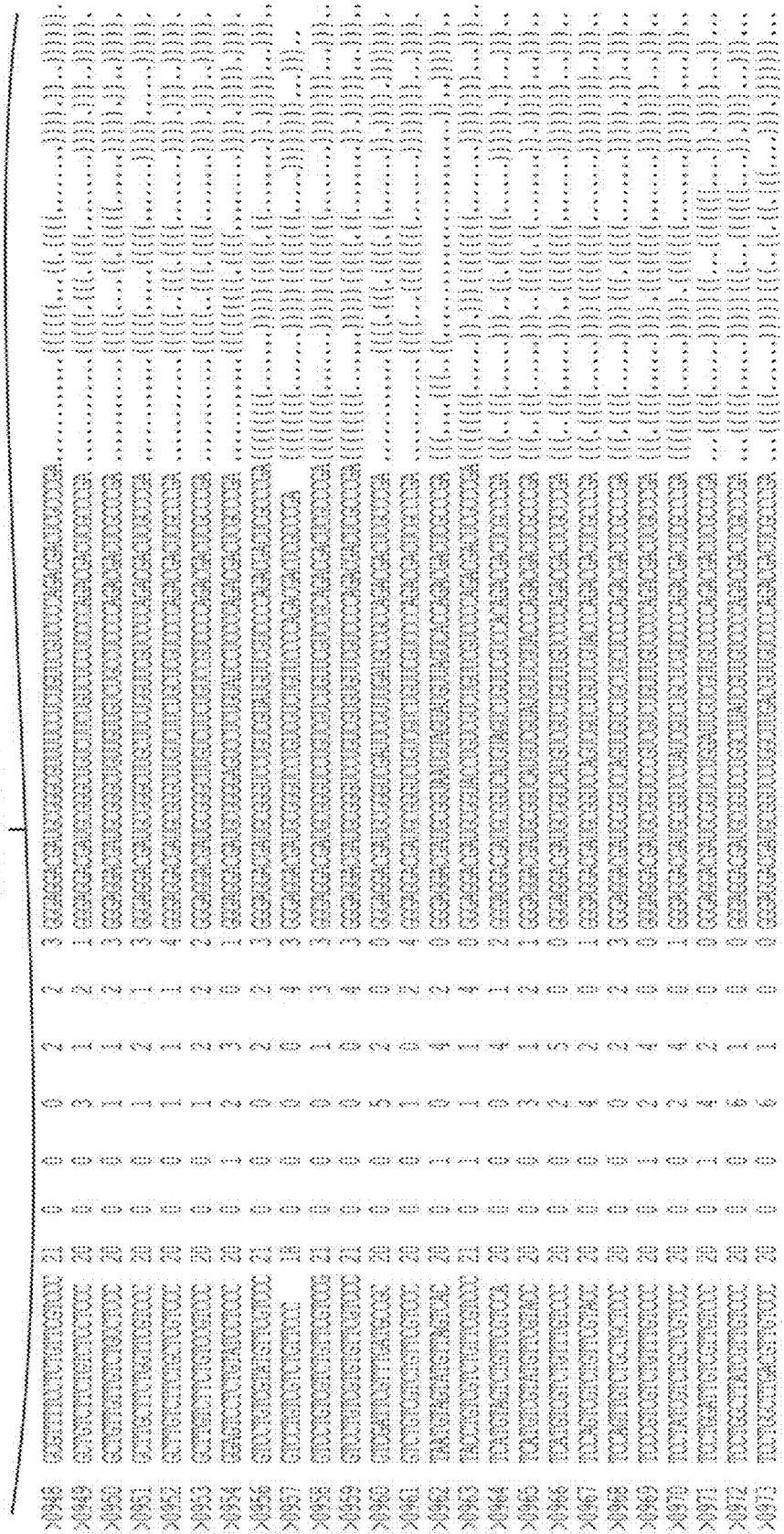

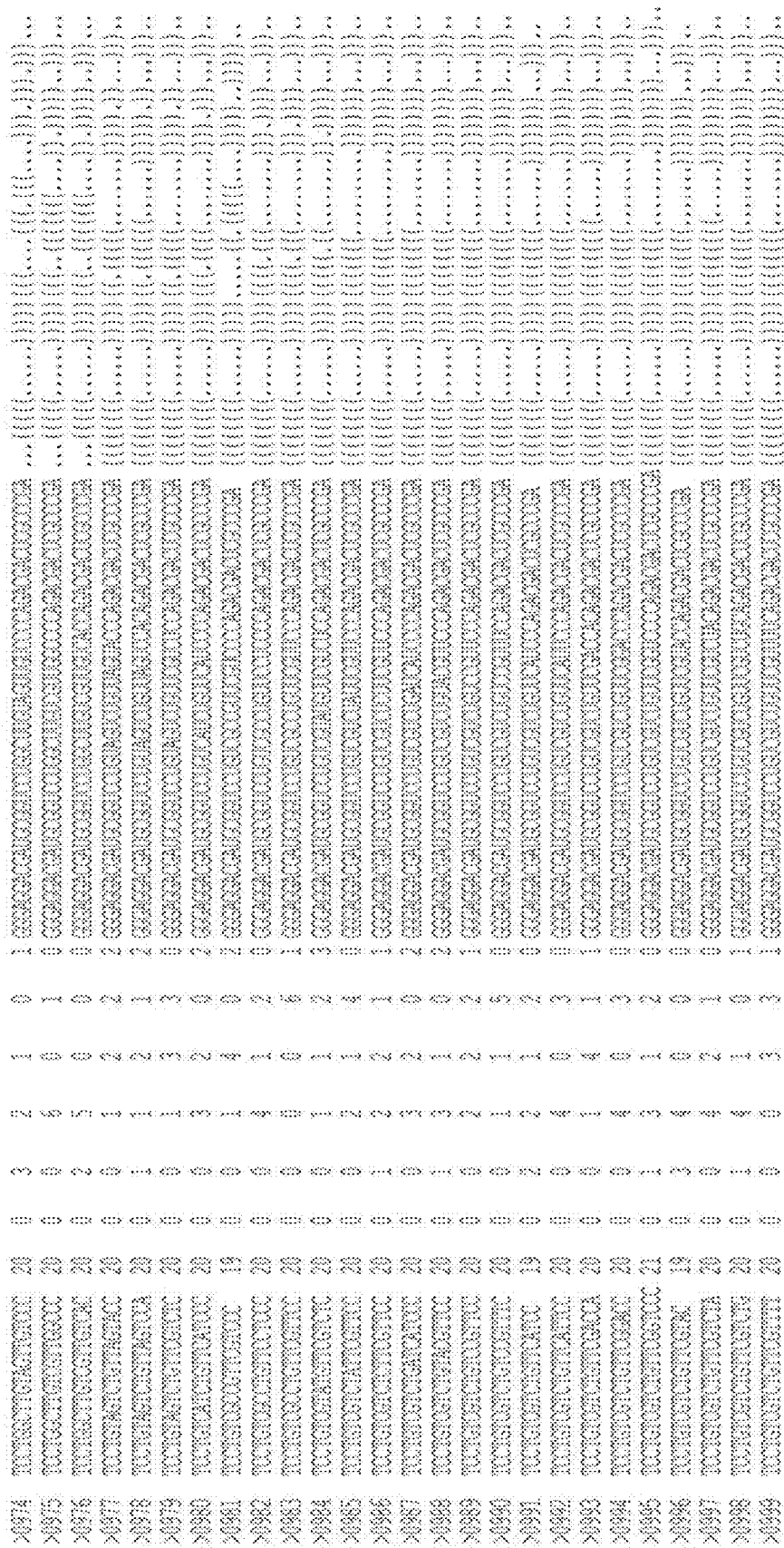

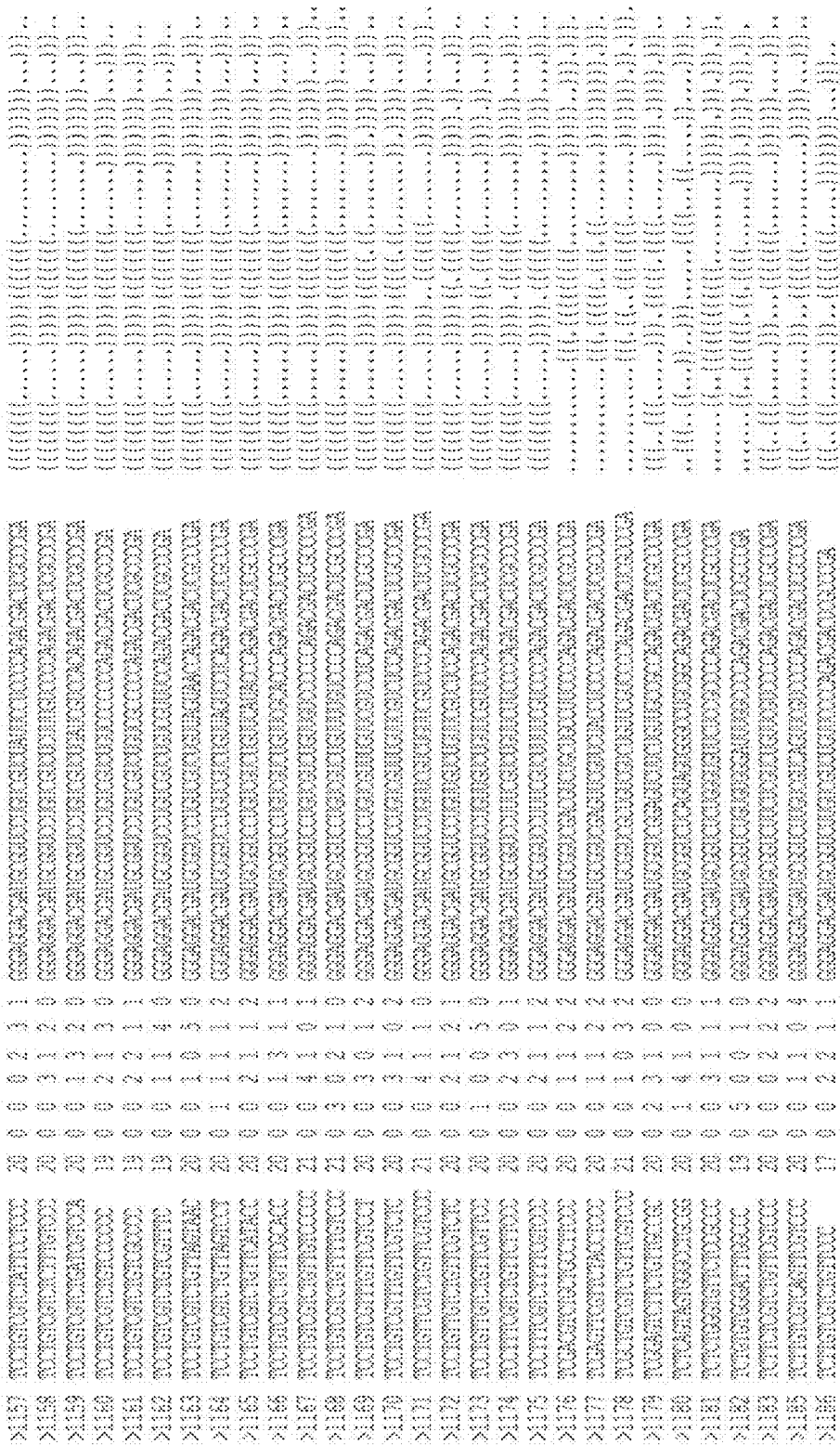

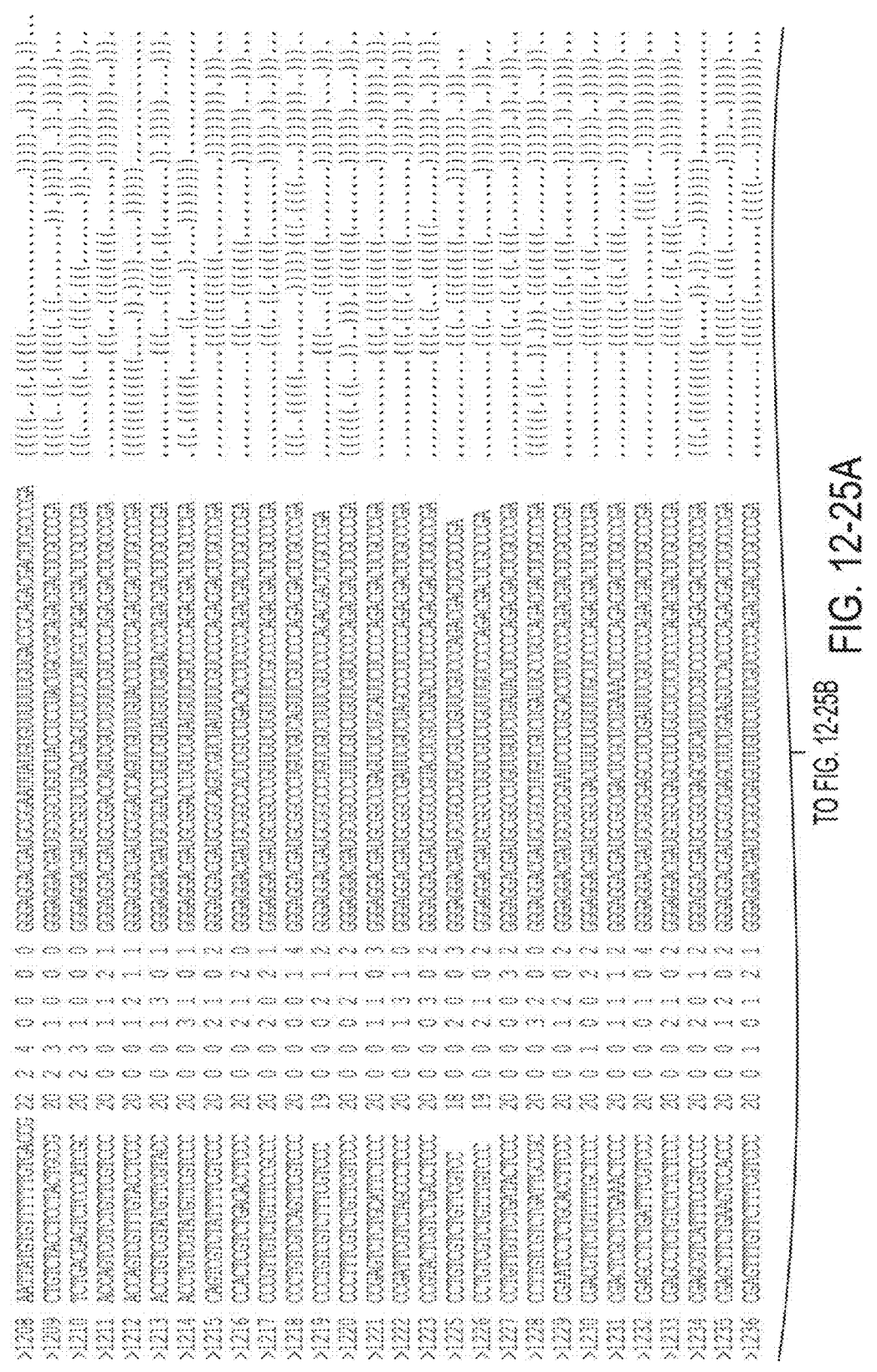

TO FIG. 12-25B    FIG. 12-25A

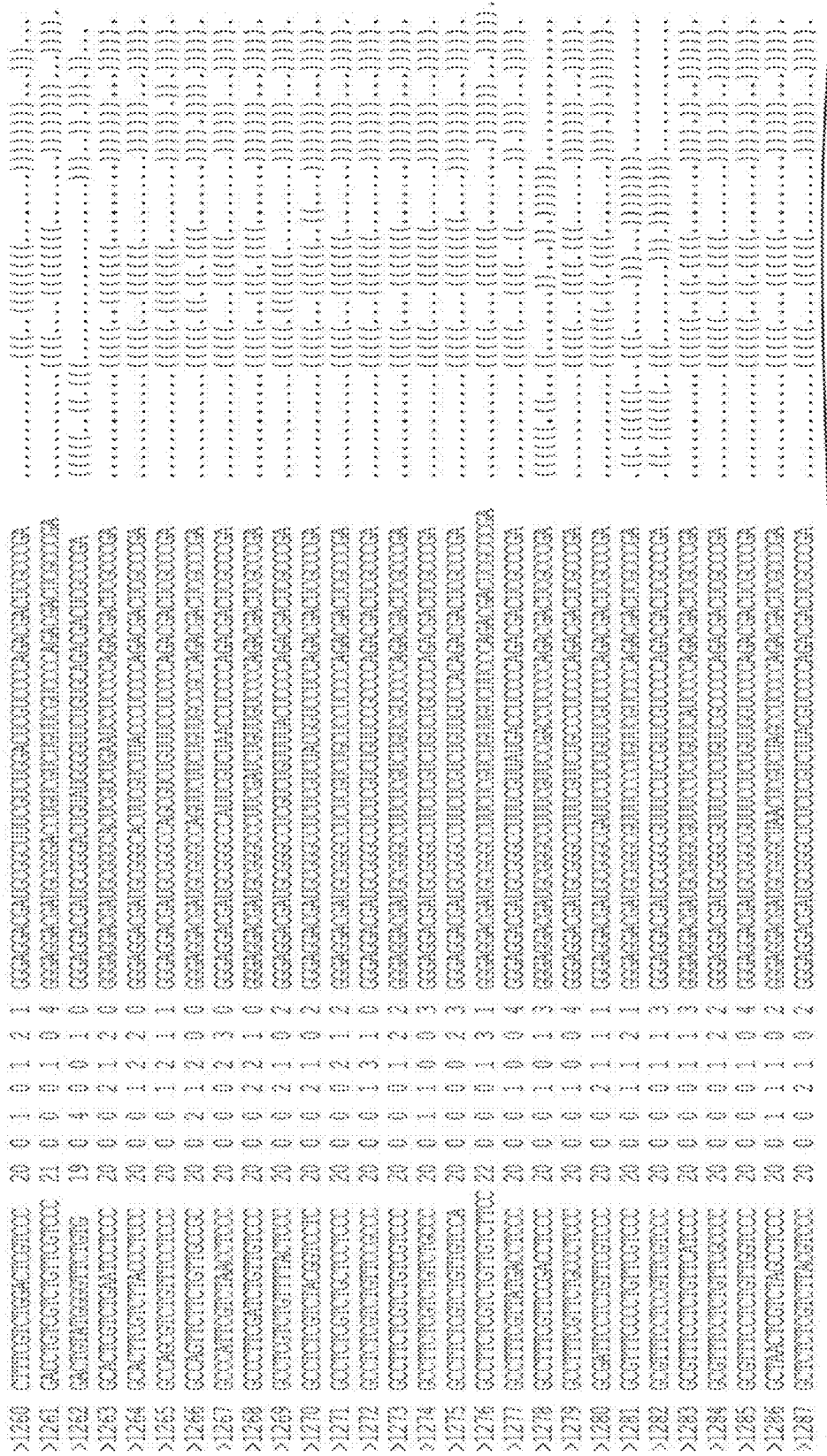

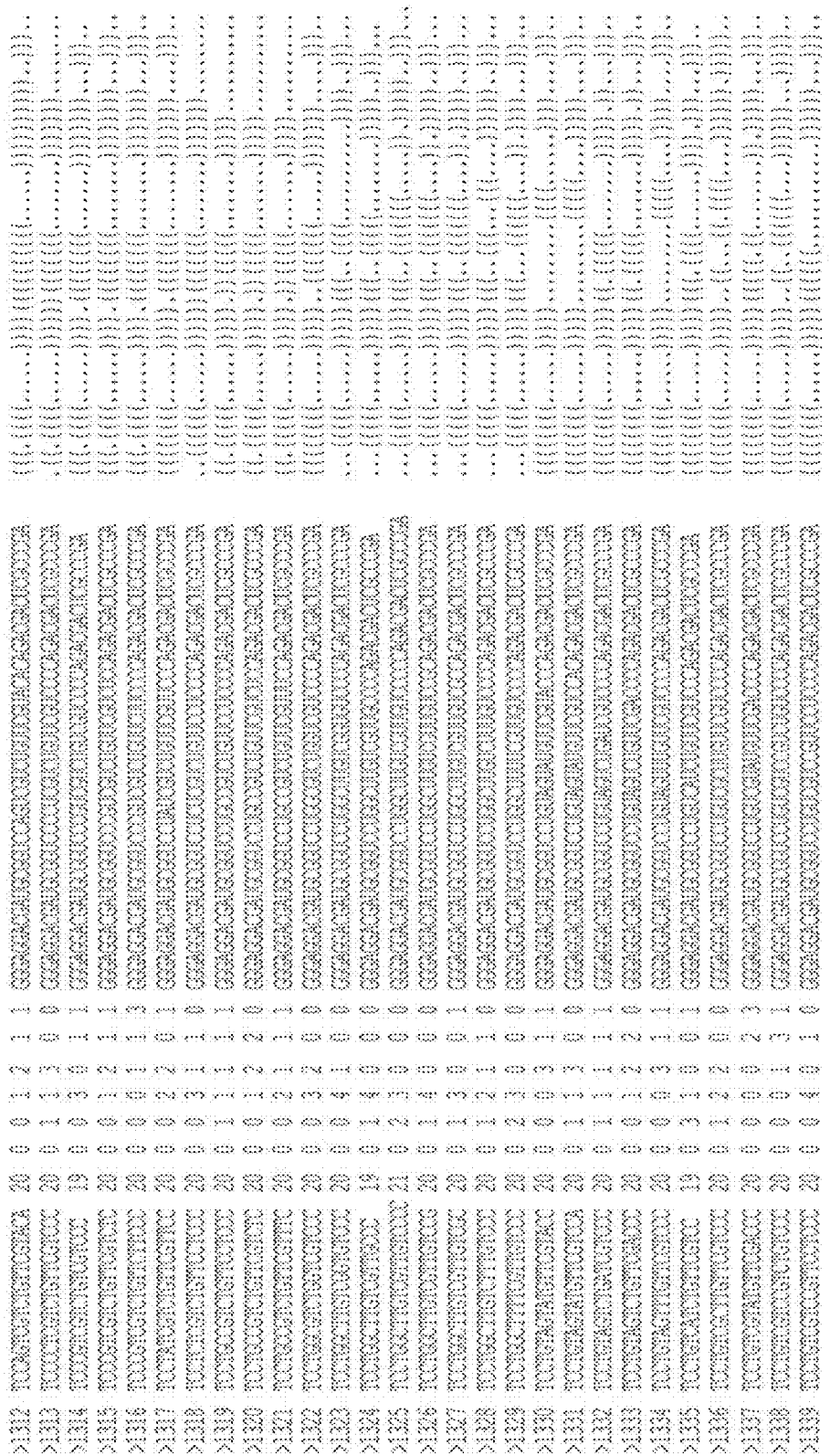

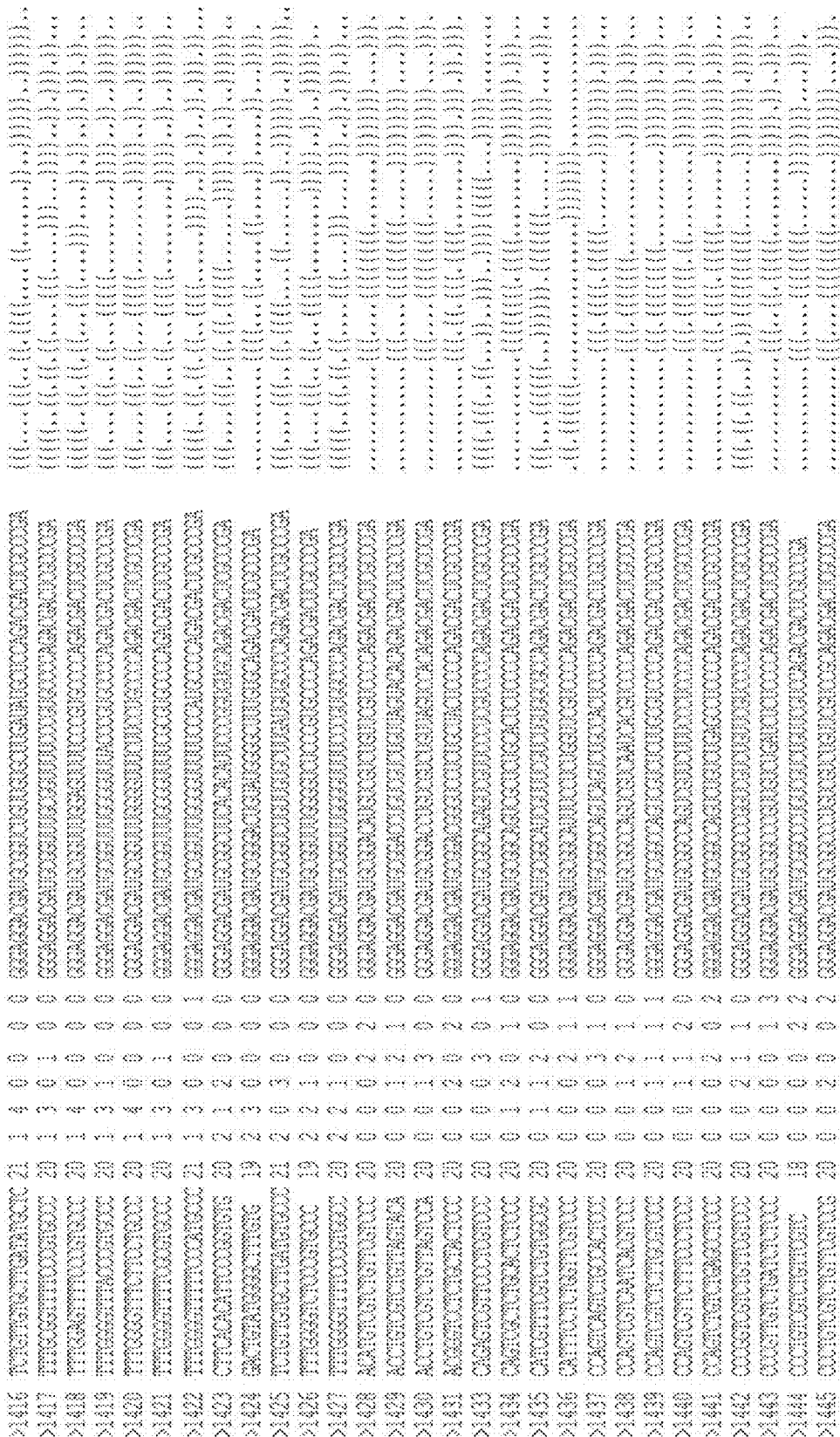

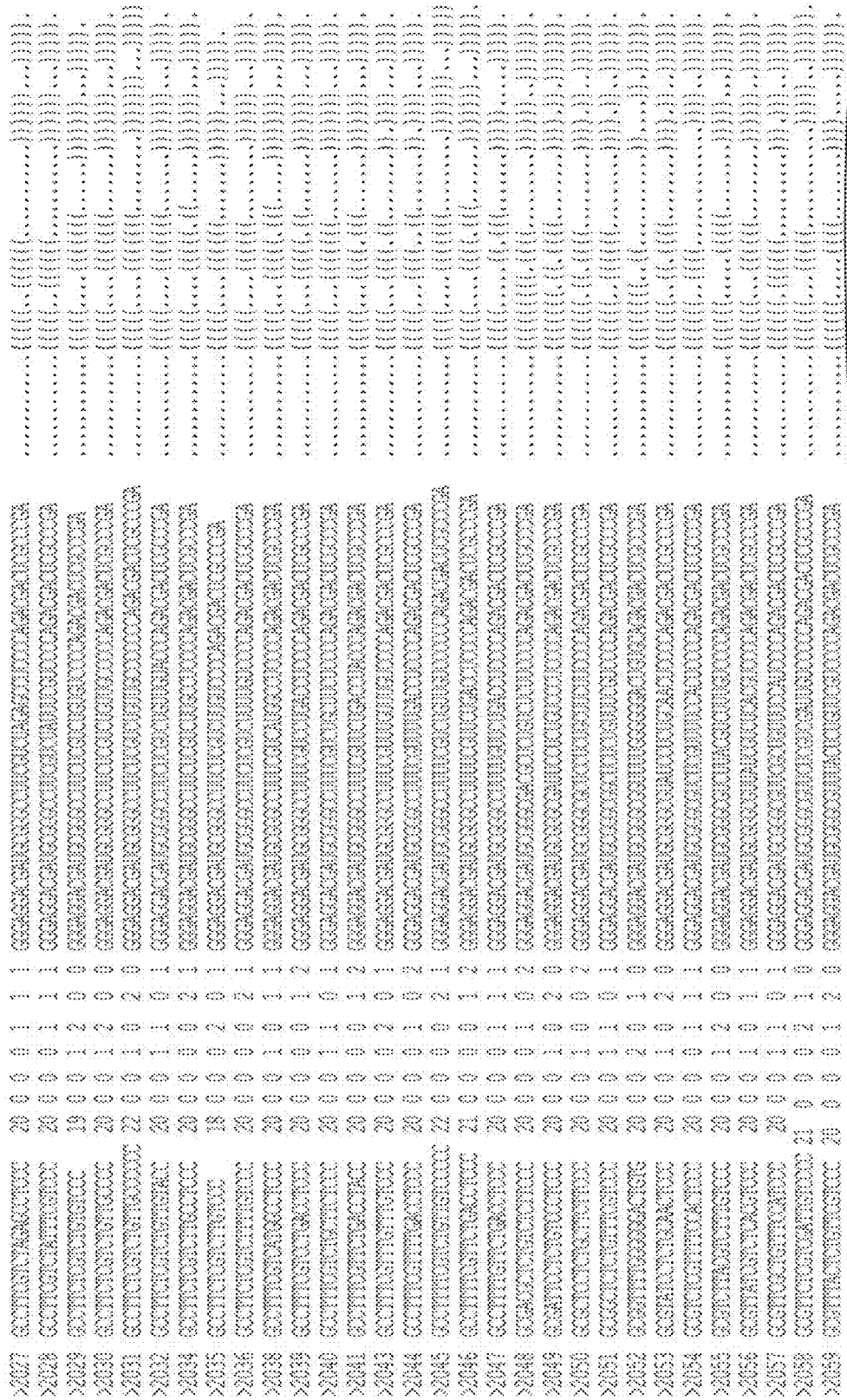

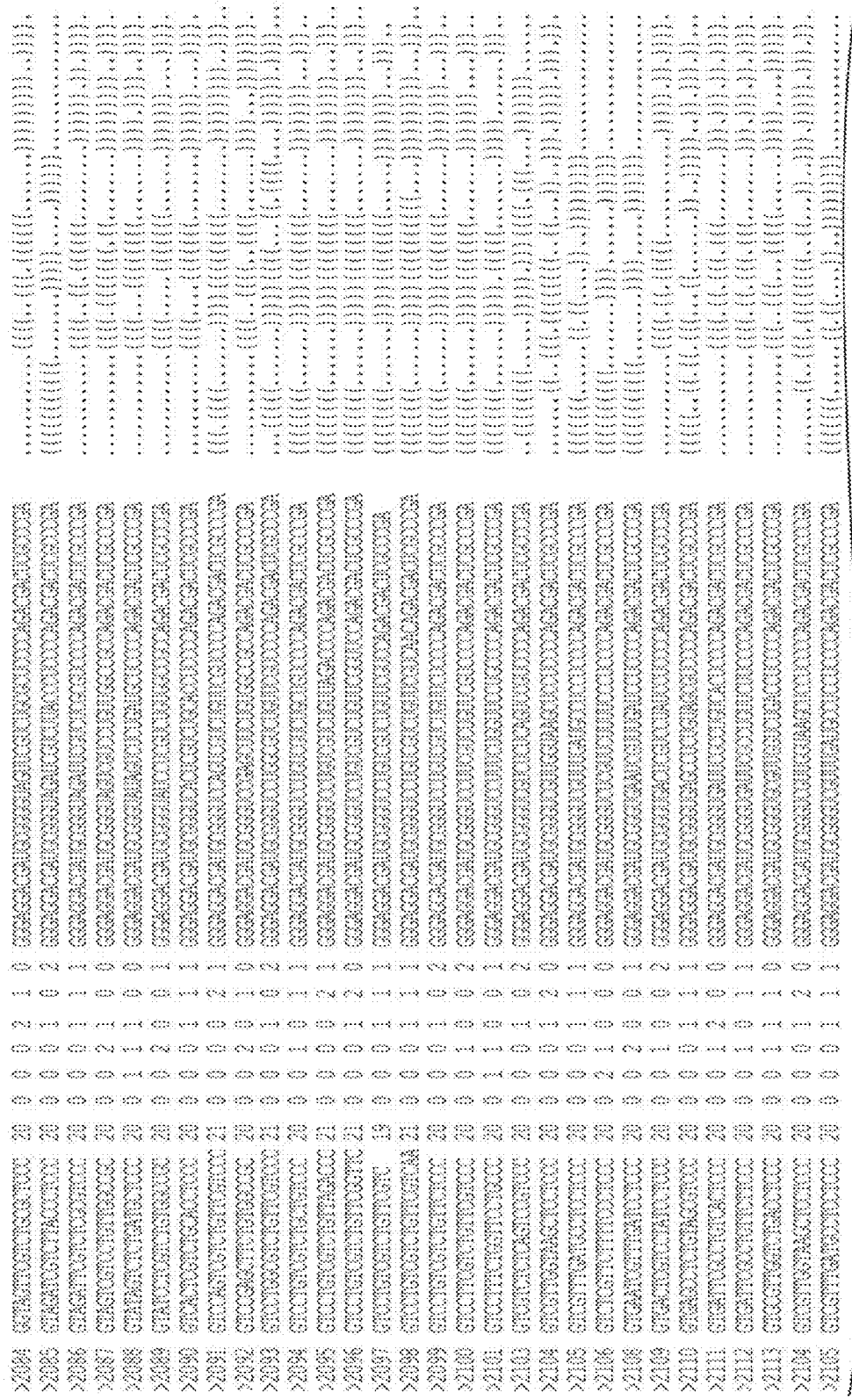

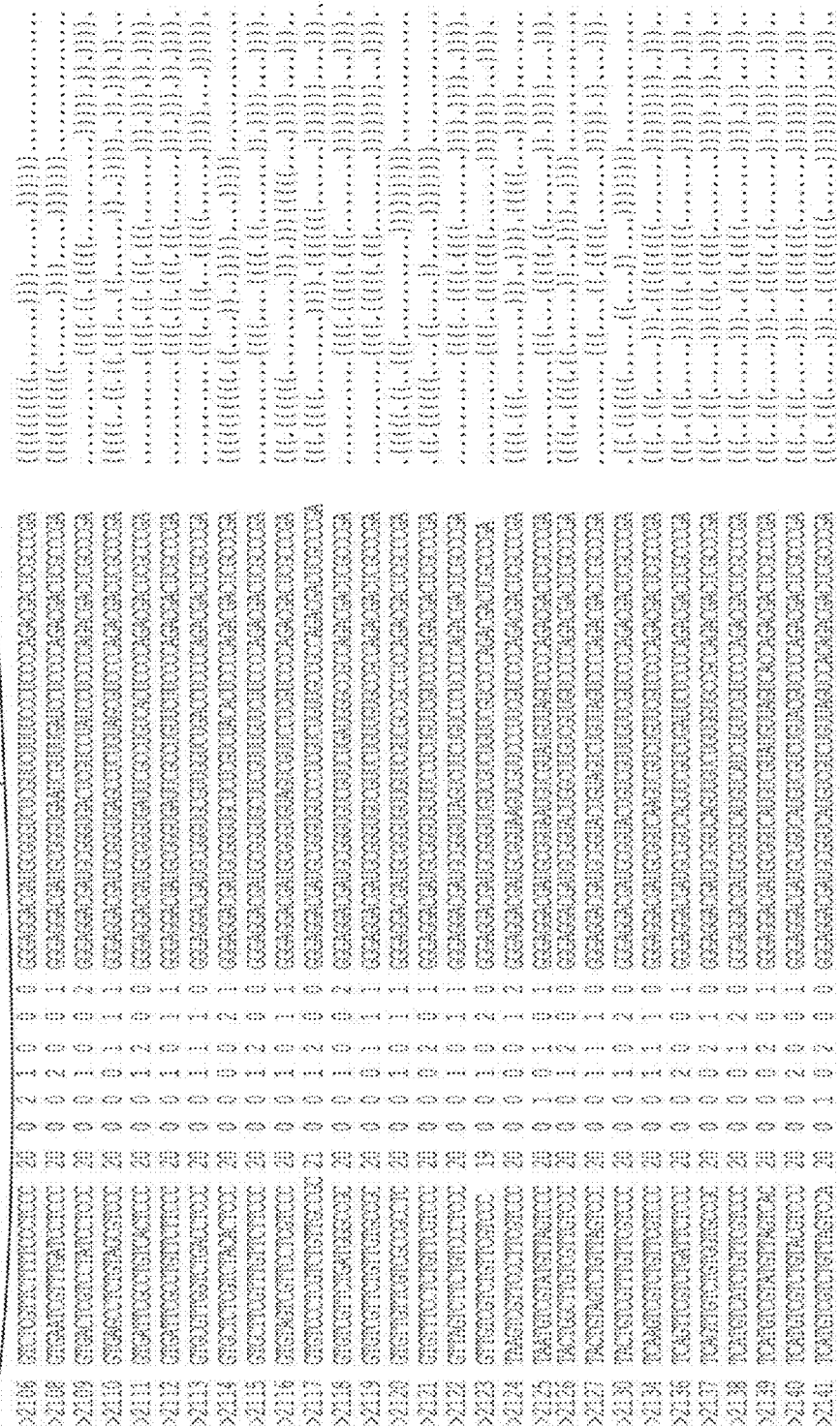

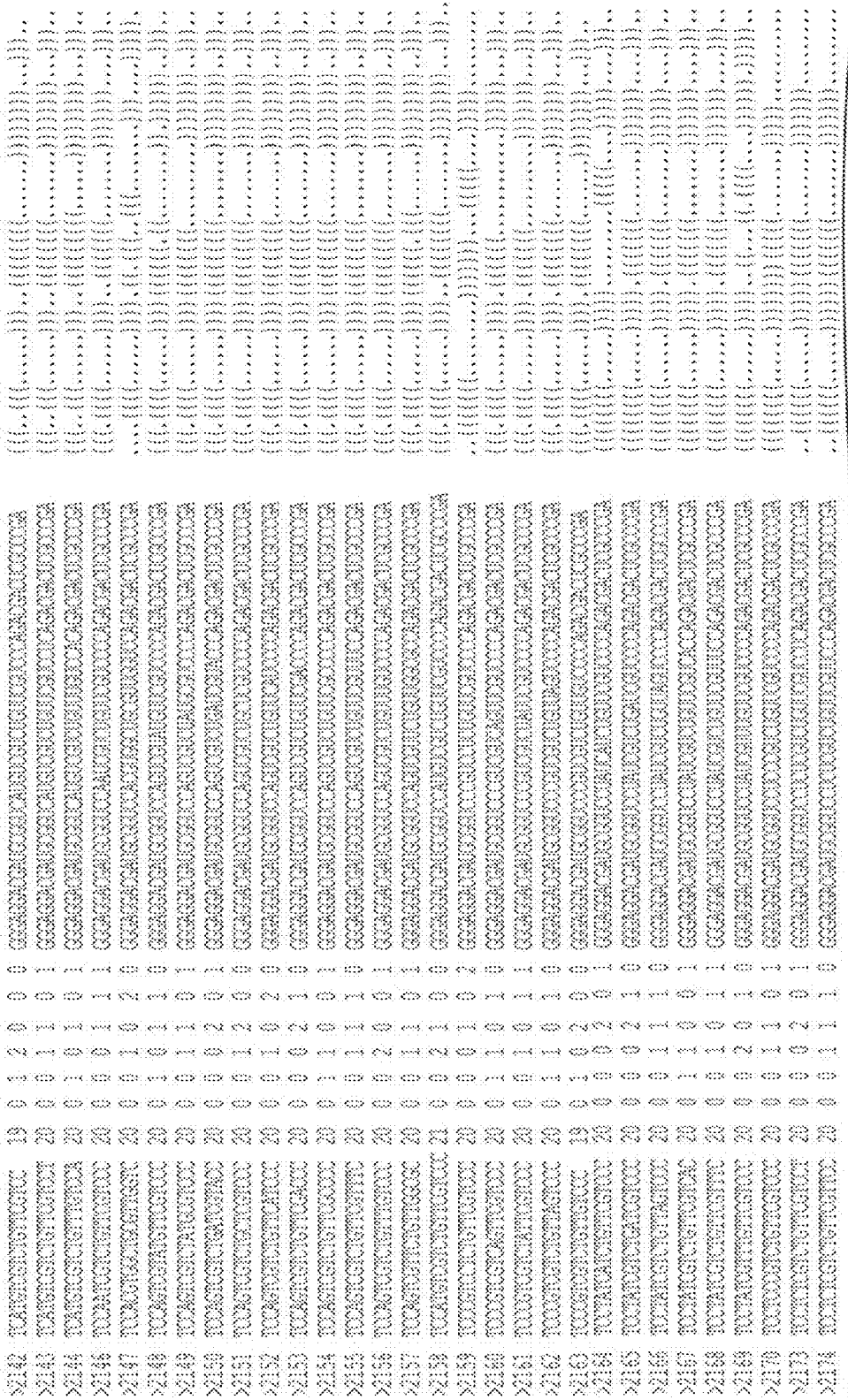

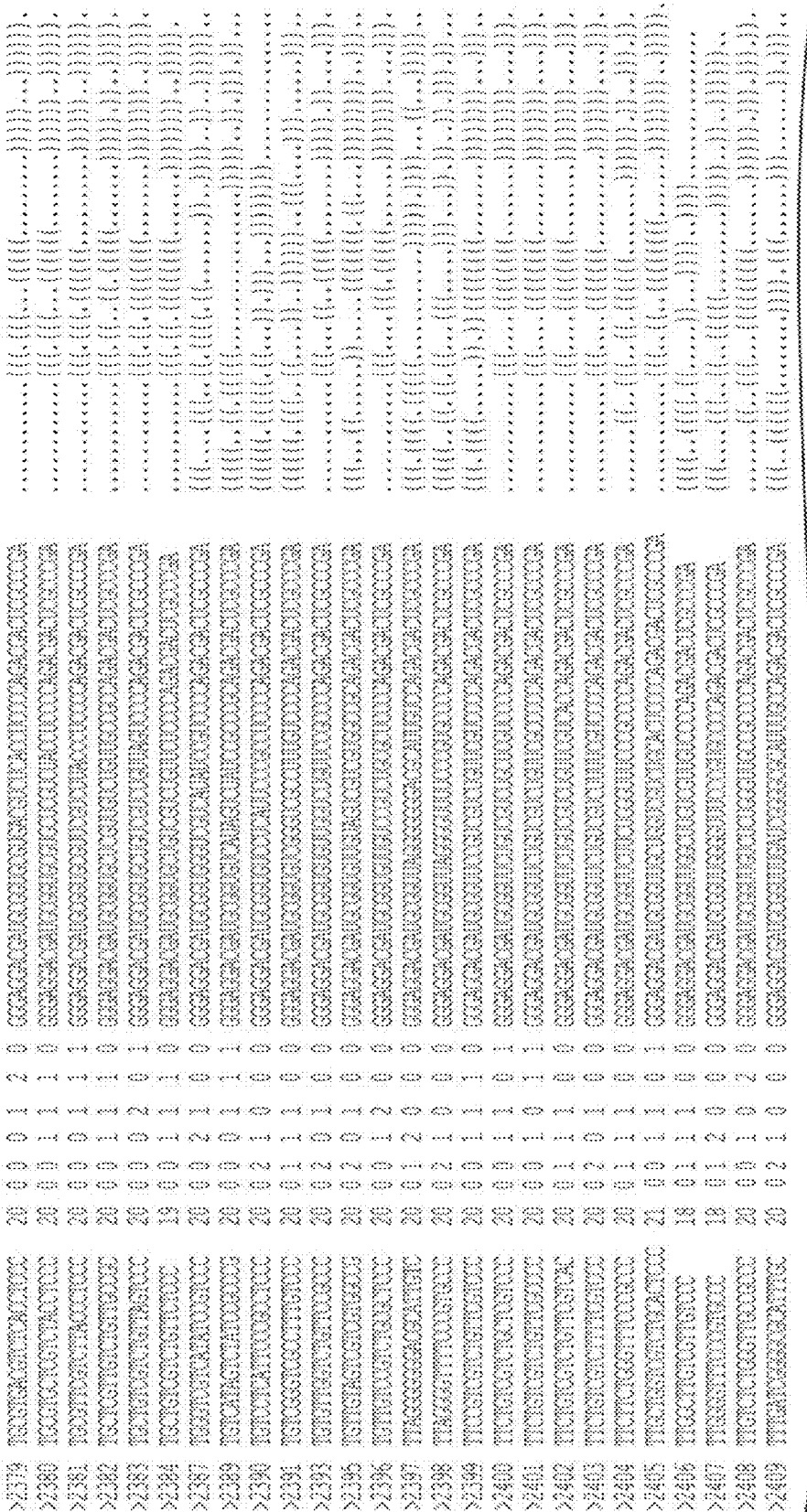

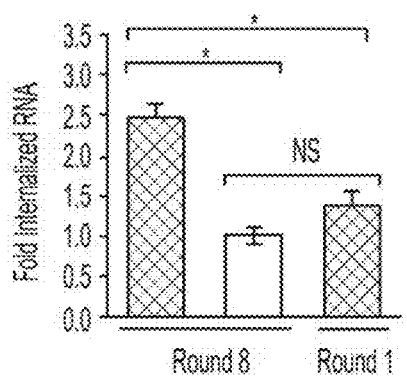
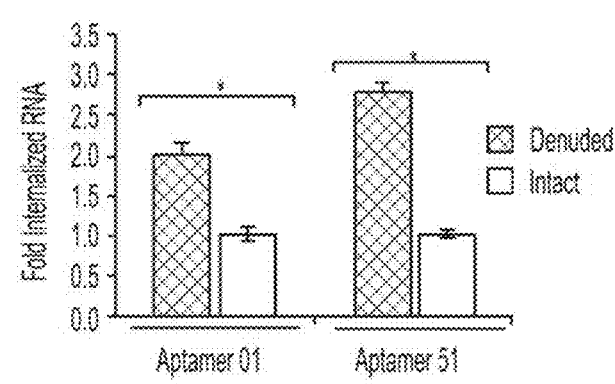
FIG. 13A  FIG. 13B
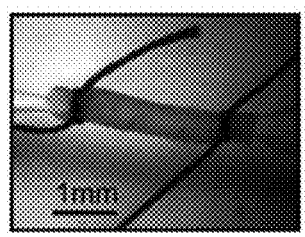
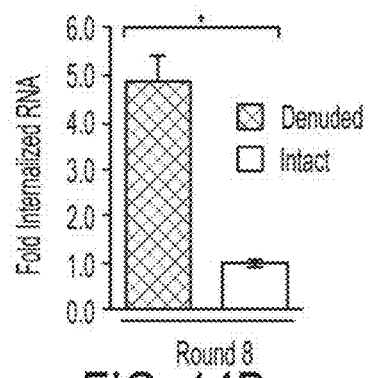
FIG. 14A  FIG. 14B

NUCLEIC ACID APTAMERS

RELATED APPLICATIONS

This patent application is a divisional application of U.S. application Ser. No. 14/829,451, filed Aug. 18, 2015, which is a divisional application of U.S. application Ser. No. 13/964,904, filed Aug. 12, 2013, which issued as U.S. Pat. No. 9,139,835 on Sep. 22, 2015, which claims the benefit of priority of U.S. Application Ser. No. 61/682,055, filed Aug. 10, 2012, and U.S. Application Ser. No. 61/792,723, filed Mar. 15, 2013, which applications are incorporated by reference herein.

FEDERAL GRANT SUPPORT

This invention was made with government support under CA138503 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 19, 2013, is named 17023.129US1_SL.txt and is 1,105,607 bytes in size.

BACKGROUND OF THE INVENTION

Vascular stenosis is a narrowing or stricture on the interior portion of the blood vessel wall, usually caused by atherosclerosis. This narrowing can progress in a generally asymptomatic manner slowly through the course of an individual's life. However, if a segment of the built-up plaque that contributed to the stenosis breaks off it can initiate a series of events that cause heart attack or stroke. Alternatively, progressive narrowing of the vessel can lead to tissue ischemia.

When stenosis is diagnosed (usually in cases of angina), patients may receive a surgically-implanted stent, which is a very small tube shaped device with a firm or hard-walled structure. This device is implanted at the site of the plaque build-up to hold the artery open and prevent the plaque build-up from being symptomatic.

Experience has shown, however, that stenting itself often promotes restenosis. In other words, during the healing process, migration and fibrosis of vascular smooth muscle cells (VSMCs) can be stimulated, resulting in growth of the cells around the stent, thus creating an issue similar to the original one which called for stenting in the first place. In order to prevent this, advanced stents have been impregnated with drugs (drug eluting stent or DES) to limit the occurrence of restenosis from fibrosis or clot formation. DES that have been approved for use in the clinic elute drugs such as sirolimus, paclitaxel, everolimus in low doses into the stent microenvironment to prevent unwanted cell migration or proliferation during the initial stages of the healing process.

The therapeutic agents used in drug eluting stents are generally antiproliferative agents. In other words, they are equally effective at preventing replication of all the cell types in the microenvironment of the stent. However, the patient needs to produce endothelial cells along the surface of their arteries to prevent the spontaneous activation of platelets and the formation of clots. This event is currently prevented during the recovery period by treating the patient with system antithrombic agents ("blood thinners"), which can instigate their own issues in the patient population. Thus, there is an on-going need for drug-eluting stents that are impregnated with therapeutics that preferentially eliminate the migration and proliferation of VSMCs and allow the post-surgery regrowth of vascular endothelial cells, so that patient recovery is quicker and the prognosis is better. There is also a need for compositions and methods for local delivery of therapeutic compounds into the vascular wall or for intra-venous/intra-arterial delivery.

SUMMARY OF THE INVENTION

Certain embodiments of the present invention provide a nucleic acid molecule not more than 100 nucleotides in length (e.g., 50-90 nt) comprising any one of the aptamers listed in FIGS. 12-1A through 12-47. In certain embodiments, the aptamer is aptamer-1, aptamer-2, aptamer-3, aptamer-4, aptamer-5, aptamer-6, aptamer-8, aptamer-9, aptamer-11, aptamer-13, aptamer-14, aptamer-15, aptamer-17, aptamer-19, aptamer-21, aptamer-23, aptamer-26, aptamer-27, aptamer-28, aptamer-29, aptamer-35, aptamer-36, aptamer-41, aptamer-51, aptamer-53, aptamer-55, aptamer-58, aptamer-62, aptamer-71, aptamer-81, aptamer-89, aptamer-229, or aptamer-420. In certain embodiments, the nucleotides are RNA. In certain embodiments, the nucleic acid of the present invention is DNA. In certain embodiments, the RNA includes a modified nucleotide. In certain embodiments, the RNA is chemically modified (2'-fluoropyridines).

Certain embodiments of the present invention provide a conjugate comprising the nucleic acid molecule described above linked to a therapeutic or diagnostic molecule. In certain embodiments, the therapeutic molecule is an RNAi molecule. In certain embodiments, the RNAi molecule is an siRNA molecule or an miRNA molecule. In certain embodiments, "linked" includes directly linking (covalently or non-covalently binding) the nucleic acid molecule of the invention (e.g., an aptamer) to a therapeutic or diagnostic molecule. In certain embodiments, "linked" includes linking the nucleic acid molecule of the invention (e.g., an aptamer) to a therapeutic or diagnostic molecule using a linker, e.g., a nucleotide linker, e.g., the nucleotide sequence "AA" or "TT" or "UU".

Certain embodiments of the present invention provide a method for delivering a therapeutic or diagnostic molecule to a vascular smooth muscle cell, comprising contacting the cell with the conjugate described above.

Certain embodiments of the present invention provide a pharmaceutical composition comprising a molecule or conjugate as described above and a pharmaceutically acceptable carrier.

Certain embodiments of the present invention provide a method for treating a patient having vascular disease comprising administering a molecule or conjugate as described above to the patient.

Certain embodiments of the present invention provide a use of a molecule or conjugate as described above for treating vascular disease.

Certain embodiments of the present invention provide a method for treating a patient having or being disposed to having vascular stenosis or restenosis comprising administering a molecule or conjugate as described above to the patient.

Certain embodiments of the present invention provide a molecule or conjugate as described above for use in therapy.

Certain embodiments of the present invention provide a molecule or conjugate as described above for use in the prophylactic or therapeutic treatment of vascular disease.

Certain embodiments of the present invention provide an article of manufacture comprising a solid substrate coated with the molecule or conjugate as described above. In certain embodiments, the solid substrate is a stent, catheter, a catheter hub, a catheter port, or a non-degradable implant.

Certain embodiments of the present invention provide a method of isolating cell-internalized RNA comprising:

(a) contacting an initial RNA pool, consisting of RNA sequences derived from a duplex DNA library using in vitro transcription, with a non-target cell to generate unbound RNA and bound RNA and remove the bound RNA;

(b) contacting the unbound RNA with a target cell to generate cell-bound RNA, cell-unbound RNA, and cell-internalized RNA;

(c) wash the target cell with a stringent salt solution; and (d) isolate the cell-internalized RNA, wherein RNA in the RNA pool is not more than 90 nucleotides in length. The RNA pool can vary in length (e.g., 50-90 nt). The RNAs in the pool contain a central region of unique sequence of about 15-25 nucleotides (such as 20 nucleotides) flanked by constant sequence regions of about 10-20 nucleotides (such as about 15 or 16 nucleotides).

In certain embodiments, the method further comprises (e) reverse transcribing and PCR amplifying the cell-internalized RNA to generate a secondary RNA pool.

In certain embodiments, the method further comprises (f) obtaining a sample from the secondary RNA pool, (g) performing high throughput sequencing (HTS) to obtain raw reads of unique sequences and non-unique sequences, (h) filtering the raw reads based on RNA library constant region sequences to obtain filtered reads, (i) determining which filtered reads are selected sequences and which are non-selected sequences, and (j) analyzing a database of selected sequences for candidate sequences by calculating the fold enrichment of HTS reads between two rounds of selection. In certain embodiments, fold enrichment two rounds of selection that are analyzed is a comparison of the fold enrichment of round 3 to round 8.

As used herein, the term "selected sequences" are sequences enriched by the SELEX process, and "non-selected sequences" are background sequences indicative of the unenriched starting RNA pool. In certain embodiments, the 5'constant sequence is HTS DNA sequence=5'-GGGAG-GACGATGCGG-3' (SEQ ID NO: 1); and the 3' constant sequence is HTS DNA sequence=5'-CAGACGACTCGC-CCGA-3' (SEQ ID NO: 2). In certain embodiments, the present invention provides a method of identifying a true-selected sequence by obtaining the number of times a unique sequence appears in each round of selection (cluster size), wherein true-selected sequence is a unique sequence that appears in at least three rounds of selection.

In certain embodiments, the present invention provides a method of identifying a true-selected sequence by comparing the unique sequences of different rounds of selection, and identifying a unique sequence present in at least two rounds of selection. A "unique sequence" is defined as each individual sequence is a sequence different from all other unique sequences. As used herein the term "total sequences" is defined as the number of HTS reads for a given unique sequence. As used herein a "round of selection" is a process involving steps (a)-(i). In certain embodiments, the method further comprising obtaining the number of times a unique sequence appeared in each round of selection. In certain embodiments, the method further comprises determining the edit distance of the unique sequences as compared to the other sequences in the round of selection. Edit as defined by the Vienna Package edit distance is the "minimum sum of the costs along an edit path converting one object into the other" (costs=insertion, deletion and replacement). The edit distance is the number of changes (substitution/insertion/deletion) necessary for two sequences to become identical. For example, closely-related sequences have a low edit distance, while unrelated or loosely-related sequences are denoted by a high edit distance.

In certain embodiments, the method further comprises determining the tree distance of the unique sequences as compared to the other sequences in the round of selection. Tree distance as defined by the Vienna Package tree distance uses the same cost calculations (cost=insertion, deletion and replacement) but takes into account the bracket pairing of the predicted RNA structure when determining the minimum sum of costs to convert one object into the other. "Tree distance" describes the relatedness of two structures by calculating the dissimilarity between two structures. Analogous with edit distance, closely-related structures have a low tree distance, while unrelated or loosely-related structures are denoted by a large tree distance. In certain embodiments, the present invention provides an aptamer having a true-selected sequence present in at least two rounds of selection, having a cluster size of at least 3, having an edit distance of 1, and having a tree distance of less than 3.

The present invention further provides a nucleic acid coding molecule encoding a nucleic acid aptamer molecule as described above. The present invention further provides an expression cassette comprising the nucleic acid coding molecule described above. In certain embodiments, the expression cassette further includes a promoter, such as a regulatable promoter or a constitutive promoter. Examples of suitable promoters include a CMV, RSV, pol II or pol III promoter. The expression cassette may further contain a polyadenylation signal (such as a synthetic minimal polyadenylation signal) and/or a marker gene. Examples of marker genes include visual markers such as GFP, or functional markers, such as antibiotic resistance genes.

In certain embodiments, the expression cassette is contained in a vector, such as a viral vector or a plasmid vector. Certain embodiments of the invention provide a vector, e.g., a viral vector, including at least one (e.g., 1 or 2) expression cassette of the invention. Examples of appropriate vectors include adenoviral, lentiviral, adeno-associated viral (AAV), poliovirus, HSV, or murine Maloney-based viral vectors. In one embodiment, the vector is an adenoviral vector. In certain embodiments, a vector may contain two expression cassettes.

Certain embodiments of the invention provide an isolated or non-human cell including the PMSA receptor and a molecule or conjugate of the invention. The present invention relates to a specific delivery of siRNAs and one that, at least in one embodiment, only uses properties of RNA. The delivery method of the instant invention exploits the structural potential of nucleic acids (e.g., RNA) to target siRNAs to a particular cell-surface receptor and thus to a specific cell type. In one embodiment, the invention provides a method and compositions to specifically deliver nucleic acids that comprise both a targeting moiety (e.g., an aptamer) and an RNA-silencing moiety (e.g., an siRNA) that is recognized and processed by Dicer in a manner similar to the processing of microRNAs. Aptamers and siRNAs have low immunogenicity. They can easily be synthesized in large quantities at a relatively low cost and are amendable to a variety of chemical modifications that confer both resistance to degradation and improved pharmacokinetics in vivo. The smaller size of aptamers compared with that of antibodies (<15 kDa versus 150 kDa) facilitates their in vivo delivery by promoting better tissue penetration.

In certain embodiments of the invention, RNAi molecules are employed to inhibit expression of a target gene. By "inhibit expression" is meant to reduce, diminish or suppress expression of a target gene. Expression of a target gene may be inhibited via "gene silencing." Gene silencing refers to the suppression of gene expression, e.g., transgene, heterologous gene and/or endogenous gene expression, which may be mediated through processes that affect transcription and/or through processes that affect post-transcriptional mechanisms. In some embodiments, gene silencing occurs when an RNAi molecule initiates the degradation of the mRNA transcribed from a gene of interest in a sequence-specific manner via RNA interference, thereby preventing translation of the gene's product.

As used herein the term "encoded by" is used in a broad sense, similar to the term "comprising" in patent terminology. For example, the statement "the first strand of RNA is encoded by SEQ ID NO:1" means that the first strand of RNA sequence corresponds to the RNA sequence transcribed from the DNA sequence indicated in SEQ ID NO:1, but may also contain additional nucleotides at either the 3' end or at the 5' end of the RNA molecule.

The reference to siRNAs herein is meant to include short hairpin RNAs (shRNAs) and other small RNAs that can or are capable of modulating the expression of a target gene, for example via RNA interference. Such small RNAs include without limitation, shRNAs and miroRNAs (miRNAs). The two strands of RNA in the siRNA may be completely complementary, or one or the other of the strands may have an "overhang region" (i.e., a portion of the RNA that does not bind with the second strand). Such an overhang region may be from 1 to 10 nucleotides in length.

This invention relates to compounds, compositions, and methods useful for inhibiting a target gene expression using short interfering nucleic acid (siRNA) molecules. This invention also relates to compounds, compositions, and methods useful for modulating the expression and activity of the target gene by RNA interference (RNAi) using small nucleic acid molecules. In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the expression of target genes. A siRNA of the instant invention can be chemically synthesized, expressed from a vector or enzymatically synthesized.

In the present invention, an expression cassette may contain a nucleic acid encoding at least one strand of the RNA duplex described above. Such an expression cassette may further contain a promoter. The expression cassette may be contained in a vector. These cassettes and vectors may be contained in a cell, such as a mammalian cell. A non-human mammal may contain the cassette or vector. The vector may contain two expression cassettes, the first expression cassette containing a nucleic acid encoding the first strand of the RNA duplex, and a second expression cassette containing a nucleic acid encoding the second strand of the RNA duplex.

The present invention further provides a method of substantially silencing a target gene of interest or targeted allele for the gene of interest in order to provide a therapeutic effect. As used herein the term "substantially silencing" or "substantially silenced" refers to decreasing, reducing, or inhibiting the expression of the target gene or target allele by at least about 5%, 10%, 15%, 20%, 25%, 30%, 35%, 40%, 45%, 50%, 55%, 60%, 65%, 70%, 75%, 80%, 85% to 100%. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effect can be measured quantitatively by a physician or qualitatively by a patient afflicted with the disease state targeted by the siRNA. In certain embodiments wherein both the mutant and wild type allele are substantially silenced, the term therapeutic effect defines a condition in which silencing of the wild type allele's expression does not have a deleterious or harmful effect on normal functions such that the patient would not have a therapeutic effect.

In one embodiment, the expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional sequences, such as sequences encoding an aptamer and/or siRNA.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available from, e.g., Stratagene® (San Diego, Calif.).

In one embodiment, pharmaceutical compositions will comprise sufficient genetic material to produce a therapeutically effective amount of the siRNA of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

BRIEF DESCRIPTION OF DRAWINGS

FIGS. 1A-1E. Cell-Internalization SELEX (systematic evolution of ligands by exponential enrichment). (A) Schematic of the methodology used to isolate aptamers that specifically internalize into vascular smooth muscle cells (VSMCs; target). Eight rounds of selection were performed to enrich for RNA aptamer sequences that selectively internalizes into the target VSMCs. Non-specific aptamers were removed by pre-clearing against endothelial cells (ECs; non-target). (B-D) Progression of the selection and complexity of the RNA pools was monitored using a DNA melt assay at (B) rounds 0-3, (C) rounds 3-6 and (D) rounds 6-8. (E) The RNA pools at each round of selection were tested for internalization into VSMCs and ECs using quantitative RT-PCR (RT-qPCR). These data were normalized to an internal RNA reference control for the PCR and to cell number.

FIGS. 2A-2E. Assessment of selection progression. (A) RNA aptamer pools from rounds 0, 1, 3, 5, 6, 7 and 8 were sequenced using Illumina sequencing technology. The number of unique reads (black squares) and total reads (white squares) was determined at each round of selection. (B) % Enrichment at each round (black circle) was determined by the formula (% Enrichment=1-Unique/Total). A sigmoidal curve fit was used to determine the round at which 50% sequence enrichment was achieved (white circle). The average (C) minimum free energy (D) ensemble probability and (E) ensemble diversity at each selection round was calculated for the unique reads (black squares) and for the total reads (white squares) using RNAfold secondary structure prediction algorithm.

FIGS. 12-1A through 12-47. Excel/CVS Data File 1: Excel data file includes all unique selected sequences. Column label identifiers:
(#)=identification number
(Representatives)=selected RNA aptamer representatives (X)
(HTS read variable region)=variable region identified by HTS (SEQ ID NOS 10-2321, respectively, in order of appearance)
(Length)=nucleotide length of the variable region
(1)=number of reads in round 1
(3)=number of reads in round 3
(5)=number of reads in round 5
(6)=number of reads in round 6
(7)=number of reads in round 7
(8)=number of reads in round 8
(RNA)=RNA aptamer sequence (variable region with 5' and 3' constant regions) (SEQ ID NOS 2322-4633, respectively, in order of appearance)
(Structure)=predicted secondary structure of the RNA aptamer sequence.

FIGS. 13A-13B: Ex vivo VSMC aptamer internalization. Rat aortic segments with either denuded or intact endothelium were exposed to A) enriched (Round 8), an un-enriched round (Round 1) of aptamers or B) our previously identified VSMC-specific aptamers. Non-internalized aptamer was removed by high salt wash and internalized aptamer, recovered by TRIzol extraction and measured by RT-qPCR. ($*p<0.05$).

FIGS. 14A-14B: Perfused vessel ex vivo VSMC aptamer internalization. A) Rat arterial vessel segments (carotid/femoral) with either denuded or intact endothelium were perfused with B) enriched (Round 8) aptamers. Non-internalized aptamer was removed by high salt wash and internalized aptamer, recovered by TRIzol extraction and measured by RT-qPCR.($*p<0.05$)

FIGS. 16A-16-C: Ex vivo aptamer internalization into human pulmonary artery segments. Segments of human pulmonary artery were denuded and exposed to control aptamer or A) aptamer 01, B) aptamer 14, C) aptamer 51. Non-internalized aptamer was removed by high salt wash and internalized aptamer, recovered by TRIzol extraction and measured by RT-qPCR. ($**p<<0.05$; $*p<0.5$)

FIG. 19: Aptamer 51 siRNA chimera internalization. Aptamer 51 aptamer-siRNA chimeras (#1 and #2) internalized as well as aptamer 51 alone. Non-internalized aptamer or aptamer chimera was removed by high salt wash and internalized aptamer or aptamer chimera, recovered by TRIzol extraction and measured by RT-qPCR.

FIG. 20: Aptamers are specific for vascular smooth muscle over muscle types. Aptamers (150 nM) were incubated with tissue segments ex vivo for 30 min and recovered RNA measured by RT-qPCR. Data were normalized to tissue mass and expressed relative to denuded aorta.

DETAILED DESCRIPTION OF THE INVENTION

Figure 3A:
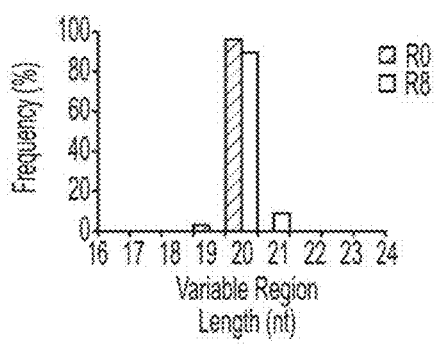
FIGS. 3A-3C. Bioinformatics analysis of high-throughput sequence data from selection rounds. (A) The RNA sequences from rounds 0 (gray bars) and 8 (black bars) of selection were examined for frequency of variable region nucleotide (nt) length (ranging from 16 nt-24 nt). (B) Number of unique reads from round 0 (gray circles) and rounds 1-8 (black circles) vs. number of rounds sequenced. (C) Number of unique reads from round 0 (gray circles) and rounds 1-8 (black circles) vs. cluster size. A single sequence (▼) containing a string of cytosine was found 30 times within round 0.

Vascular revascularization by stenting is associated with restenosis due to proliferation of vascular smooth muscle cells (VSMCs) and intimal hyperplasia. Although the use of cell cycle inhibitors in drug eluting stents (DES) has reduced the rate of in-stent restenosis, this approach also inhibits re-endothelialization, thereby requiring prolonged antithrombotic regimens to prevent stent thrombosis. Delivery of nucleic acid aptamers by DES is a new approach due to their high specific binding affinity and potential for modification by medicinal chemistry. We have identified RNA aptamers that (1) internalize into VSMCs and/or (2) specifically inhibit VSMC activation. Using an in vivo compatible RNA aptamer library, VSMC-specific aptamers were selected using a cell-internalization SELEX (systematic evolution of ligands by exponential enrichment) process with iterative rounds of positive selection using VSMCs and ECs. Specificity of these aptamers was confirmed by ex vivo studies that demonstrated preferential internalization into denuded, but not endothelium-intact, artic segments. In addition, several of the VSMC-targeting aptamers exhibited differential effectiveness in inhibiting VSMC migration as measured by Boyden chamber assays. In delivery studies, we next engineered aptamer-siRNA chimeras using siRNAs targeting Nx1 NADPH oxidase, which has been implicated in intimal hyperplasia. These VSMC-targeting aptamer-siRNA chimeras retain specificity for VSMCs and are being evaluated for efficacy in reducing intimal formation in a murine model of vascular injury. Thus, we developed novel VSMC-targeting aptamers that may serve as a platform technology to selective deliver therapeutics to VSMCs over ECs. The aptamers that inhibited cell migration present an opportunity for dual-action VSMC-targeted therapeutic agents.

The present technology is a series of RNA constructs that have been created to specifically inhibit the migration and proliferation of VSMCs. Several constructs have been created which likely bind to a diverse set of cell surface receptors on VSMC (with 20-fold greater specificity than binding to endothelial cells). Initial studies have demonstrated that these aptamers not only bind to, but also inhibit the migration of the VSMCs when used alone. However, the targeting aptamers can also be linked to RNAi molecules that target the production of proteins necessary for intimal hyperplastic growth, such as Nox1 NADPH oxidase. These are VSMC-targeting aptamers, some of which may have growth retarding effects themselves that can be paired with RNAi to inhibit the expression of any target protein within VSMCs. In certain embodiments, the constructs are chemically modified (2'-fluoropyridines) RNA constructs making them nuclease resistant. See WO 2010/019446, which is incorporated by reference in its entirety.

Aptamer Portion

Aptamers are single stranded oligonucleotides that can naturally fold into different 3-dimensional structures, which have the capability of binding specifically to biosurfaces, a target compound or a moiety. The term "conformational change" refers to the process by which a nucleic acid, such as an aptamer, adopts a different secondary or tertiary structure. The term "fold" may be substituted for conformational change.

Aptamers have advantages over more traditional affinity molecules such as antibodies in that they are very stable, can be easily synthesized, and can be chemically manipulated with relative ease. Aptamer synthesis is potentially far cheaper and reproducible than antibody-based diagnostic tests. Aptamers are produced by solid phase chemical synthesis, an accurate and reproducible process with consistency among production batches. An aptamer can be produced in large quantities by polymerase chain reaction (PCR) and once the sequence is known, can be assembled from individual naturally occurring nucleotides and/or synthetic nucleotides. Aptamers are stable to long-term storage at room temperature, and, if denatured, aptamers can easily be renatured, a feature not shared by antibodies. Furthermore, aptamers have the potential to measure concentrations of ligand in orders of magnitude lower (parts per trillion or even quadrillion) than those antibody-based diagnostic tests. These characteristics of aptamers make them attractive for diagnostic applications.

Aptamers are typically oligonucleotides that may be single stranded oligodeoxynucleotides, oligoribonucleotides, or modified oligodeoxynucleotide or oligoribonucleotides. The term "modified" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2-azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include, by example and not by way of limitation, alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2-methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; 1-methylcytosine.

The aptamers of the invention are synthesized using conventional phosphodiester linked nucleotides and synthesized using standard solid or solution phase synthesis techniques which are known in the art. Linkages between nucleotides may use alternative linking molecules. For example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

In certain embodiments of the present invention, the aptamer portion is specific for vascular smooth muscle cells (VSCMs). In certain embodiments, the aptamers of the present invention are taken up by the VSCMs. In certain embodiments, additional modifications are made to the aptamer portion. Additional modifications to the aptamer portion include 2'O-methyl modification of the pyrimidines. In other embodiments, all of the nucleotides in the aptamer are 2'O-methyl modified. Alternatively, the pyrimidines, or all the nucleotides, may be modified with 2'fluoros (both pyrimidines and purines). Additional modifications to the nucleotides in the aptamer include large molecular weight conjugates like pegylation, lipid-based modifications (e.g., cholesterol) or nanoparticles (e.g., PEI or chitosan) to improve the pharmacokinetic/dynamic profile of the chimera.

Small Molecule Portion

The aptamers of the present invention can be operably linked to one or more small molecule entities. In certain embodiments, the entity is a fluorescent tag, affinity tag, a protein, a solid substrate, a cell surface, or a cellular component. In certain embodiments, the cellular component is a cell wall or cell membrane. In certain embodiments, the solid substrate is a component of silica, cellulose, cellulose acetate, nitrocellulose, nylon, polyester, polyethersulfone, polyolefin, or polyvinylidene fluoride, or combinations thereof. In certain embodiments, the solid substrate is a stent or other medical device, filter, magnetic bead, metal oxide, latex particle, microtiter plates, polystyrene bead, or CD-ROM.

In certain embodiments, the aptamer is linked to the entity by means of a linker. In certain embodiments, the linker is a binding pair. In certain embodiments, the "binding pair" refers to two molecules which interact with each other through any of a variety of molecular forces including, for example, ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-avidin, hormone-receptor, receptor-ligand, enzyme-substrate, IgG-protein A, antigen-antibody, and the like. In certain embodiments, a first member of the binding pair comprises avidin or streptavidin and a second member of the binding pair comprises biotin. In certain embodiments, the aptamer is linked to the entity by means of a covalent bond.

The entity, for example, may additionally or alternatively, be a detection means. A number of "molecular beacons" (such as fluorescence compounds) can be attached to aptamers to provide a means for signaling the presence of and quantifying a target chemical or biological agent. Other exemplary detection labels that could be attached to the aptamers include biotin, any fluorescent dye or tracer, amine modification, horseradish peroxidase, alkaline phosphatase, etc.

In certain embodiments, the aptamer is operably linked to a detection means and to a solid substrate. For example, the aptamer may be linked to a fluorescent dye and to a magnetic bead.

The small molecule portion of the ligand can be siRNA sequences, miRNAs, small molecule inhibitors, chelators for housing radionuclides (for diagnostic/imaging applications as well as development of targeted radiotherapies, see, e.g., Rockey et al., Synthesis and radiolabeling of chelator-RNA aptamer bioconjugates with copper-64 for targeted molecular imaging, *Bioorganic & Medicinal Chemistry*, 19: 4080-4090 (2011)), nanoparticles containing all of the above plus DNA vectors and/or mRNA sequences, depending on the use of the ligand as a diagnostic agent or as a therapeutic agent. In certain embodiments, the small molecule is an siRNA specific for Nox1 NADPH oxidase. In certain embodiments, the small molecule is a molecule capable of modulating cell activity, including but not limited to biologic and pharmacologic inhibitors/agonists, siRNA, or miRNA. In certain embodiments, the small molecules are biologic or pharmacoligic agents that can alter smooth muscle cell migration and/or proliferation and/or phenotypic modulation and/or changes in gene expression.

Linking Molecules

Chemistries that can be used to link molecules to the aptamer are known in the art, such as disulfide linkages, amino linkages, covalent linkages, etc. Additional linkages and modifications can be found on the world-wide-web at trilinkbiotech.com/products/oligo/oligo_modifications.asp.

Solid Substrates

In certain embodiments, the aptamer or conjugate is in contact with a solid substrate. In certain embodiments the solid substrate is a component of silica, cellulose, cellulose acetate, nitrocellulose, nylon, polyester, polyethersulfone, polyolefin, or polyvinylidene fluoride, or combinations thereof. In certain embodiments, the solid substrate is a filter, magnetic bead, metal oxide, latex particle, microtiter plates, polystyrene bead, or medical device.

The aptamer or conjugate may be placed onto various solid substrates, such as a stent, catheter (e.g., a peripheral intravenous catheter, a central venous catheter, or a urinary catheter, or a catheter hub, or a catheter port) or a non-degradable implant (e.g., such as a joint implant (knee, hip, ankle, etc.), a bone pin, or a prosthetic heart valve). In particular, the coating may be placed on vascular stents that are typically used for long periods of time.

Methods of Identifying and Purifying Aptamers

Figure 11:
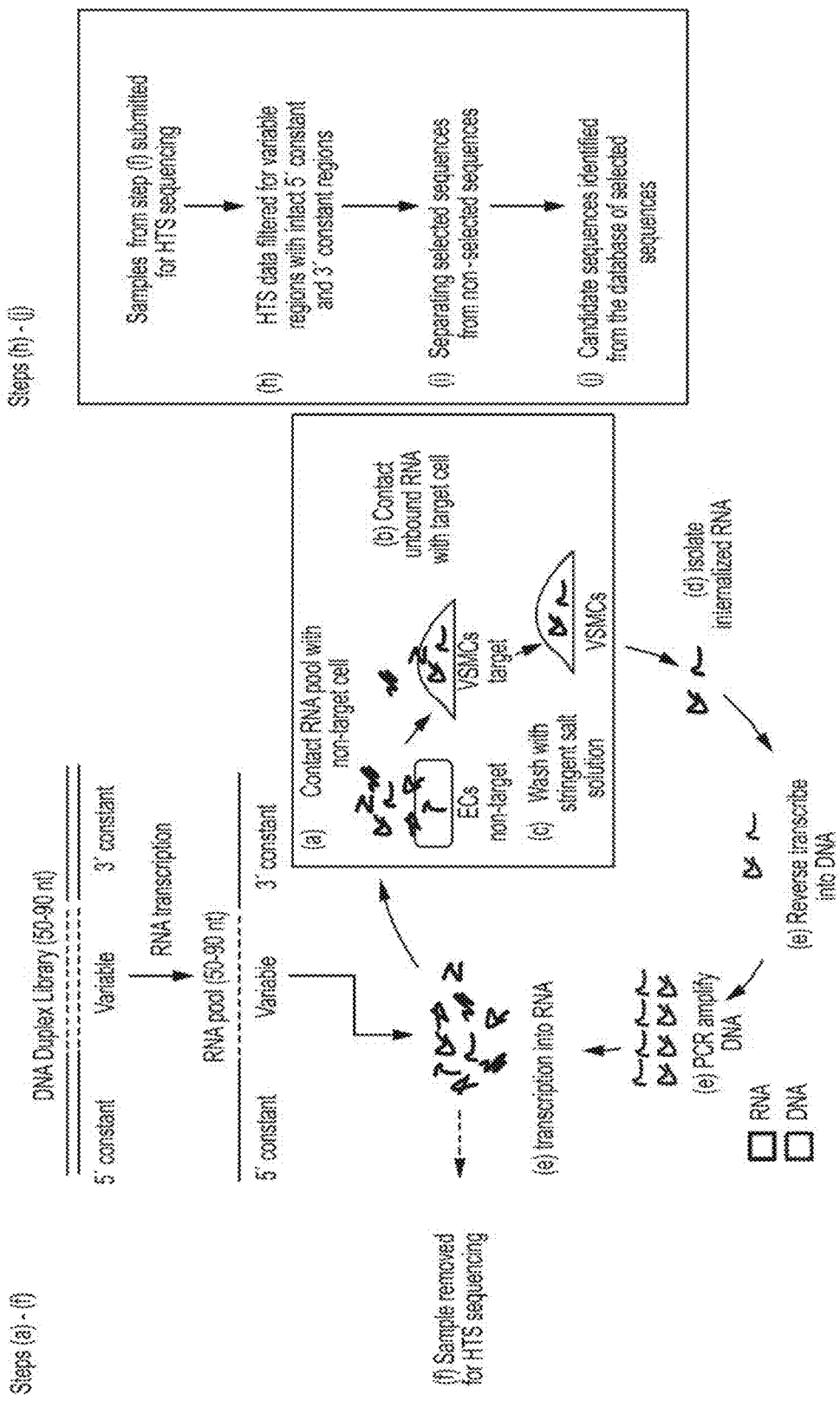
FIG. 11. Method of Identification of Novel Aptamers.

Certain embodiments of the present invention provide a method of isolating cell-internalized RNA (FIG. 11). In certain embodiments, the method comprises:

(a) contacting an initial RNA pool, consisting of RNA sequences derived from a duplex DNA library using in vitro transcription, with a non-target cell to generate unbound RNA and bound RNA and remove the bound RNA;

(b) contacting the unbound RNA with a target cell to generate cell-bound RNA, cell-unbound RNA, and cell-internalized RNA;

(c) wash the target cell with a stringent salt solution; and (d) isolate the cell-internalized RNA, wherein RNA in the RNA pool is not more than 90 nucleotides in length. In certain embodiments, the RNA is about 40-60 nucleotides in length, such as 45-50 nucleotides in length. The RNA pool can vary in length (e.g., 50-90 nt). The RNAs in the pool contain a central region of unique sequence flanked by constant sequence regions. In certain embodiments, the central region of unique sequence is about 15-25 nucleotides (e.g., 20 nt), and the constant sequence regions are about 10-20 nucleotides in length (e.g., 15 or 16 nt). As used herein the term "target cell" is a cell into which one desires to have an aptamer selectively enter. As used herein "selectively" means that the aptamer is internalized at a higher rate than a control, non-target cell. As used herein the term "bound" means that the aptamer attaches to the surface of the cell, e.g., binds to a cell receptor or other feature on the surface of the cell and is no longer free-floating in the media or solution. As used herein, the term "unbound RNA" refers to RNA that remains in the solution/media and not bound to the cells. As used herein the term "cell-internalized RNA" means RNA that can access the interior of the cell either by binding to a cell surface protein or directly traversing the cell membrane. In certain embodiments, the stringent salt solution comprises 0.5M NaCl in Dulbecco's Phosphate Buffered Saline (DPBS).

In certain embodiments, the contacting in step (a) is performed for 5 to 30 minutes, such as for 15 to 20 minutes. In certain embodiments, the contacting in step (b) is performed for 60 to 120 minutes, such as 75 to 100 minutes.

In certain embodiments, the method further comprises (f) obtaining a sample from the secondary RNA pool, (g) performing high throughput sequencing (HTS) to obtain raw reads of unique sequences and non-unique sequences, (h) filtering the raw reads based on RNA library constant region sequences (5' constant as HTS DNA sequence=5'-GGGAGGACGATGCGG-3' (SEQ ID NO: 1); 3' constant as HTS DNA sequence=5'-CAGACGACTCGCCCGA-3' (SEQ ID NO: 2)) to obtain filtered reads, and (i) determining which filtered reads are selected sequences (sequences enriched by the SELEX process) and which are non-selected sequences (background sequences indicative of the unenriched starting RNA pool).

(j) a database of selected sequences is analyzed for candidate sequences by calculating the fold enrichment of HTS reads between two rounds of selection, such as the fold enrichment of round 3 to round 8.

In certain embodiments, the method further comprises repeating steps (a)-(i) one to eight times.

In certain embodiments, steps (a)-(f) are repeated until complexity of the RNA in the secondary pool has reduced by 50% as compared to the initial pool at which point samples collect at (f) undergo steps (g)-(h).

In certain embodiments, the present invention provides a method of identifying a true-selected sequence by obtaining the number of times a unique sequence appears in each round of selection (cluster size), wherein true-selected sequence is a unique sequence that appears in at least three rounds of selection.

In certain embodiments, the present invention provides a method of identifying a true-selected sequence by comparing the unique sequences of different rounds of selection, and identifying a unique sequence present in at least two rounds of selection. As used herein a "round of selection" is a process involving steps (a)-(i). In certain embodiments, the method further comprising obtaining the number of times a unique sequence appeared in each round of selection. In certain embodiments, the method further comprises determining the edit distance of the unique sequences as compared to the other sequences in the round of selection. Edit distance is defined as the number of changes (substitution/insertion/deletion) necessary for two sequences to become identical. For example, closely-related sequences have a low edit distance, while unrelated or loosely-related sequences are denoted by a high edit distance.

In certain embodiments, the method further comprises determining the tree distance of the unique sequences as compared to the other sequences in the round of selection. "Tree distance" describes the relatedness of two structures by calculating the dissimilarity between two structures. Analogous with edit distance, closely-related structures have a low tree distance, while unrelated or loosely-related structures are denoted by a large tree distance. In certain embodiments, the present invention provides an aptamer having a true-selected sequence present in at least two rounds of selection, having a cluster size of at least 3, having an edit distance of 1, and having a tree distance of less than 3.

Detection Methods

The present invention provides methods for identifying regions of the vasculature that have had endothelial damage or de-endothelialization or impaired re-endothelialization. The aptamers of the present invention may also be used to identify regions of plaque rupture or instability, or of smooth muscle cell activation. in a sample or in vivo. In certain embodiments, the aptamers are modified to include fluorescent dyes or tracers to facilitate the identification of restenosed vessels. For example, one can contact a sample with an aptamer as described herein or the composition as described herein to form bound VSMC or VSMC that contain internalized aptamers, and detecting the presence or the quantity of VSMC aptamers. Alternatively, aptamers or compositions can be administered in vivo to a patient (e.g. injected in situ into a tumor). In certain embodiments, the bound VSMC aptamer is detected by means of PCR, nuclear magnetic resonance, fluorescent capillary electrophoresis, lateral flow devices, colorimetry, chemiluminescence, fluorescence, southsester blots, microarrays, or ELISA.

Amplification Methods

In one embodiment of the present invention, the method involves the amplification of selected RNAs. "Amplifying" utilizes methods such as the polymerase chain reaction (PCR), ligation amplification (or ligase chain reaction. LCR), strand displacement amplification, nucleic acid sequence-based amplification, and amplification methods based on the use of Q-beta replicase. These methods are well known and widely practiced in the art. Reagents and hardware for conducting PCR are commercially available. In one embodiment of the present invention, at least one type of aptamer is immobilized on a solid surface.

According to the methods of the present invention, the amplification may be carried out by any means known to the art. Examples of suitable amplification techniques include, but are not limited to, polymerase chain reaction (including, for RNA amplification, reverse-transcriptase polymerase chain reaction), ligase chain reaction, strand displacement amplification, transcription-based amplification, self-sustained sequence replication (or "3SR"), the Qβ replicase system, nucleic acid sequence-based amplification (or "NASBA"), the repair chain reaction (or "RCR"), and boomerang DNA amplification (or "BDA").

The bases incorporated into the amplification product may be natural or modified bases (modified before or after amplification), and the bases may be selected to optimize subsequent electrochemical detection steps.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized that is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques. Where the nucleic acid to be amplified is RNA, amplification may be carried out by initial conversion to DNA by reverse transcriptase in accordance with known techniques.

Strand displacement amplification (SDA) may be carried out in accordance with known techniques. For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present invention) that hybridizes to the target sequence to be amplified and/or detected. The flanking sequence, which serves to facilitate binding of the restriction enzyme to the recognition site and provides a DNA polymerase priming site after the restriction site has been nicked, is about 15 to 20 nucleotides in length in one embodiment. The restriction site is functional in the SDA reaction. The oligonucleotide probe portion is about 13 to 15 nucleotides in length in one embodiment of the invention.

Ligase chain reaction (LCR) is also carried out in accordance with known techniques. In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

Diagnostic techniques that are useful in the methods of the invention include, but are not limited to direct DNA sequencing, pulsed-field gel electrophoresis (PFGE) analysis, allele-specific oligonucleotide (ASO), dot blot analysis and denaturing gradient gel electrophoresis, and are well known to the artisan.

The sample may be contacted with the aptamer in any suitable manner known to those skilled in the art. For example, the sample may be solubilized in solution, and contacted with the aptamer by solubilizing the aptamer in solution with the sample under conditions that permit binding. Suitable conditions are well known to those skilled in the art. Alternatively, the sample may be solubilized in solution with the aptamer immobilized on a solid support, whereby the sample may be contacted with the aptamer by immersing the solid support having the aptamer immobilized thereon in the solution containing the sample.

Diseases and Conditions Amendable to the Methods of the Invention

In the certain embodiments of the present invention, a mammalian recipient to an expression cassette of the invention has a condition that is amenable to detection or therapy using the aptamers of the present invention. In certain embodiments, the mammal has or is suspected of having vascular disease. In certain embodiments, the vascular disease is one in which the mechanism of disease development and/or progression includes smooth muscle cell activation (defined by smooth muscle cell migration and/or proliferation and/or phenotypic modulation and/or changes in gene expression). These diseases include but are not necessary limited to pulmonary hypertension, transplant vasculopathy, atherosclerosis, venous bypass graft failure, arteriovenous fistula failure, restenosis following percutaneous or surgical intravascular intervention (e.g., balloon angioplasty, atherectomy, brachytherapy, and stenting), and hypertensive vasculopathy.

Accordingly, as used herein, the term "therapeutic small molecule" refers to any small molecule that has a beneficial effect on the recipient. Thus, "therapeutic small molecule" embraces both therapeutic and prophylactic small molecules.

General Terminology

"Synthetic" aptamers are those prepared by chemical synthesis. The aptamers may also be produced by recombinant nucleic acid methods. "Recombinant nucleic molecule" is a combination of nucleic sequences that are joined together using recombinant nucleic technology and procedures used to join together nucleic sequences known in the art.

The term "chimeric" refers to a gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may include regulatory sequences and coding sequences that are derived from different sources, or include regulatory sequences and coding sequences derived from the same source, but arranged in a manner different from that found in nature.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

By "fragment" or "portion" is meant a full length or less than full length of the nucleotide sequence.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

As used herein, "sequence identity" or "identity" in the context of two nucleic acid sequences makes reference to a specified percentage of residues in the two sequences that are the same when aligned by sequence comparison algorithms or by visual inspection.

As used herein, "percentage of sequence identity" means the value determined by comparing two optimally aligned sequences, wherein the portion of the polynucleotide sequence may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched nucleic acid. Specificity is typically the function of post-hybridization washes, the critical factors being the ionic strength and temperature of the final wash solution. For DNA-DNA hybrids, the $T_m$ can be approximated from the equation of Meinkoth and Wahl: $T_m$ 81.5° C.+16.6 (log M)+0.41 (% GC)−0.61 (% form)−500/L. M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

"Operably-linked" nucleic acids refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

The terms "isolated and/or purified" refer to in vitro isolation of a nucleic acid, e.g., a DNA or RNA molecule from its natural cellular environment, and from association with other components of the cell or test solution (e.g. RNA pool), such as nucleic acid or polypeptide, so that it can be sequenced, replicated, and/or expressed. For example, "isolated nucleic acid" may be a DNA molecule containing less than 31 sequential nucleotides that is transcribed into an RNAi molecule. Such an isolated RNAi molecule may, for example, form a hairpin structure with a duplex 21 base pairs in length that is complementary or hybridizes to a sequence in a gene of interest, and remains stably bound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

As used herein, the term "derived" or "directed to" with respect to a nucleotide molecule means that the molecule has complementary sequence identity to a particular molecule of interest.

"Treating" as used herein refers to ameliorating at least one symptom of, curing and/or preventing the development of a disease or a condition.

Disclosed herein is a strategy that results in substantial silencing of targeted genes via RNAi. Use of this strategy results in markedly diminished in vitro and in vivo expression of targeted genes. This strategy is useful in reducing expression of targeted genes in order to model biological processes or to provide therapy for human diseases. For example, this strategy can be applied to a the treatment of cancer. As used herein the term "substantial silencing" means that the mRNA of the targeted gene is inhibited and/or degraded by the presence of the introduced siRNA, such that expression of the targeted gene is reduced by about 10% to 100% as compared to the level of expression seen when the siRNA is not present. Generally, when a gene is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the siRNA is not present. As used herein the term "substantially normal activity" means the level of expression of a gene when an siRNA has not been introduced to a cell.

To accomplish intracellular expression of the therapeutic RNAi molecules, an RNA molecule is constructed containing two complementary strands or a hairpin sequence (such as a 21-bp hairpin) representing sequences directed against the gene of interest. The RNAi molecule, or a nucleic acid encoding the RNAi molecule, is introduced to the target cell, such as a diseased brain cell. The RNAi molecule reduces target mRNA and protein expression.

The construct encoding the therapeutic RNAi molecule is configured such that the one or more strands of the RNAi molecules are encoded by a nucleic acid that is immediately contiguous to a promoter. In one example, the promoter is a pol II promoter. If a pol II promoter is used in a particular construct, it is selected from readily available pol II promoters known in the art, depending on whether regulatable, inducible, tissue or cell-specific expression of the siRNA is desired. The construct is introduced into the target cell, allowing for diminished target-gene expression in the cell.

The present invention provides an expression cassette containing an isolated nucleic acid sequence encoding an RNAi molecule targeted against a gene of interest. The RNAi molecule may form a hairpin structure that contains a duplex structure and a loop structure. The loop structure may be the aptamer portion. The duplex is less than 30 nucleotides in length, such as from 19 to 25 nucleotides. The RNAi molecule may further contain an overhang region. Such an overhang may be a 3' overhang region or a 5' overhang region. The overhang region may be, for example, from 1 to 6 nucleotides in length. The expression cassette may further contain a pol II promoter, as described herein. Examples of pol II promoters include regulatable promoters and constitutive promoters. For example, the promoter may be a CMV or RSV promoter. The expression cassette may further contain a polyadenylation signal, such as a synthetic minimal polyadenylation signal. The nucleic acid sequence may further contain a marker gene or stuffer sequences. The expression cassette may be contained in a viral vector. An appropriate viral vector for use in the present invention may be an adenoviral, lentiviral, adeno-associated viral (AAV), poliovirus, herpes simplex virus (HSV) or murine Maloney-based viral vector. The gene of interest may be a gene associated with a condition amenable to siRNA therapy. Examples of such conditions include neurodegenerative diseases, such as a trinucleotide-repeat disease (e.g., polyglutamine repeat disease). Examples of these diseases include Huntington's disease or several spinocerebellar ataxics. Alternatively, the gene of interest may encode a ligand for a chemokine involved in the migration of a cancer cell, or a chemokine receptor.

The present invention also provides an expression cassette containing an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as an RNAi molecule targeted against a gene of interest. The expression cassette may be contained in a vector, such as a viral vector.

The present invention provides a method of reducing the expression of a gene product in a cell by contacting a cell with an expression cassette described above. It also provides a method of treating a patient by administering to the patient a composition of the expression cassette described above.

The present invention further provides a method of reducing the expression of a gene product in a cell by contacting a cell with an expression cassette containing an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as an RNAi molecule targeted against a gene of interest.

The present method also provides a method of treating a patient, by administering to the patient a composition containing an expression cassette, wherein the expression cassette contains an isolated nucleic acid sequence encoding a first segment, a second segment located immediately 3' of the first segment, and a third segment located immediately 3' of the second segment, wherein the first and third segments are each less than 30 bases in length and each more than 10 bases in length, and wherein the sequence of the third segment is the complement of the sequence of the first segment, and wherein the isolated nucleic acid sequence functions as an RNAi molecule targeted against a gene of interest.

An RNAi molecule may be a "small interfering RNA" or "short interfering RNA" or "siRNA" or "short hairpin RNA" or "shRNA" or "microRNA" or "miRNA." An RNAi molecule an RNA duplex of nucleotides that is targeted to a nucleic acid sequence of interest. As used herein, the term "RNAi molecule" is a generic term that encompasses the subset of shRNAs. A "RNA duplex" refers to the structure formed by the complementary pairing between two regions of a RNA molecule. RNAi molecule is "targeted" to a gene in that the nucleotide sequence of the duplex portion of the RNAi molecule is complementary to a nucleotide sequence of the targeted gene. In certain embodiments, the RNAi molecules are targeted to the sequence encoding Plk1. In some embodiments, the length of the duplex of RNAi molecules is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the RNAi molecule can be part of a hairpin structure. In addition to the duplex portion, the hairpin structure may contain a loop portion positioned between the two sequences that form the duplex. In certain embodiments, the loop is 9 nucleotides in length. The hairpin structure can also contain 3' or 5' overhang portions. In some embodiments, the overhang is a 3' or a 5' overhang 0, 1, 2, 3, 4 or 5 nucleotides in length.

A "small interfering" or "short interfering RNA" or siRNA is a RNA duplex of nucleotides that is targeted to a gene interest. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length. The "sense" and "antisense" sequences can be attached to the aptamer portion to form aptamer chimeras. As used herein, the term RNAi molecule is meant to be equivalent to other terms used to describe nucleic acid molecules that are capable of mediating sequence specific RNAi, for example, double-stranded RNA (dsRNA), micro-RNA (miRNA), short hairpin RNA (shRNA), short interfering oligonucleotide, short interfering nucleic acid, post-transcriptional gene silencing RNA (ptgsRNA), and others. In addition, as used herein the term RNAi is meant to be equivalent to other terms used to describe sequence specific RNA interference, such as post transcriptional gene silencing, translational inhibition, or epigenetic silencing. In a non-limiting example, modulation of gene expression by siRNA molecules of the invention can result from siRNA mediated cleavage of RNA (either coding or non-coding RNA) via RISC, or alternately, translational inhibition as is known in the art.

The RNAi molecule can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

The RNAi molecule can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

"Knock-down," "knock-down technology" refers to a technique of gene silencing in which the expression of a target gene is reduced as compared to the gene expression prior to the introduction of the RNAi molecule, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where RNAi molecules have not been administered). Knock-down of gene expression can be directed, for example, by the use of dsRNAs, siRNAs or miRNAs.

"RNA interference (RNAi)" is the process of sequence-specific, post-transcriptional gene silencing initiated by an RNAi molecule. During RNAi, RNAi molecules induce degradation of target mRNA with consequent sequence-specific inhibition of gene expression. RNAi involving the use of RNAi molecules has been successfully applied to knockdown the expression of specific genes in plants, *D. melanogaster, C. elegans*, trypanosomes, planaria, hydra, and several vertebrate species including the mouse.

The term "suppressing" refers to the diminution, reduction or elimination in the number or amount of transcripts present in a particular cell.

The terms "protein," "peptide" and "polypeptide" are used interchangeably herein.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an RNAi molecule. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art.

Administration of the aptamer chimera may be accomplished through the administration of the nucleic acid molecule. Pharmaceutical formulations, dosages and routes of administration for nucleic acids are generally known in the art.

The present invention envisions treating a disease, for example, vascular stenosis, restenosis or stroke, in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation), can be administered by a variety of routes including parenteral, including by intravenous and intramuscular routes, as well as by direct injection into the diseased tissue. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0, saline solutions, and water.

Example 1

Rapid Identification of Cell-Specific, Internalizing RNA Aptamers with Bioinformatics Analysis of a Cell-based Aptamer Selection Nucleic acid aptamers represent an emerging class of pharmaceuticals under development for diagnostic and therapeutic use. Some properties of aptamers that make them promising therapeutic reagents include the intermediate size of aptamers, ease of development, and absence of synthesis constraints associated with small molecule inhibitors and protein-based drugs (e.g., antibodies). Aptamers routinely achieve binding affinities and specificities comparable to therapeutic antibodies. In addition, due to their amenability to modification by medicinal chemistry. aptamers avoid the immunogenicity concerns of protein-based drugs and can be engineered to have optimized pharmacokinetic (PK) and pharmacodynamic (PD) profiles for in vivo applications (1,2). Furthermore, aptamers can be generated to a range of therapeutic targets more efficiently than is the case for small molecules, high-throughput drug screens or cell-based antibody production.

Isolation of aptamers with affinity and specificity for a target of interest involves iterative rounds of affinity purification and amplification via a process termed SELEX (Systematic Evolution of Ligands by EXponential enrichment) (3,4). In a typical SELEX experiment, a random sequence oligonucleotide library (with approximately $1 \times 10^{15}$ sequences) is incubated with a protein target. The protein-bound aptamers are then specifically recovered and amplified by PCR. Single stranded DNA or RNA sequences are then generated from the amplified product and used in a subsequent round of selection. Since the invention of the SELEX process around 1990, many high affinity aptamers that target a wide-range of proteins including transcription factors (5-8), cytokines (9), growth factors (10-13), proteases (14, 15), serum proteins (16-18), cell-surface receptors (19-24), cell-adhesion molecules (25-28) and viral proteins (3, 29-31_have been identified.

Although the traditional SELEX method utilizes a soluble, pure form of the target protein (i.e., recombinant protein), different methods have also been developed that target aptamers to membrane-associated cell surface proteins, termed whole-cell SELEX) (21, 24, 32-38). Like traditional SELEX, whole-cell SELEX is an evolutionary approach, yet whole-cell SELEX allows the selection of aptamers without prior knowledge of specific targets (36-39). Furthermore, whole-cell SELEX can, in principle, generate aptamers to multiple targets in parallel while favoring accessible cell surface epitopes. A major advantage of the whole-cell SELEX method over the traditional in vitro SELEX approach is that it facilitates the identification of aptamer sequences that recognize the target (e.g. membrane receptor) in its native milieu; that is, in the context of the cellular membrane. Importantly, this approach overcomes the difficulties in obtaining purified preparations of recombinant membrane proteins (1, 40). In addition, whole-cell SELEX eliminates the risk that one could select aptamers that will only bind to the purified protein and do not recognize the native form of the protein on living cells.

Aptamers that bind to extracellular targets have high potential for diagnostic and therapeutic applications. For diagnostics, aptamers are used to differentiate among different cell types, such as normal and tumor cells (28). For therapeutic applications, aptamers that bind to the cell surface can be used directly as activators or inhibitors, or indirectly to direct therapeutics, including small molecule drugs, radioisotopes, toxins or siRNAs, to persist in the vicinity of a specific cell or tissue type (2). The latter strategy is likely to increase efficacy as well as reduce potential unwanted toxic effects of the therapy. In addition, these reagents can also potentially be used to deliver therapeutics into the cells by increasing the rate of receptor-mediated endocytosis (41).

While whole cell-SELEX has increased the repertoire of aptamers that bind to membrane receptors (21,33), this methodology does not necessarily select for aptamers capable of accessing intracellular compartments for delivering macromolecules into cells. To isolate RNA aptamers that internalize into target cells, we have recently developed a novel cell-based selection strategy that we refer to as cell-internalization SELEX (24). The present approach has several advantages over the traditional in vitro SELEX approach: (1) it favors the isolation of RNAs that bind to receptors in their native state; and (2) it enriches for RNAs that are internalized by the target cell. Using the cell-internalization SELEX approach, we enriched for aptamers that selectively bind to and internalize into $HER2^+$-breast cancer cells for delivering therapeutic siRNAs to the cancer cells (24).

A potential downside to the cell-based SELEX approaches as compared to traditional in vitro SELEX is that cells are much more complex targets than single recombinant proteins. Two major challenges for cell-based aptamer selections are 1) insufficient methods to monitor the progression of a cell-based selection, and 2) the complexity of aptamer sequences derived from this type of selection. We address these issues by applying a combination of HTS and bioinformatics analysis to the cell-internalization SELEX approach. In this study, we demonstrate the usefulness of this approach by identifying vascular smooth muscle cell (VSMC)-specific internalizing aptamers. We also demonstrate the importance of categorizing aptamers based on structural similarity (structure families), in addition to sequence similarity (sequence families), in order to encourage the identification of functional sequences. In summary, these studies demonstrate the utility of HTS and bioinformatics analysis for facilitating the rapid identification of 'winner' sequences from an aptamer selection performed against a complex target. Furthermore, these studies have resulted in several VSMC-specific internalizing RNA sequences that could be used to deliver siRNAs or other small molecule drugs specifically to VSMCs.

Results

Enrichment of VSMC-Specific Internalizing RNA Aptamers

Figure 6:
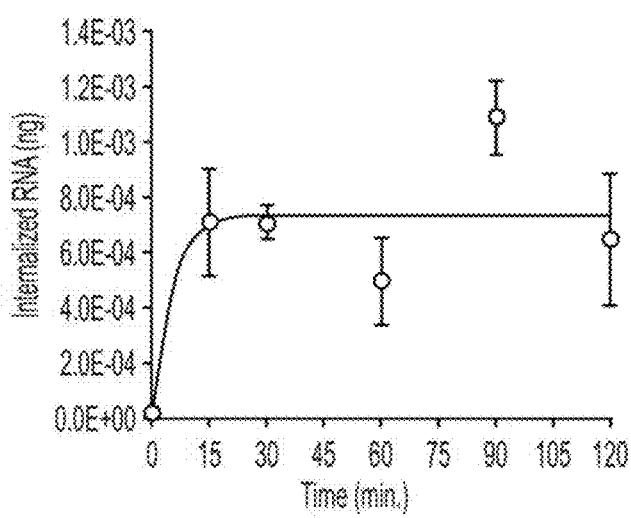
FIG. 6. Amount of RNA aptamer library (Round 0) internalized into VSMCs over time. Round 0 RNA was incubated with VSMCs (A7r5) for 15, 30, 60, 90 or 120 minutes. Unbound RNA or RNA bound to the surface of cells was removed with a stringent salt wash. Internalized RNA was extracted by TRIzol extraction and measured using RT-qPCR.

Aptamers that selectively internalize into vascular smooth muscle cells (VSMCs; A7r5) were enriched using the cell-internalization SELEX protocol (FIG. 1A). The cell-internalization SELEX protocol involves incubating pools of RNAs from an RNA library with a non-target cell (negative selection) and a target cell (positive selection) (FIG. 1A). Rounds 1 through 3 of selection were performed against target VSMCs (A7r5) using positive selection criteria (Table 1). RNA was incubated with cells for 90 minutes, based on a predetermined time for maximizing RNA internalization into these cells (FIG. 6). To enable the identification of VSMC-specific sequences, a negative selection step against endothelial cells (ECs; YPEN-1) was introduced at rounds 4 through 8 of selection (Table 4). Importantly, to enrich for RNA aptamers that internalize into the target VSMCs, we introduced a stringent salt wash to remove any unbound RNA and to reduce surface-bound RNAs.

TABLE 1

| | | Selection conditions | | | |
|---|---|---|---|---|---|
| | | Pre-clear | | Internalization | |
| Round | [RNA] | Cell Line | Time | Cell Line | Time (min.) |
| 1 | 150 nM | | | A7r5 | 90 min. |
| 2 | 150 nM | | | A7r5 | 90 min. |
| 3 | 150 nM | | | A7r5 | 90 min. |

TABLE 1-continued

Selection conditions

| Round | [RNA] | Pre-clear Cell Line | Pre-clear Time | Internalization Cell Line | Internalization Time (min.) |
|---|---|---|---|---|---|
| 4 | 150 nM | 1x YPEN-1 | 20 min. | A7r5 | 60 min. |
| 5 | 150 nM | 1x YPEN-1 | 20 min. | A7r5 | 60 min. |
| 6 | 150 nM | 1x YPEN-1 | 20 min. | A7r5 | 60 min. |
| 7 | 150 nM | 2x YPEN-1 | 2x 10 min. | A7r5 | 30 min. |
| 8 | 150 nM | 2x YPEN-1 | 2x 10 min. | A7r5 | 30 min. |

Figures 1B, 12:
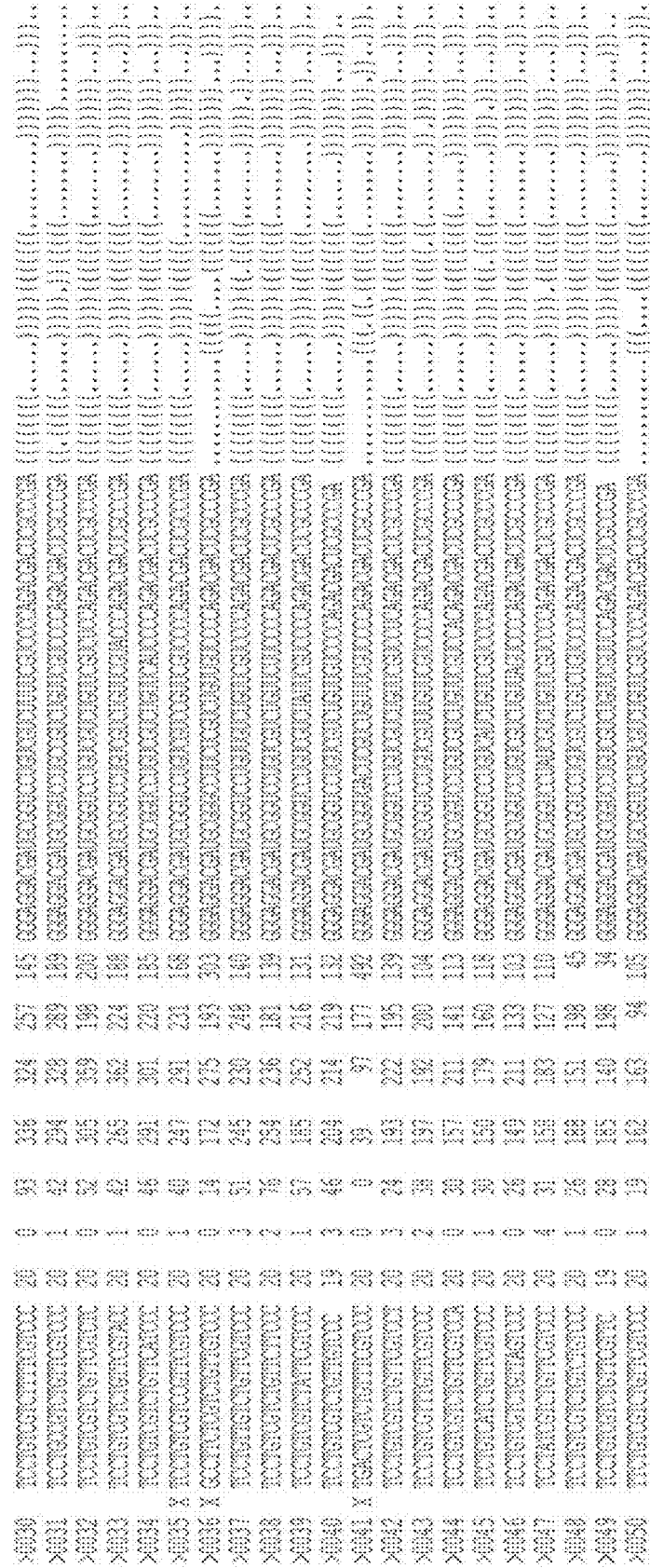

We monitored the progression of the selection by measuring the complexity of the RNA pools at each round of selection using a modified DiStRO DNA melt assay (42) (FIGS. 1B-1D). The DNA melt assay allows for rapid and cost-effective analysis of selection progression and can be easily applied to complex cell-based selections. In this assay, the DNA from a given selection round (from the PCR amplification SELEX step) is heated at high temperatures (melted) and, as the temperature is decreased, the efficiency of re-annealing of the melted DNA is measured by SYBR green fluorescence. A relative loss in library complexity is indicative of a shift in the DNA melt curve towards higher temperatures. A significant drop in library complexity was observed between rounds 2 and 3 of selection as evidenced by the shift in the round 3 DNA melt curve towards higher temperatures, compared to the DNA melt curves of rounds 0 through 2 (FIG. 1B). This initial drop in library complexity was an indication that additional selective pressures could be introduced to further enrich for VSMCs-specific RNA aptamers. Thus, a negative-selection step (pre-clear against YPEN-1 cells) was introduced at round 4 of selection (Table 1). In addition, to enrich for RNA aptamers that are more rapidly internalized into VSMCs (A7r5), we reduced the time the RNA pool was incubated on cells from 90 minutes to 60 minutes (Table 1). These selection pressures were maintained for three consecutive rounds (rounds, 4, 5 and 6) until no further changes in library complexity were observed (Table 1 and FIG. 1C). At this point, we introduced additional selective pressures into each round: a second negative-selection step and a shorter incubation time for the RNA pools with VSMCs (Table 1). Interestingly, a DNA melt assay performed on rounds 6, 7 and 8 of selection indicated no further increase in convergence (FIG. 1D). These data suggest that selection convergence was achieved at round 6 and that further rounds of selection may not be necessary.

We next verified cell-specific internalization of the RNA pools at each round of selection (FIG. 1E). RNA from rounds 0, 2, 4, 6 and 8 of selection was incubated with either VSMCs (A7r5) or ECs (YPEN-1). Those RNAs that internalized into the cells were recovered by TRIzol extraction and quantified using RT-qPCR (24). The absence of RNA was used as a negative control in this assay. Importantly, cell-specific internalization was achieved as early as round 4 of selection (FIG. 1E). Maximum internalization into VSMCs was attained at round 6 with no significant increases in VSMC internalization in subsequent rounds (FIG. 1E). These data are in concert with the data generated from the DNA melt assay (FIGS. 1B-1D) and suggest that selection convergence for VSMC-specific internalizing RNAs occurred at round 6 of selection.

HTS, using Illumina sequencing technology, was performed to enable the bioinformatics analysis of millions of sequence reads from selection rounds 0, 1, 3, 5, 6, 7 and 8.

Figures 2A, 12:
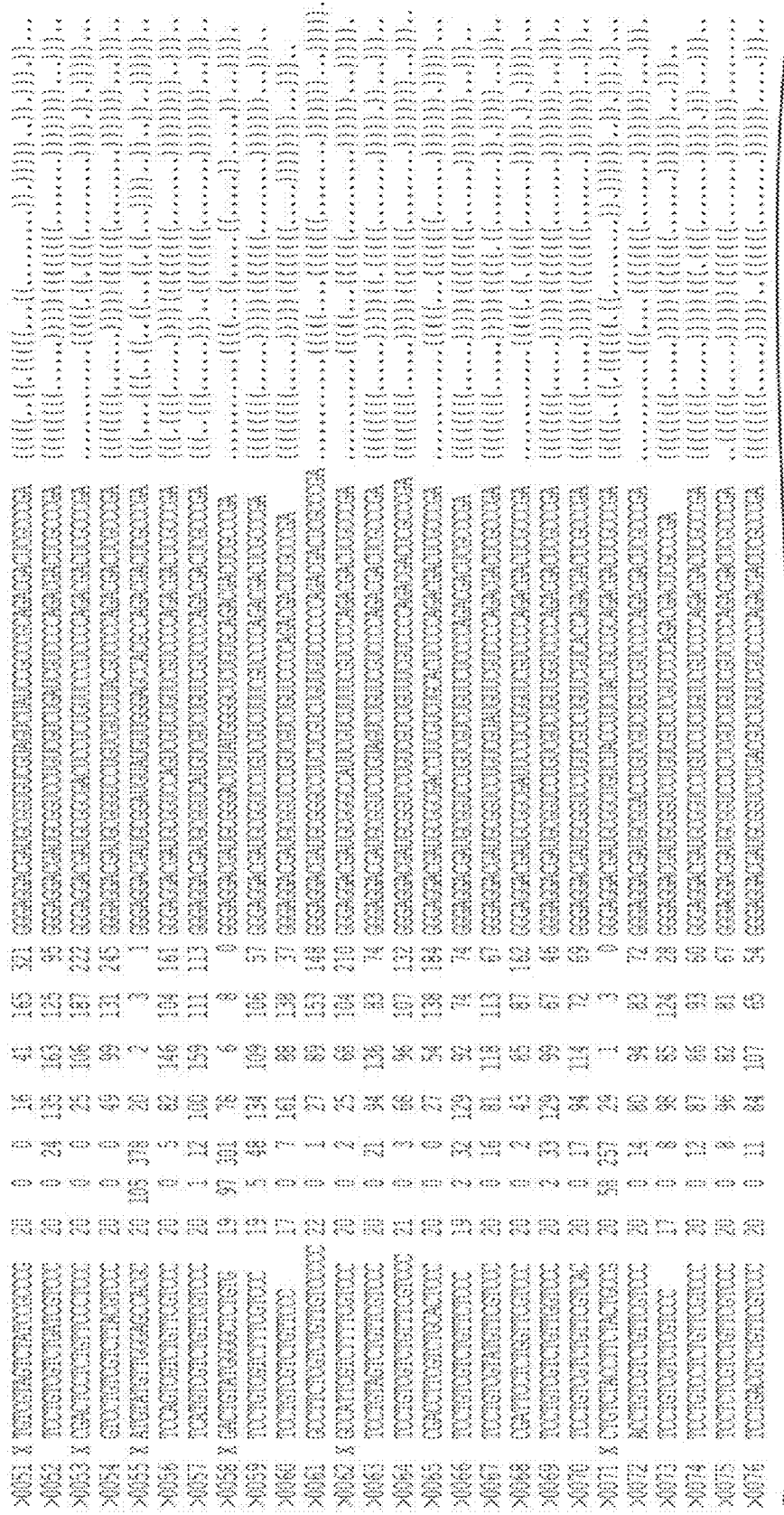

We obtained a total of 2,605,039 raw reads from the sequenced rounds (Table 4). These raw reads were filtered based on the RNA library constant region sequences. After filtering, 2,546,770 total reads were obtained. Of the total filtered reads, 1,425,964 were unique reads (Table 4). After normalizing to total reads (white squares) at each round of selection, the number of unique reads (black squares) was decreased with each subsequent round (FIG. 2A). This decrease in the number of unique reads observed at later rounds of selection (rounds 4 through 8) is indicative of a decrease in library sequence complexity and an increase in library sequence enrichment.

Figures 2B, 12:
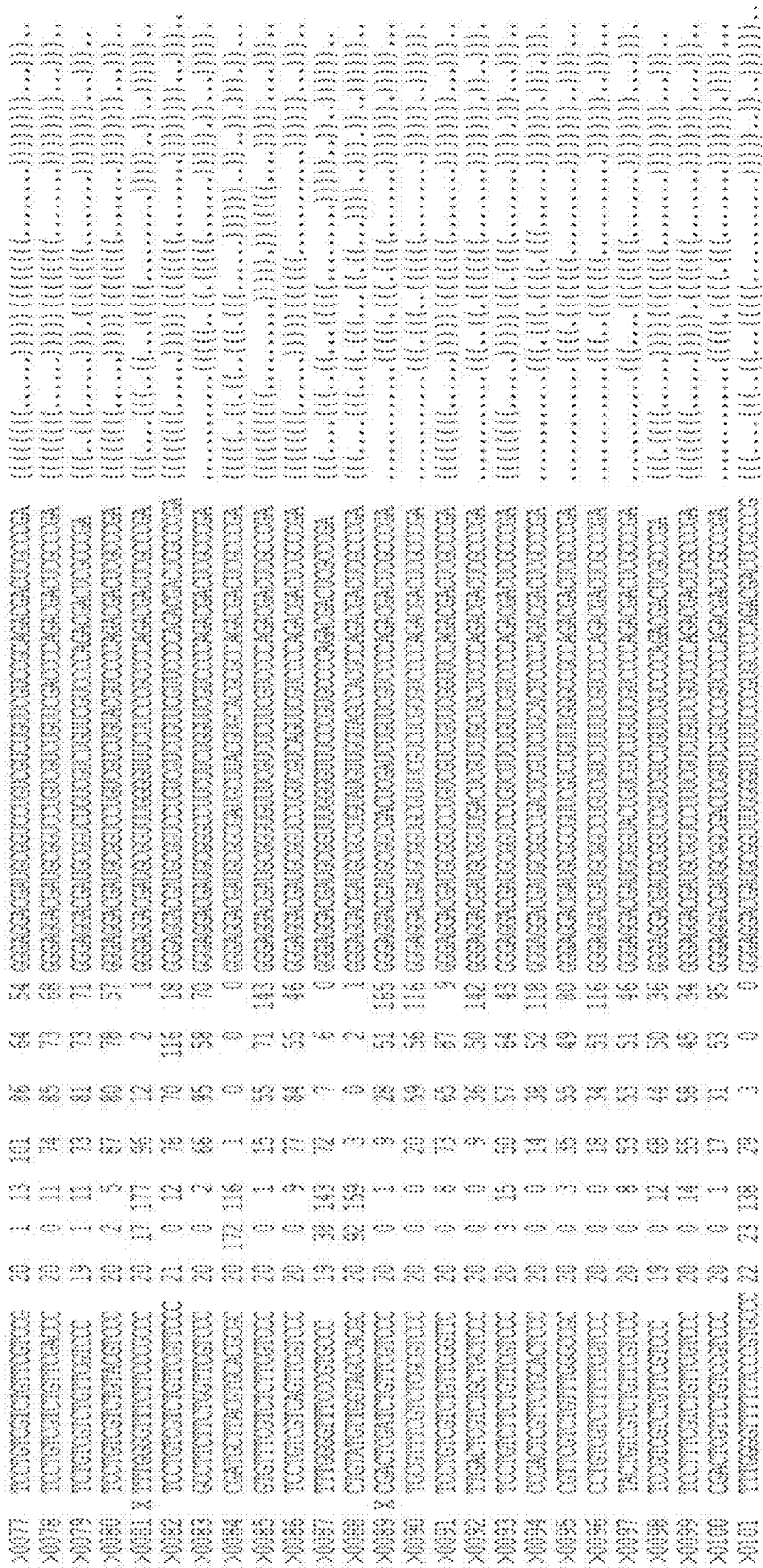
Figures 3B, 12:
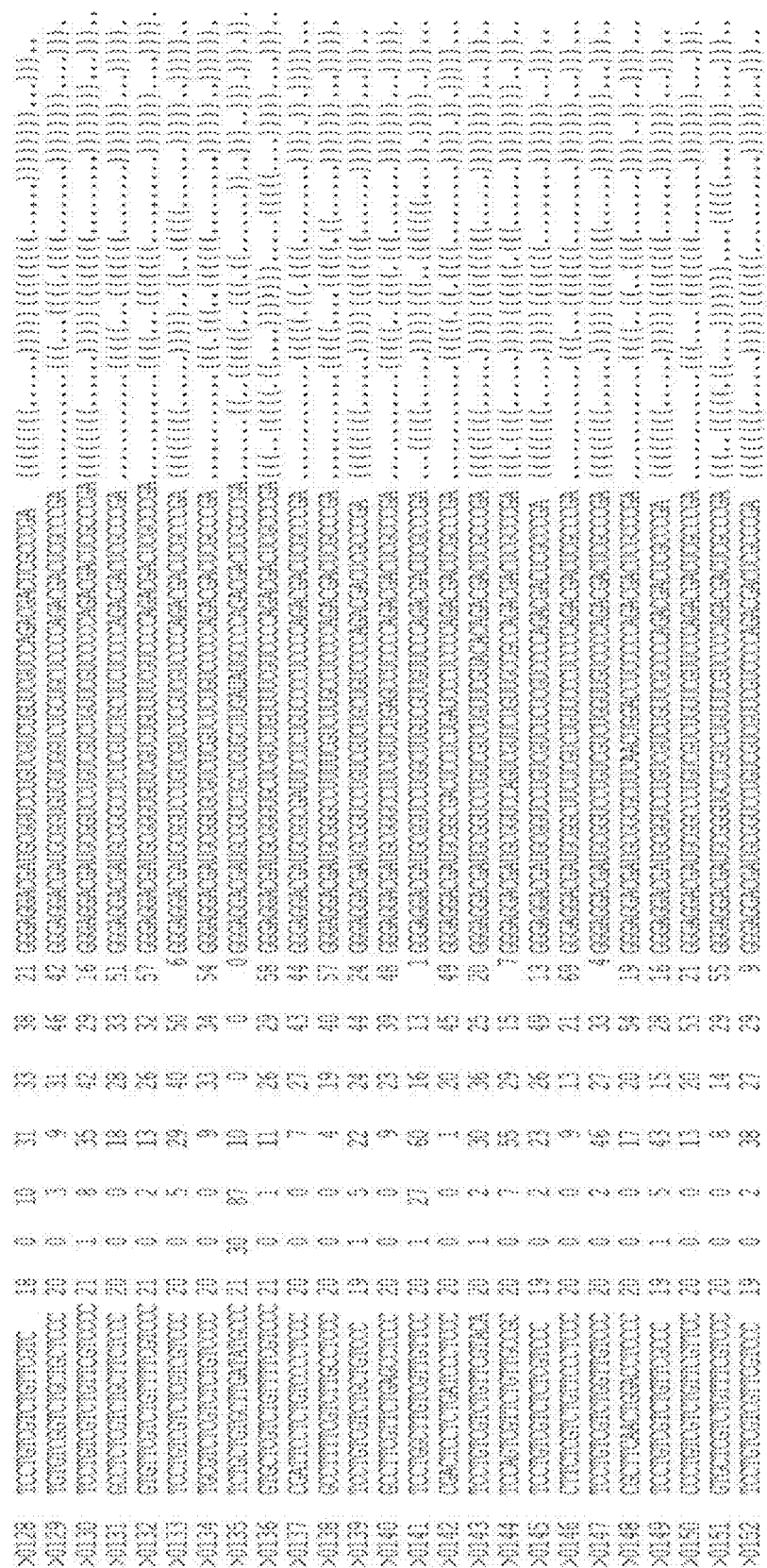
Figures 4B, 12:
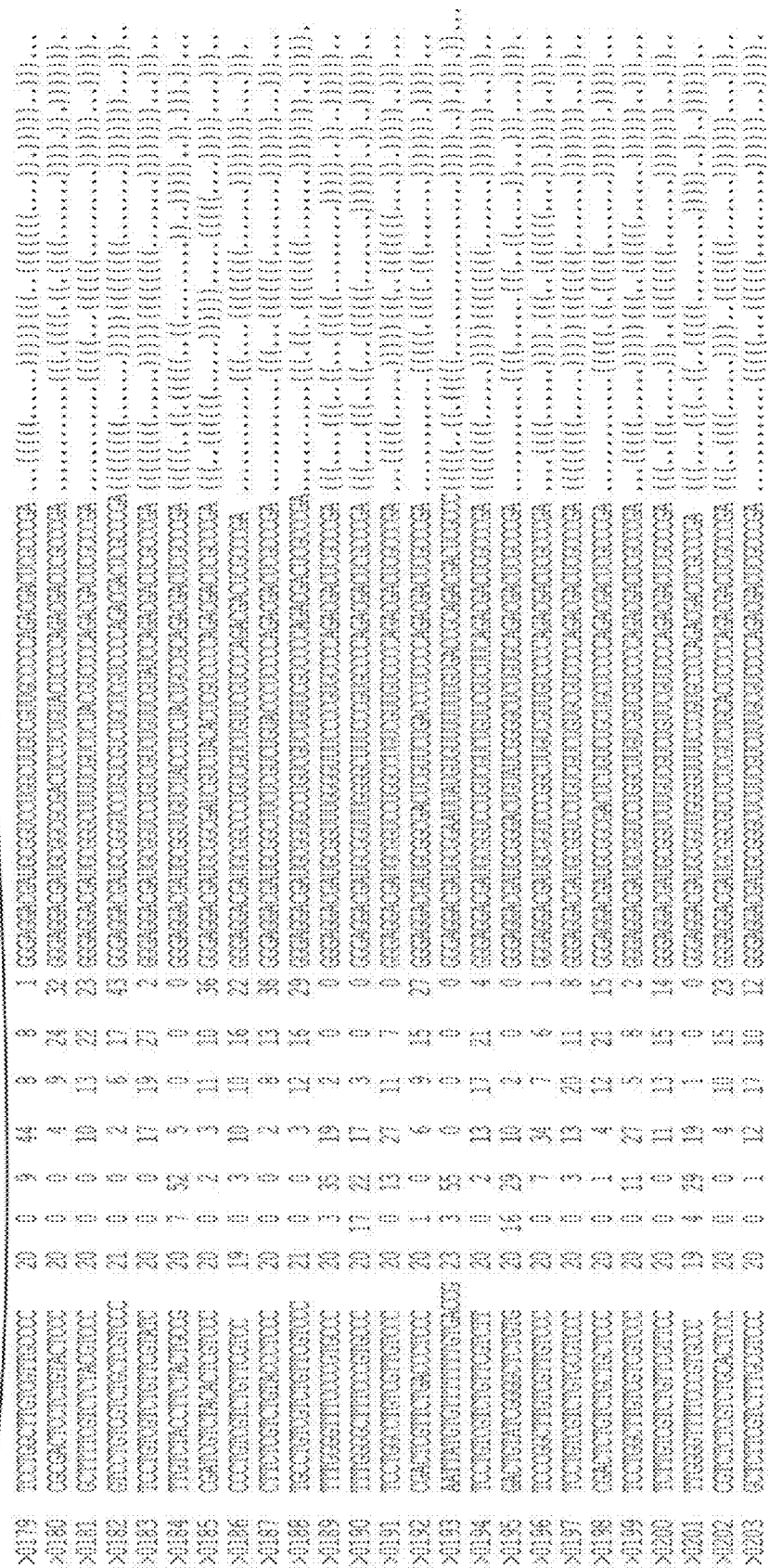
Figures 5A, 12:
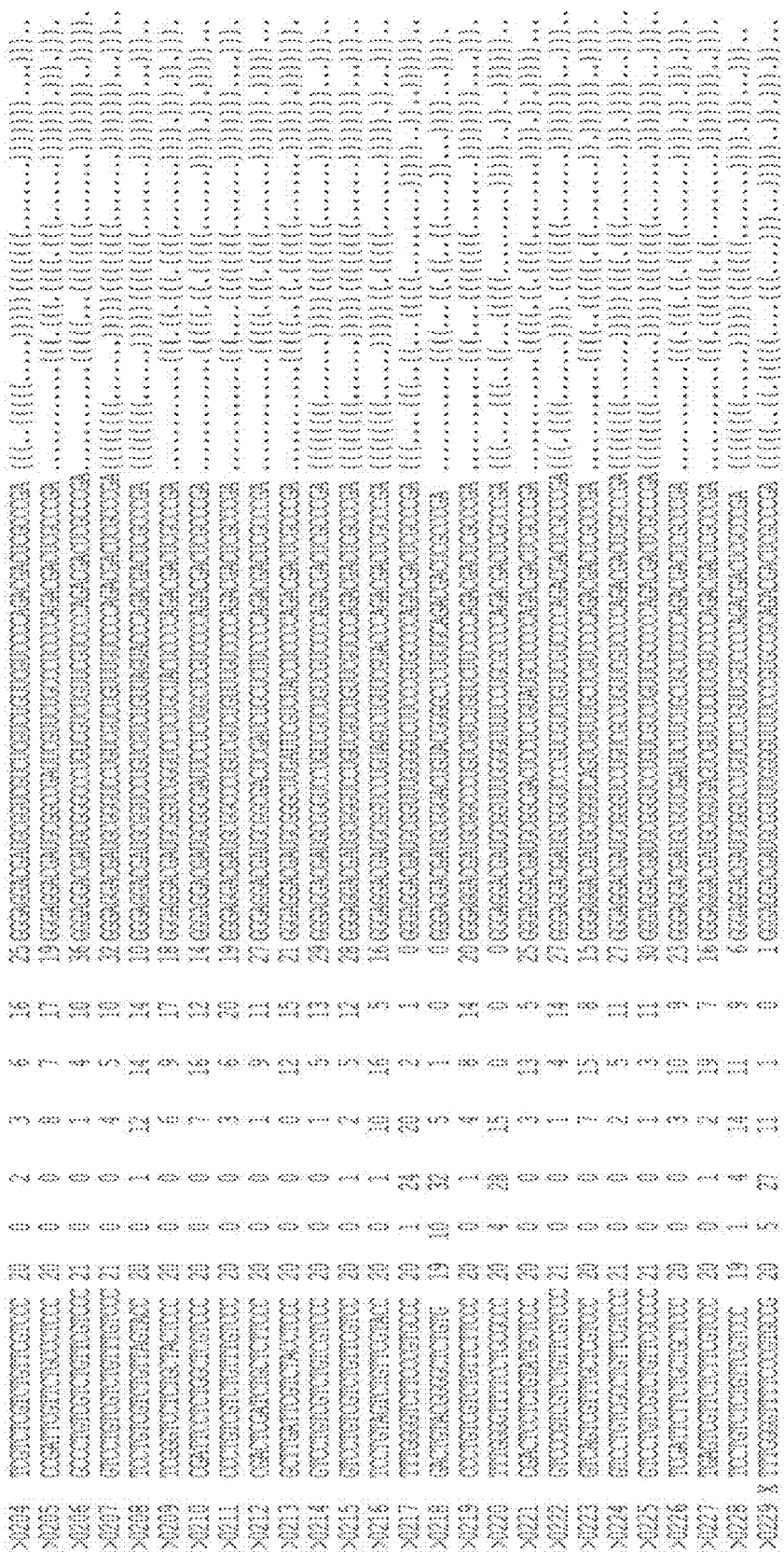
Figures 5B, 12:
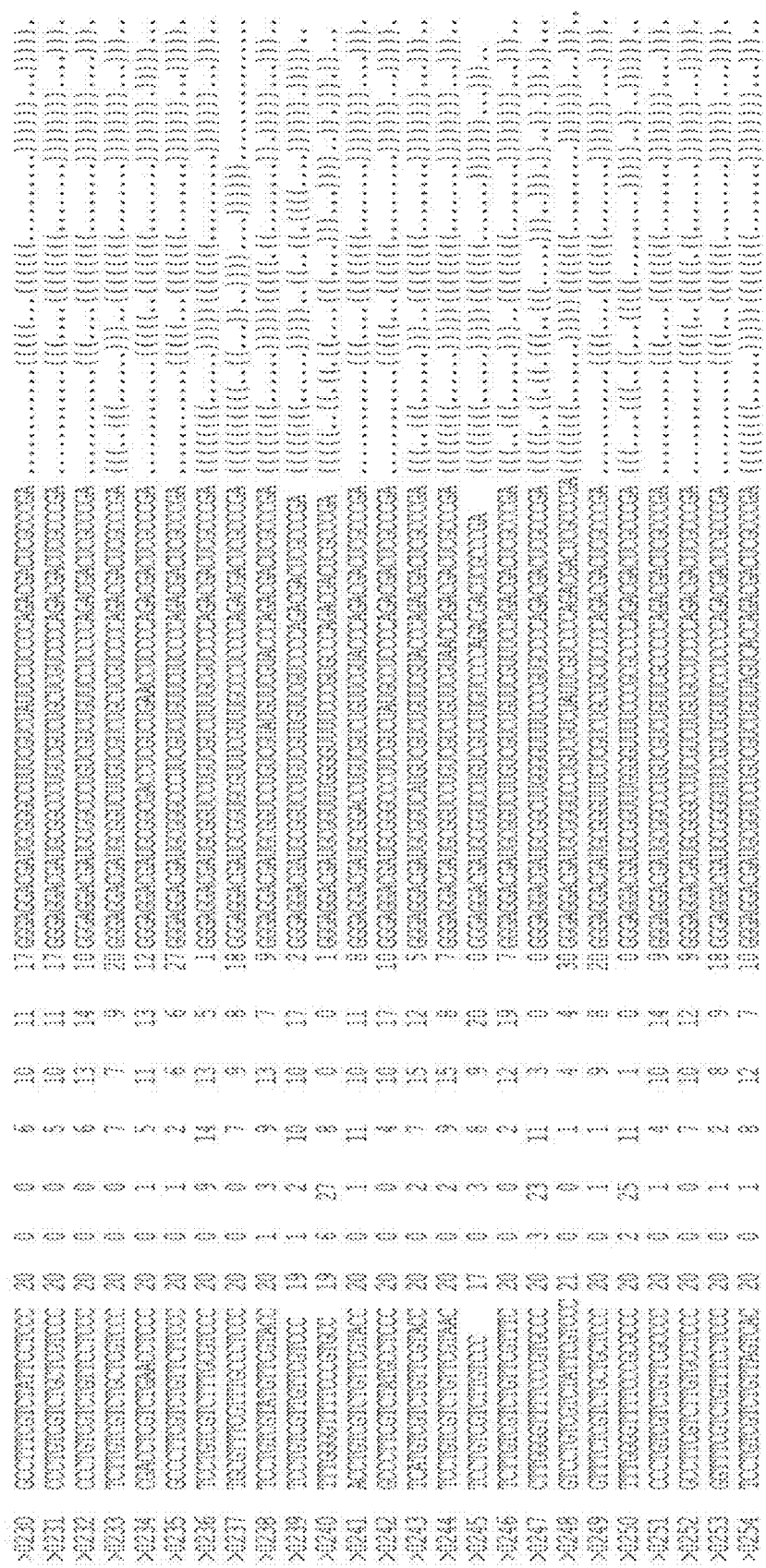
Figures 6A, 12:
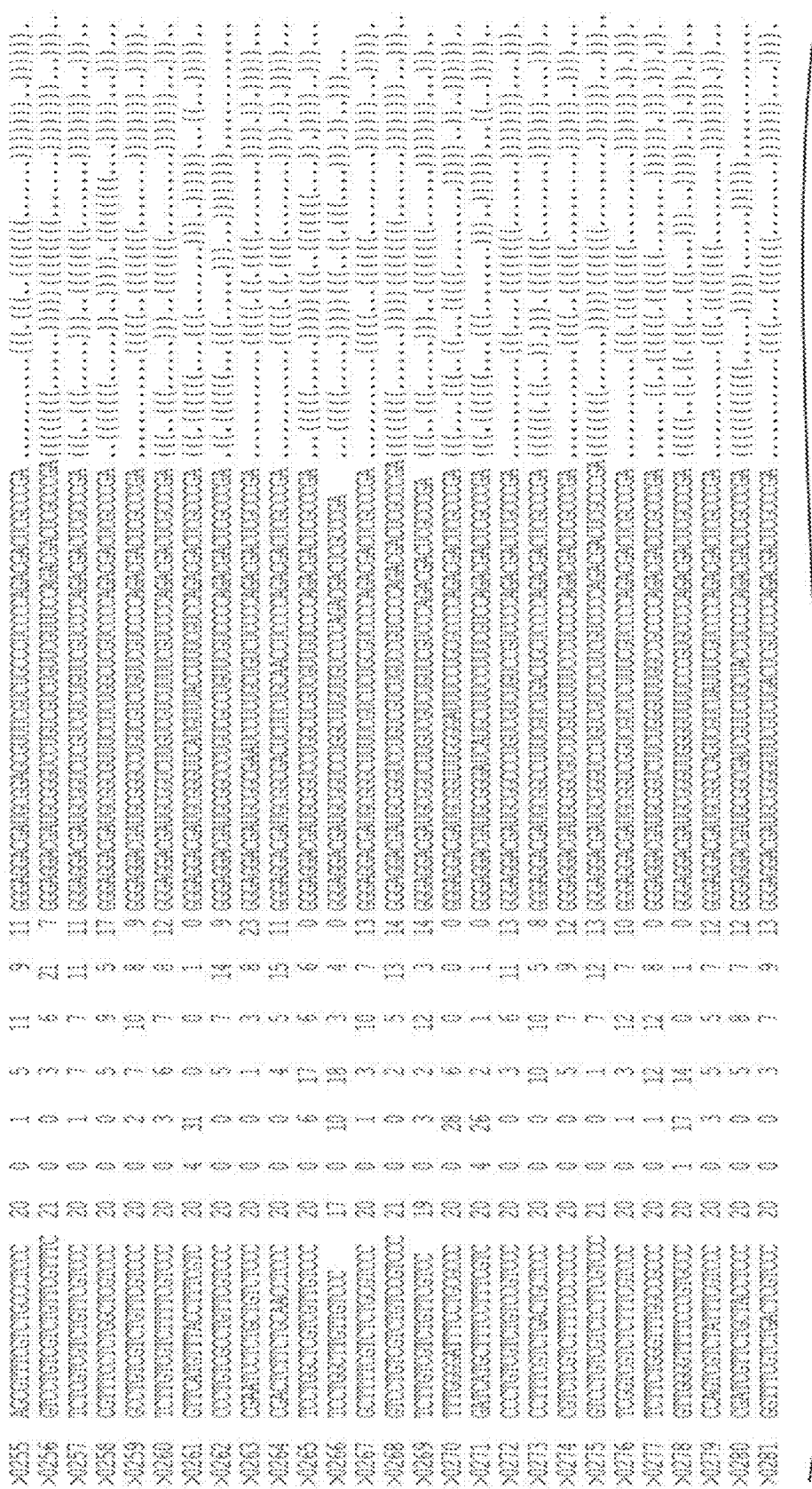
Figures 6B, 12:
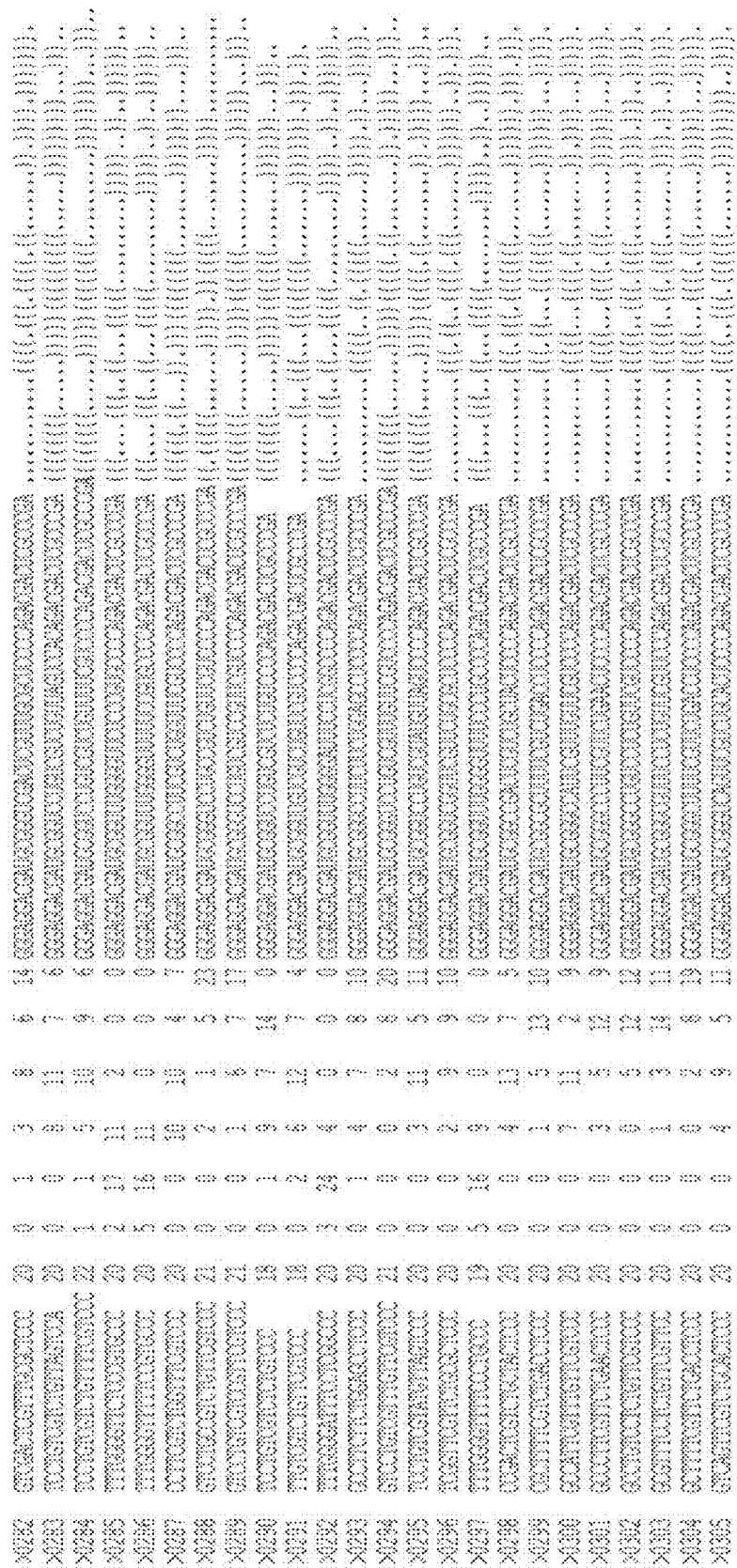
Figures 7B, 12:
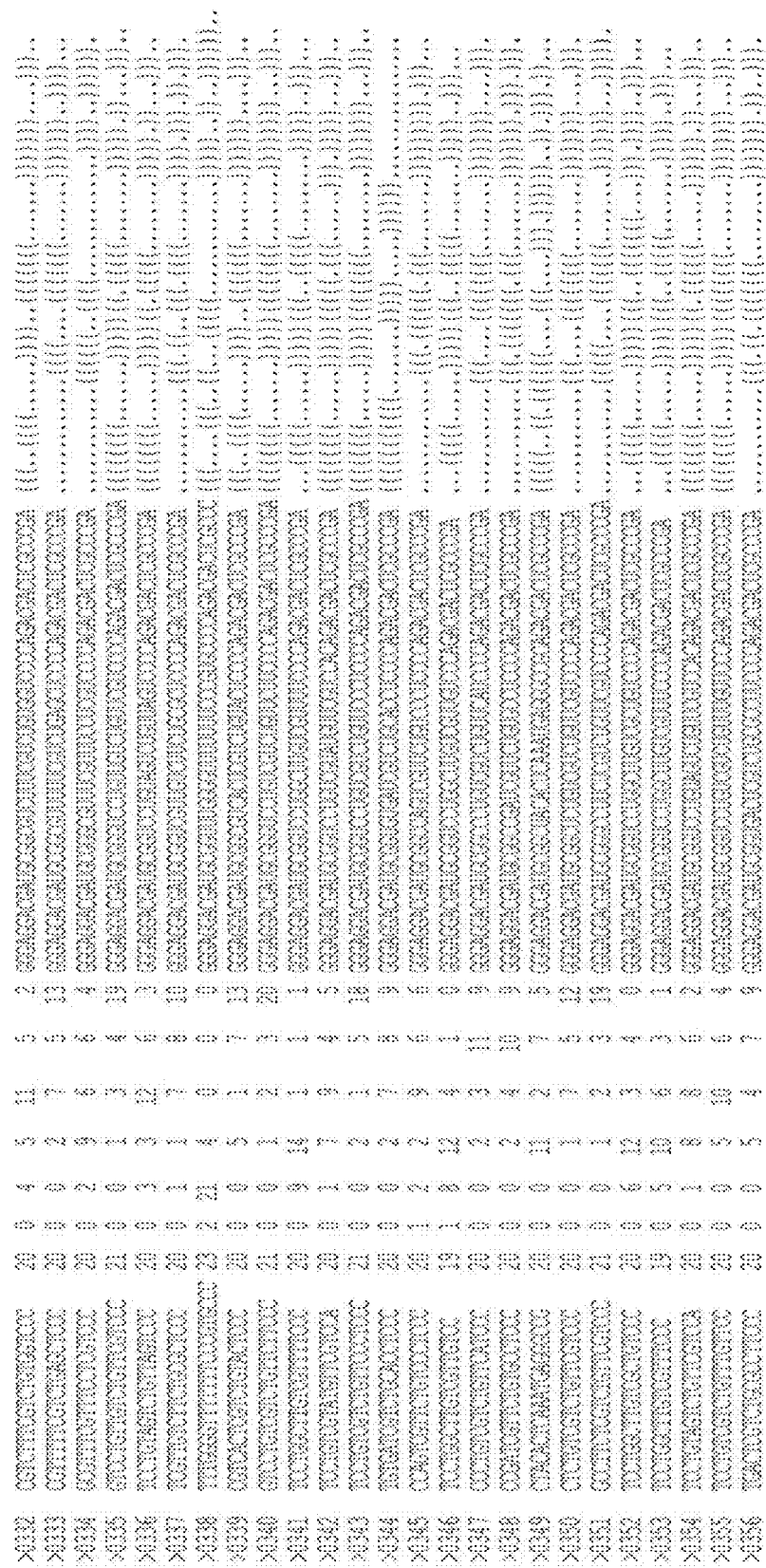
Figures 10A, 12:
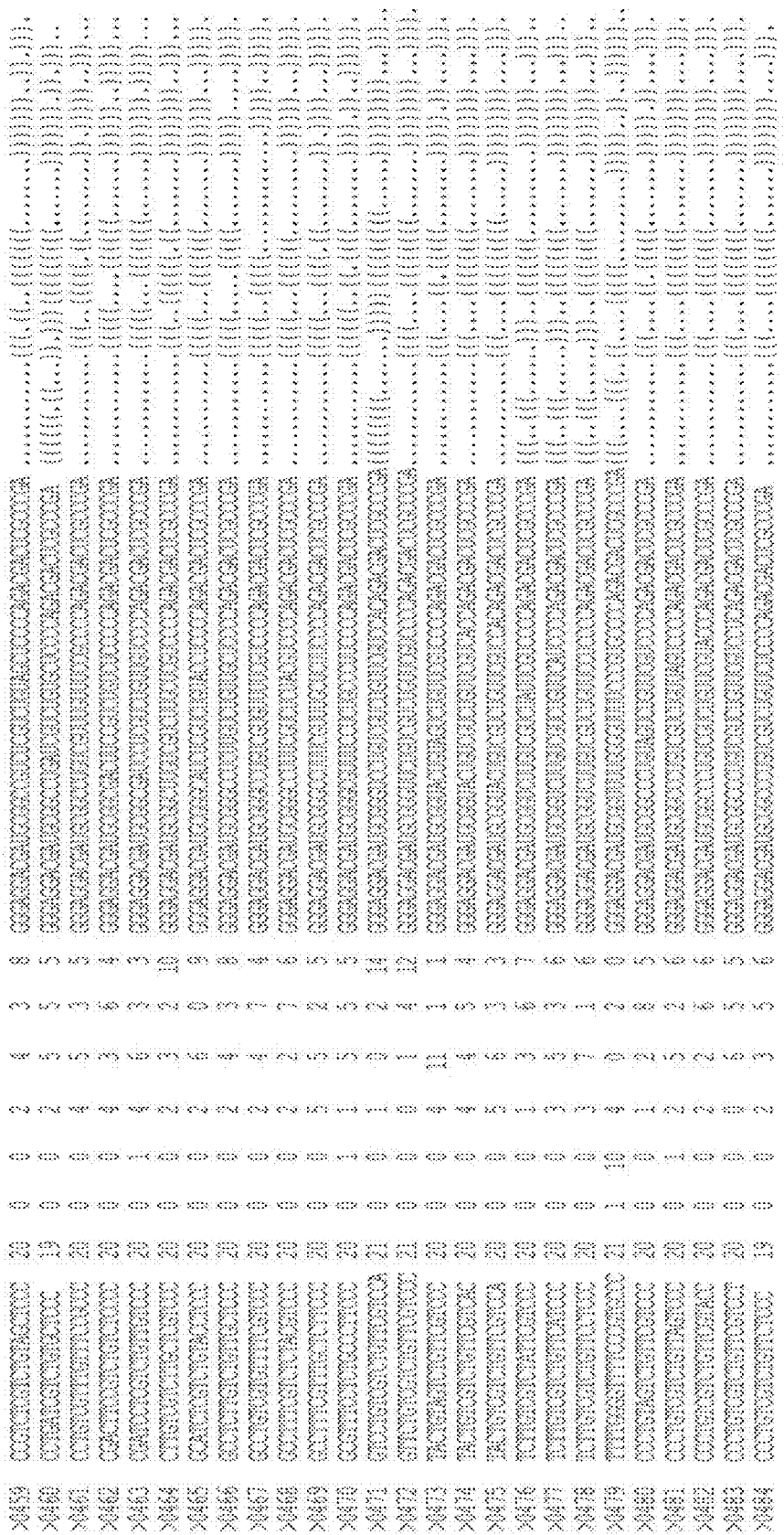
Figures 11B, 12:
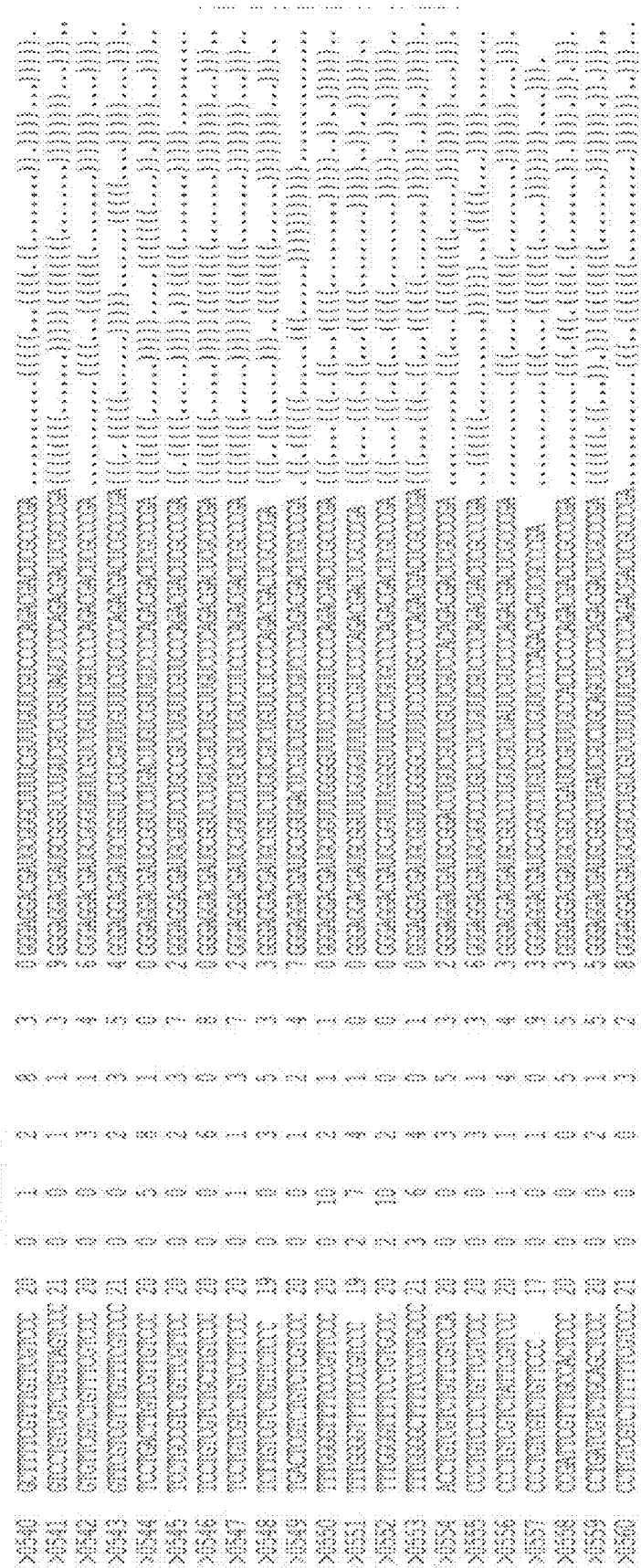
Figures 12, 12B:
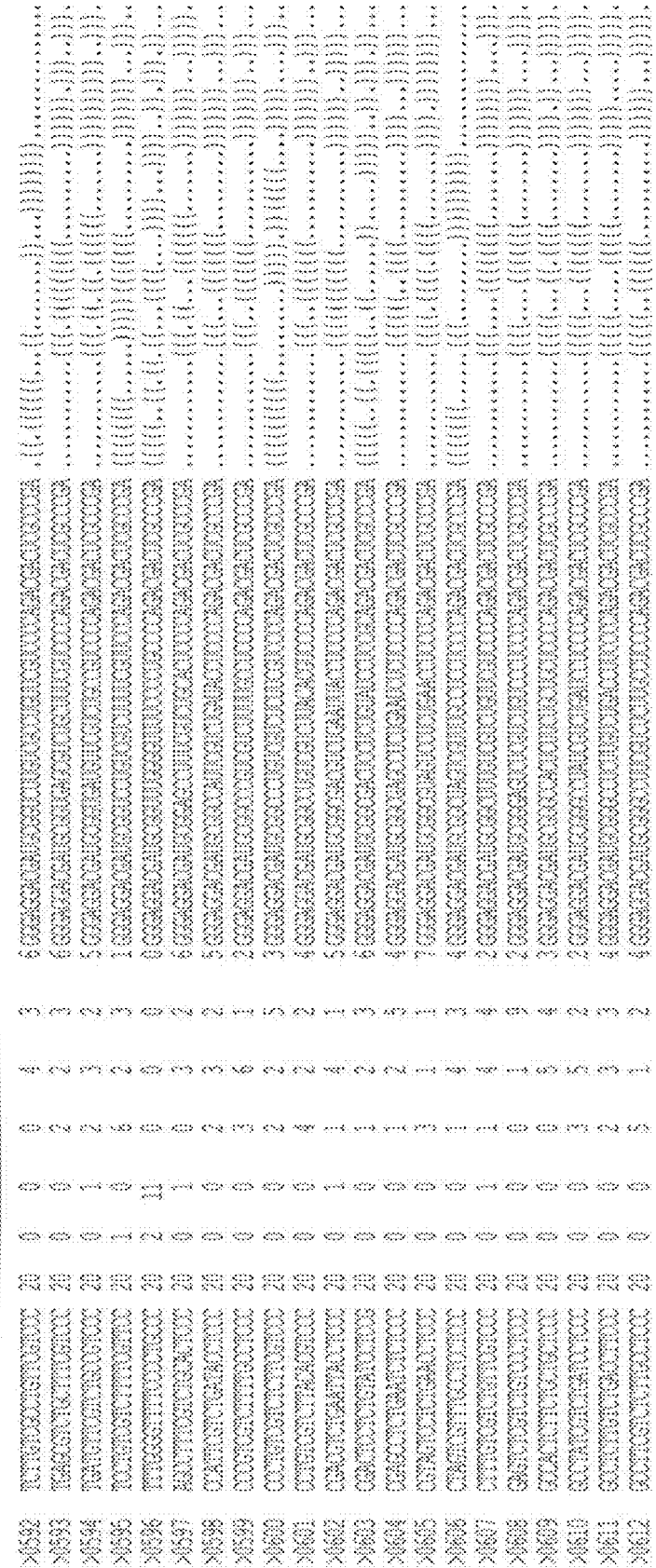
Figures 12, 13, 13A:
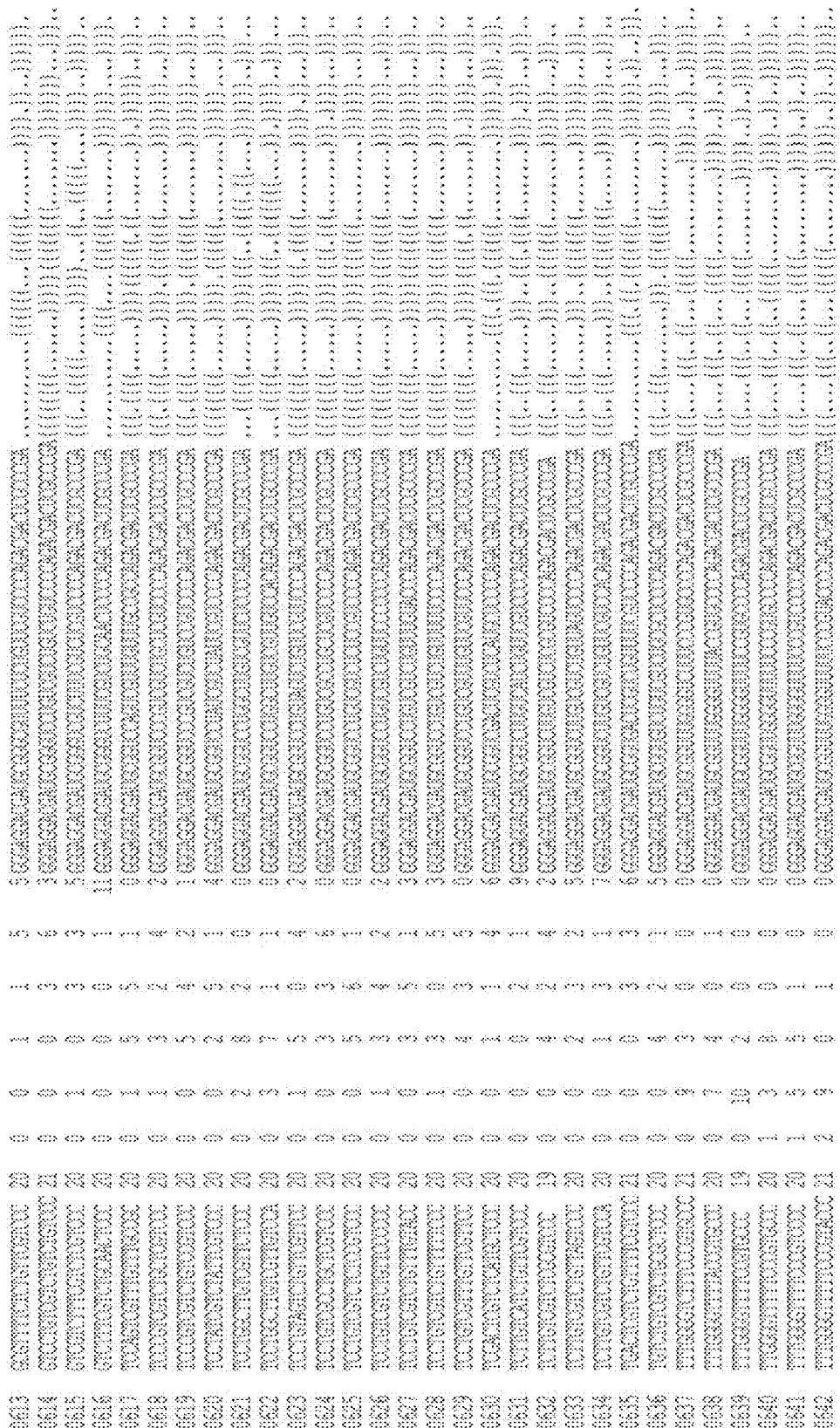
Figures 12, 13, 14, 14B:
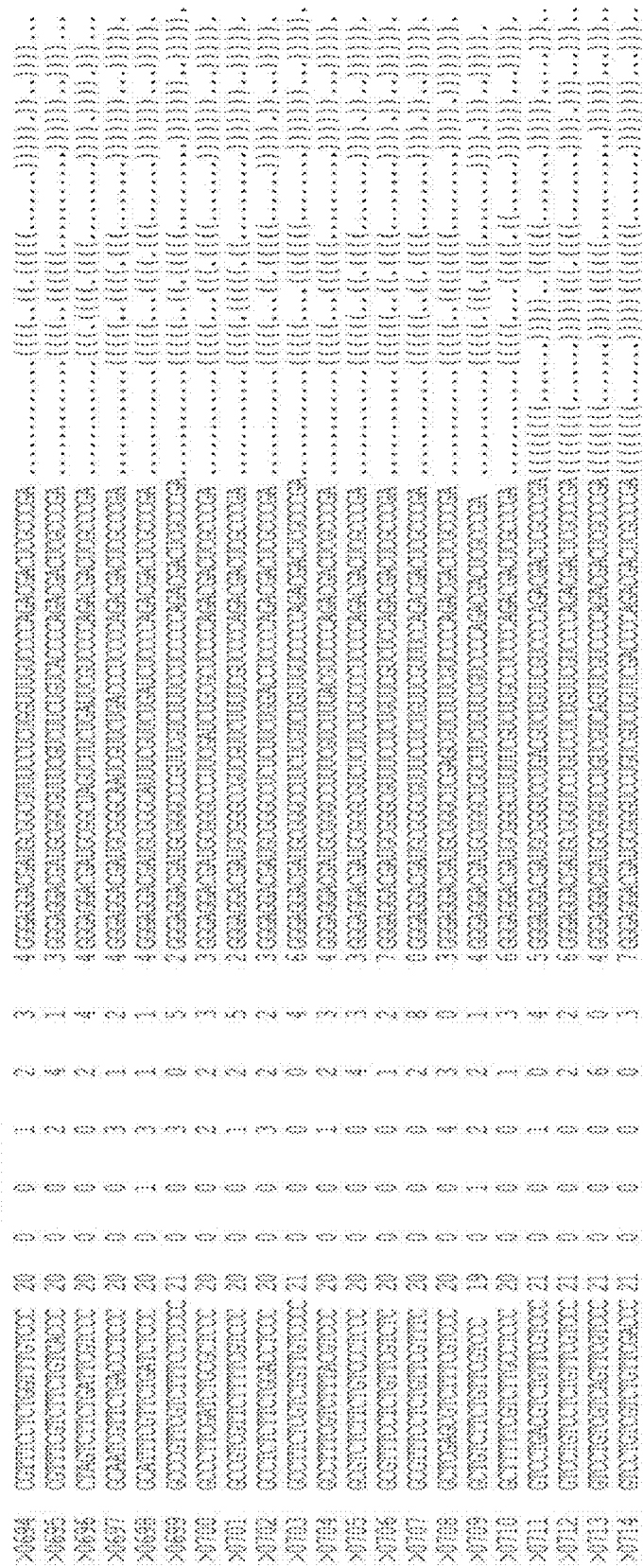
Figures 12, 13, 14, 15, 15B:
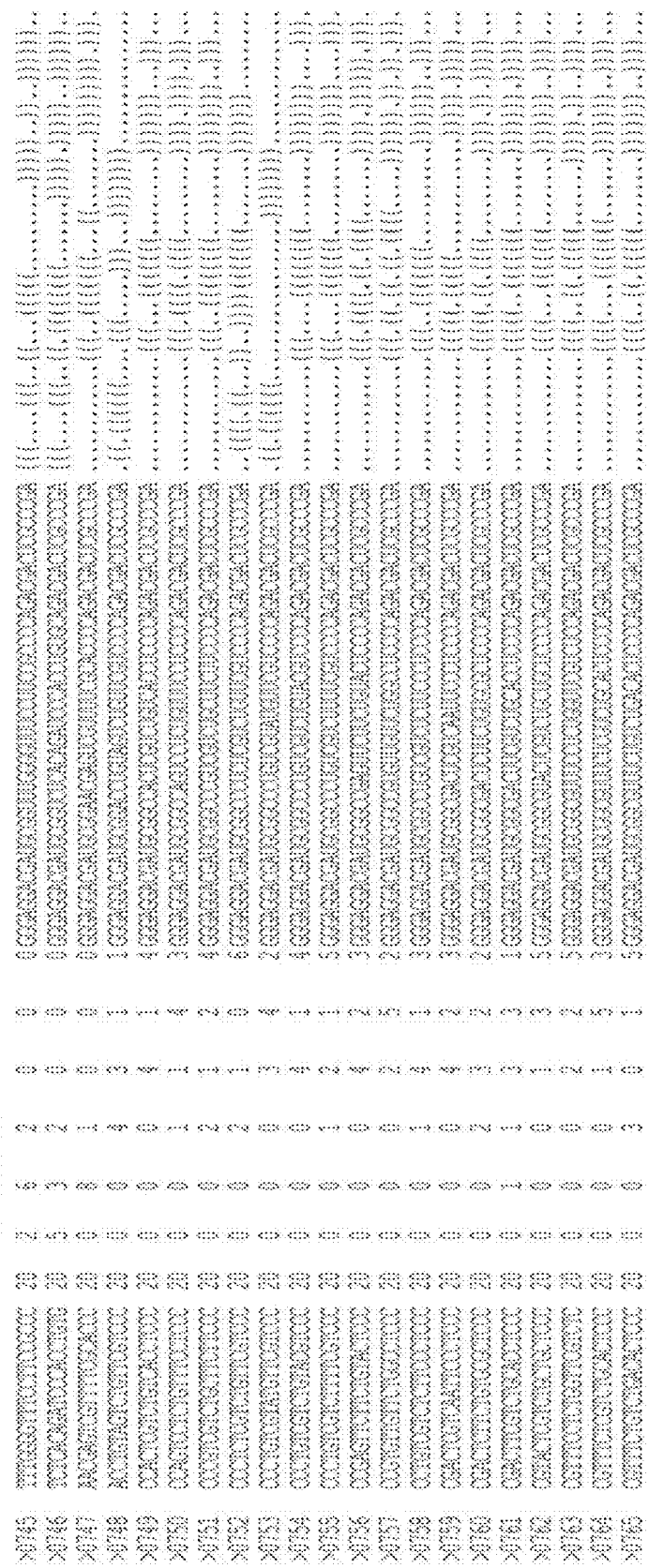

Next, we estimated the % Sequence Complexity at each round of selection by determining the percent of unique reads relative to the total reads (Unique/Total) (data not shown). Sequence Enrichment (% Enrichment) was then determined by taking the complement of % sequence complexity (1-Unique/Total) (FIG. 2B). % Enrichment reached a plateau at round 6 of selection with no further change observed in subsequent rounds. As shown in FIG. 2B, the most pronounced changes in % Enrichment occurred between selection rounds 3 and 5. Specifically, sequence enrichment approximated 50% by round 4 of selection (FIG. 2B). Taken with the data in FIGS. 1A-1E, these findings confirm that selection convergence was achieved.

We next examined RNA structural complexity/diversity by performing secondary structure predictions of the unique and total reads at each round of selection. The RNAfold algorithm of the Vienna Package (v 2.0.0) (43, 44) was used to generate the secondary structure predictions. First, we determined the minimal free energy (kcal/mol) (FIG. 2C) and ensemble free energy (data not shown) of the predicted secondary structures with the highest probability. Interestingly, we observed a decrease in both minimal free energy (kcal/mol) (FIG. 2C) and ensemble free energy (data not shown) with each progressive round of selection. The decrease in minimal free energy (kcal/mol) for the total reads (white squares) was more pronounced compared to that of the unique reads (black squares). These data suggest that the selection scheme enriched for RNA sequences with higher structural stability as compared to non-selected sequences found within round 0, which have a lower structural stability. The decrease in minimal free energy (kcal/mol) stabilized between selection rounds 4 and 6 (FIG. 2C). These data are in agreement with the data in FIGS. 1A-1E and 2B, and suggest that structural convergence may have occurred as early as round 4 of selection.

We hypothesized that the observed decrease in minimum free energy (kcal/mol) in later selection rounds may have resulted from loss of structural diversity. Therefore, structural diversity was assessed by determining the probability (ensemble probability) of the most likely structure for a given sequence (FIG. 2D) and the diversity (ensemble diversity) of structures that a given sequence may assume (FIG. 2E). Ensemble probability (FIG. 2D) and ensemble diversity (FIG. 2E) was determined for both the unique reads (black squares) and total reads (white squares) at each round of selection. We observed a progressive increase in ensemble probability for both the unique reads (black squares) and total reads (white squares) (FIG. 2D). However, as expected, the increase in ensemble probability for the unique reads (black squares) was more pronounced compared to that of the total reads (white squares). We observed a concordant decrease in ensemble diversity with progressive rounds of selection for both the unique (black squares) and total (white squares) reads (FIG. 2E). As expected, the decrease in ensemble diversity was more pronounced for the unique reads (black squares) than for the total reads (white squares). Together, these data suggest that the selection converged towards fewer possible structures with higher structural probability and stability.

Bioinformatics Analysis of HTS Data from Selection Rounds

Previously, we reported that nucleotide (nt) deletions or insertions within the variable region of a DNA or RNA SELEX library can occur during the course of a selection. Therefore, we examined the variable region nucleotide length of unique reads from selection round 0 (gray bars) and round 8 (black bars) (FIG. 3A). As expected, the mode variable region length was 20 nucleotides for both round 0 (gray bars) and round 8 (black bars). However, the average variable region length was significantly ($p<0.001$) higher in round 8 (black bars) compared to round 0 (gray bars) (FIG. 3A). The increase in the average variable region length observed in round 8 (black bars) was most likely due to an increase in frequency of RNA sequences with a 21-nucleotide variable region length. Interestingly, we also observed a higher frequency of sequences with 19-nucleotide variable region length in round 0 which were not present (or likely, were not selected) in later rounds (FIG. 3A). Based on these observations, we included sequences with variable region lengths ranging from 18 to 22 nucleotides in our subsequent analyses.

Figure 3B:
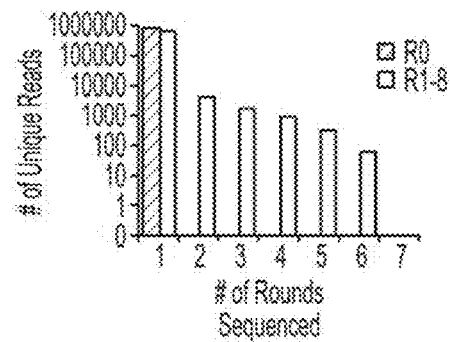

We next analyzed the high-throughput sequencing data to separate true-selected sequences from non-selected sequences. We postulated that rounds 1 through 8 would contain a mixture of true-selected sequences and non-selected sequences, while non-selected sequences would be predominantly found in round 0. First, we examined the recurrence of a given unique read between sequenced rounds by comparing the number of unique reads from round 0 and rounds 1-8 to the number of rounds sequenced (i.e., 7 rounds: rounds 0, 1, 3, 5-8) (FIG. 3B). As expected, all unique reads analyzed were present in at least one sequenced round (FIG. 3B). By contrast, none of the unique reads from rounds 1 through 8 were found in round 0, suggesting that complete coverage of the round 0 library was not achieved through Illumina sequencing, even after sequencing the round 0 library twice (Table 4). Importantly, thousands of unique reads from rounds 1 through 8 where found in two or more rounds, with many unique reads found in as many as six rounds (FIG. 3B). These data suggest that 'true-selected' sequences are more likely to appear in multiple rounds compared to non-selected sequences. Furthermore, the number of rounds in which a unique read is found may be used as a cut-off to separate 'true-selected' sequences from non-selected sequences. In this case, we favored a low-stringency cut-off. For example, we considered a 'true-selected' sequence to be a sequence that was present in at least two or more rounds of selection.

Figure 3C:
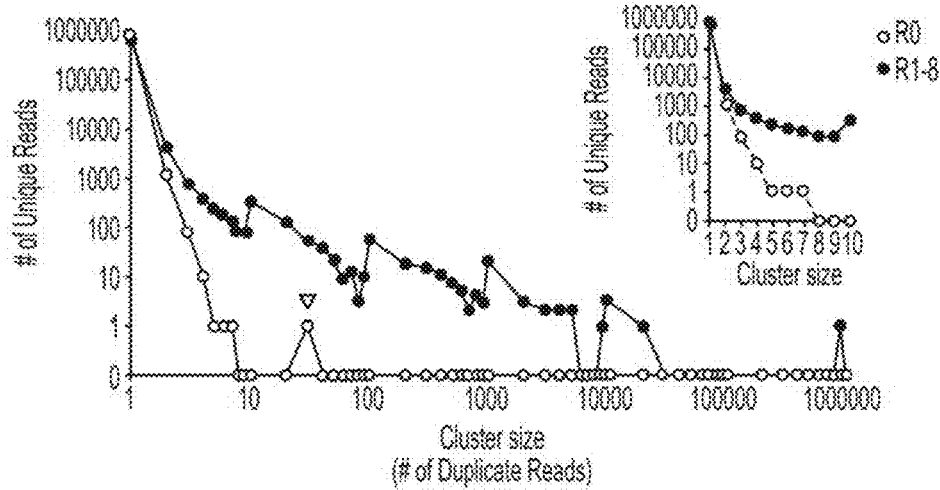

Next, we reasoned that an additional measure of a true selected sequence would be its cluster size, which is the number of duplicate sequence reads in each round. Thus, we compared the number of unique reads within round 0 and rounds 1-8 to cluster size (FIG. 3C). The most represented cluster size for unique reads within rounds 1-8 and round 0 was a cluster size=1 (FIG. 3C). As anticipated, unique reads in round 0 are represented by small cluster sizes (<10 duplicate reads), such that only one unique read within round 0 had a cluster size greater than eight reads (FIG. 3C). However, this unique read contained a continuous string of cytosine and thus was likely a sequencing error that was amplified thirty times (30 reads; ▼). In contrast, unique reads in rounds 1 through 8 are represented by large cluster sizes (>10 duplicate reads) (FIG. 3C). These data suggest that cluster size can be used to separate 'true-selected' sequences from non-selected sequences. In this case, the initial substantial difference in cluster size between unique reads detected in round 0 and rounds 1-8 was observed at cluster size=3 (FIG. 3C, see inset).

Taken together, the number of rounds in which a given sequence is found (FIG. 3B) and its cluster size (FIG. 3C) may be combined to separate 'true selected' sequences from non-selected sequences. Based on these analytical parameters, a 'true selected' sequence from the cell-based VSMC selection described herein is more likely to be present in two or more rounds and have a cluster size of 3 reads. Thus, for subsequent analyses, if a sequence was detected in two or more rounds and had a cluster size of at least three reads, it was considered a 'true selected' sequence.

Edit and Tree Distance Analyses

Figure 4A:
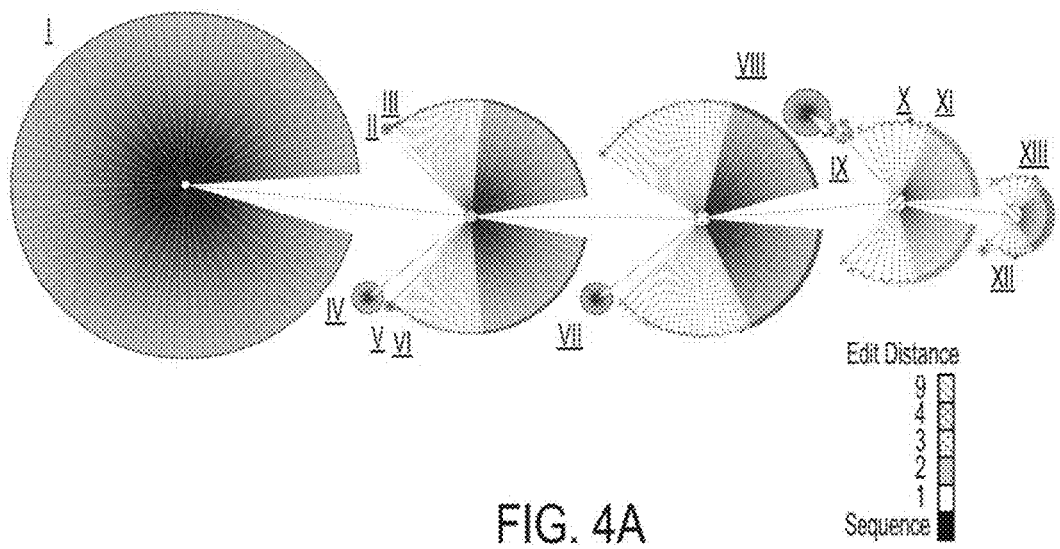
FIGS. 4A-4C. Bioinformatics analysis of RNA aptamers to identify related sequence and structure families. (A) RNA aptamer unique sequences (black) are connected to nodes of increasing edit distance (1-9; blue to red color scale). Related sequence families were identified as RNA aptamer sequences that connected by an edit distance of 1 (I-XIII). (B) RNA aptamer sequences (black) were connected to nodes of increasing tree distance (0-18; blue to red color scale). Related structure families were identified as RNA aptamer sequences with structures connected by a tree distance of 3 to 6 (A-H). (C) Venn Diagram of RNA sequences identified based on the edit distance (27 sequences) and tree distance (31 sequences) analyses. Orphan: a highly represented sequence that did not fall into a sequence or structure family.

Candidate aptamers derived from selection efforts are often categorized based on sequence homology (24, 25) and sequence motifs (8, 46). We have expanded these analyses to include a novel pairwise comparison of each aptamer sequence using the concept of edit distance (FIG. 4A). Edit distance is defined as the number of changes (substitution/insertion/deletion) necessary for two sequences to become identical. For example, closely-related sequences have a low edit distance, while unrelated or loosely-related sequences are denoted by a high edit distance.

Figure 8:
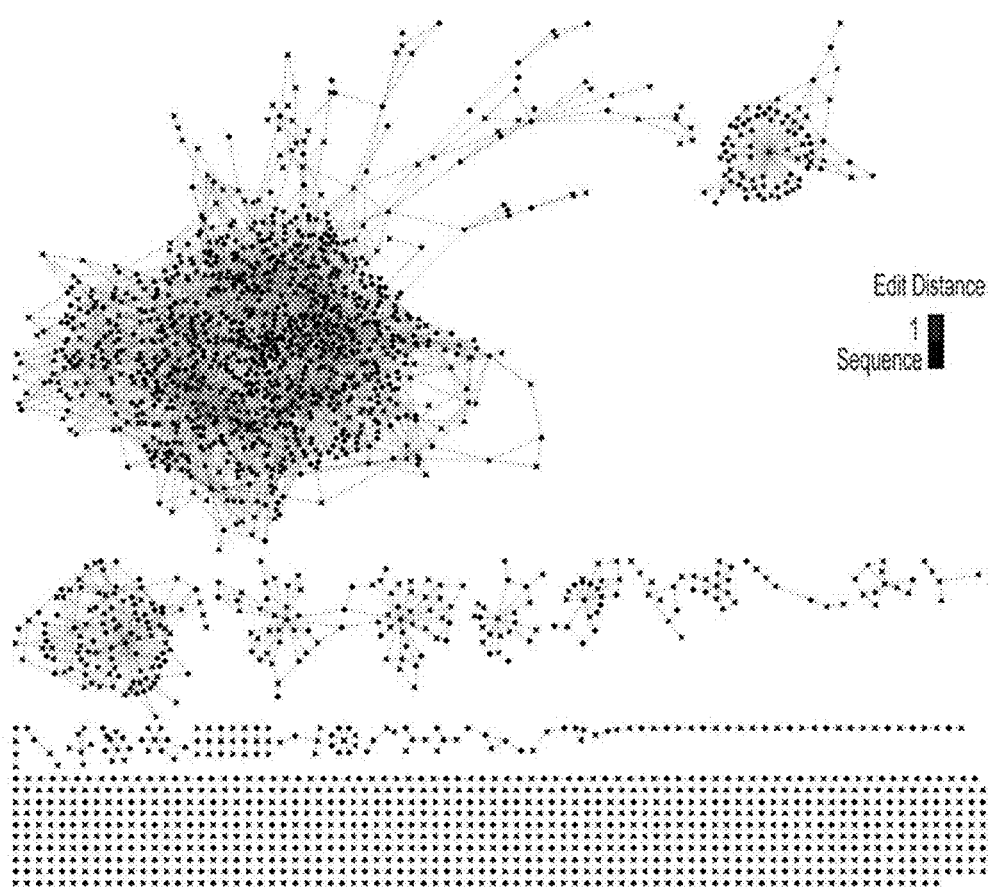
FIG. 8. Edit distance 1 output from process.seqs program. Unique sequences (black nodes) interconnect by edges (lines) at edit distance 1 (blue lines). This analysis resulted in several sequence clusters (1 edit distance apart) as well as orphan sequences that did not fall within a sequence cluster (individual nodes not interconnected by blue lines). This data output was used to generate the dendrogram in FIG. 4A, which depicts the edit distance between each sequence cluster.

We next determined the edit distance for sequences within rounds 1-8 that were categorized as 'true selected' sequences based on the analyses described in FIGS. 3B and C. A total of 2312 unique reads (see excel/CVS data file 1), representing 1,123,533 total reads, were analyzed for edit distance (FIG. 8; output for edit distance=1 shown) by the program process.seqs (FIG. 4A). As seen in FIG. 4A, all unique sequences interconnect at edit distance=9 (red node). Unique sequences that interconnect at edit distance=1 (blue), 2 (cyan), 3 (green), 4 (yellow), and 9 (red) are shown (FIG. 4A). The most significant clustering of sequences was observed at an edit distance of 1. The dendrogram in FIG. 4A was used to identify families of related sequences and to determine how far apart (in edit distance) the sequence families were from each other. At each edit distance node, the robustness of clustering of related sequences was determined using ClustalX multiple sequence alignments (see Methods for details). From these alignments, 13 distinct sequence families (I-XIII) at 1 edit distance apart were established (FIG. 4A).

Figure 4B:
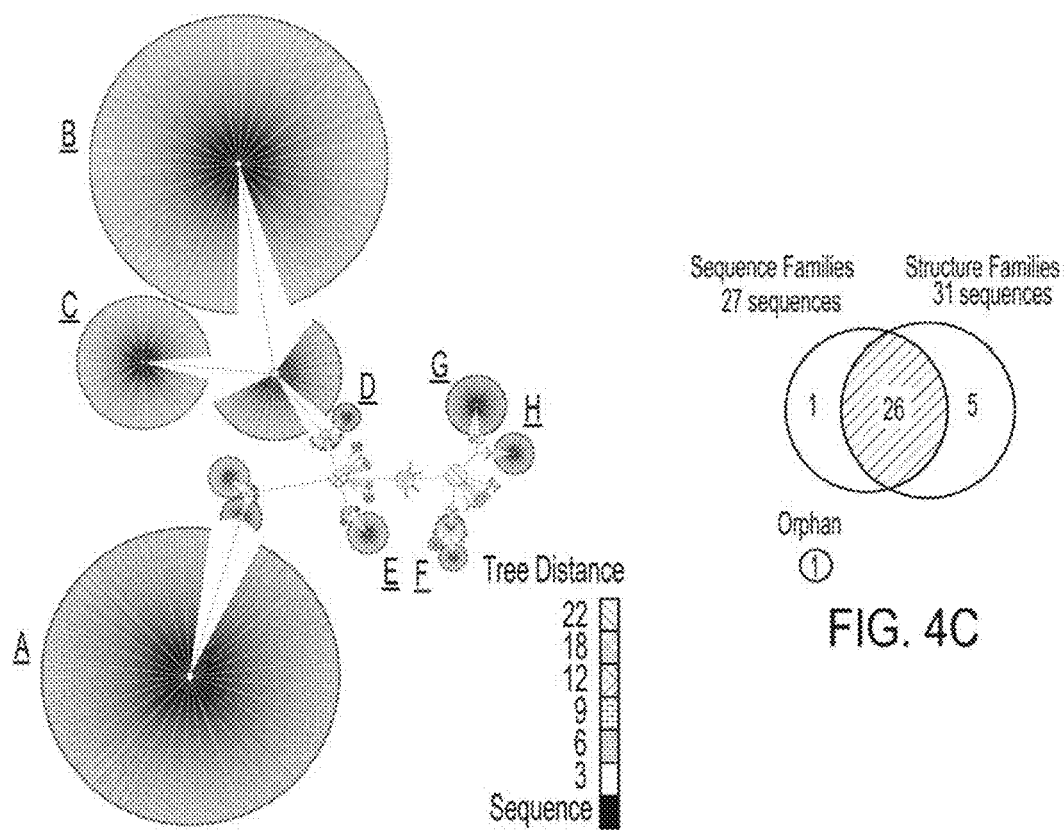
Figure 9:
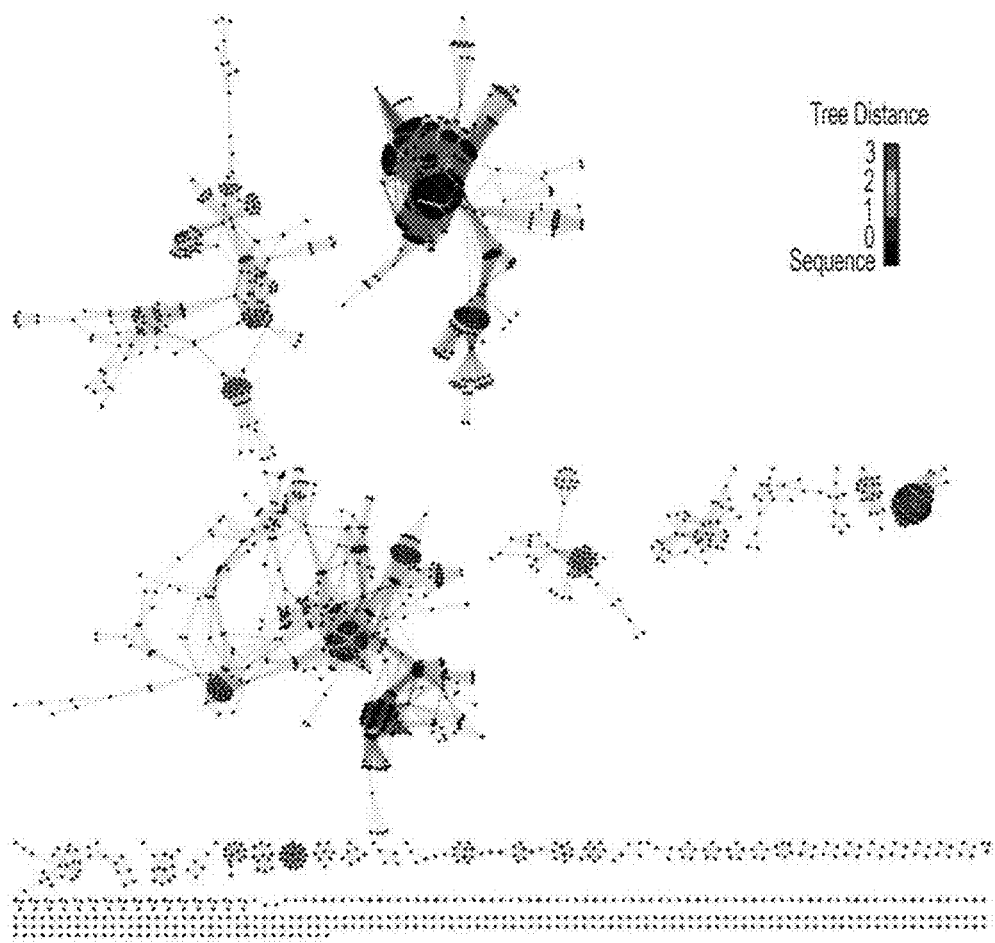
FIG. 9. Unique sequences interconnected by a tree distance=3. Structures of unique sequences (black nodes) interconnect by edges of tree distances 0-3 (0=blue, 1=cyan, 2=green, 3=red). Separate groups of unique sequences with no interconnections are more than 3 tree distances apart.

Although selected aptamers are typically categorized based on sequence similarity, we asked whether selected aptamers could also be analyzed and categorized by structural similarity. The secondary structure with the highest probability for each of the 2312 unique reads (1,123,533 total reads) was predicted using RNAfold. Each unique read was assumed to have only a single structure, which is supported by the data in FIGS. 2D and E that suggest that selected sequences have a higher structural probability and low structural diversity, respectively, when compared to non-selected sequences. A pairwise comparison for each structure was performed using the concept of tree distance, which describes the relatedness of two structures by calculating the dissimilarity between two structures. Analogous with edit distance, closely-related structures have a low tree distance, while unrelated or loosely-related structures are denoted by a large tree distance. Unique sequences were analyzed for tree distance (FIG. 4B). The data output derived from tree distance=3 analysis is shown (FIG. 9). All of the predicted structures connected with tree distances ranging from 0 (representing an identical structure of a different sequence) to 22 (red node). LocARNA multiple sequence/structure alignments of the predicted RNA structures at the various tree distances were used to establish structure families (see Methods for details). Eight structure families (A-H) were identified and ranged from a tree distance of 3 to a tree distance of 6 (FIG. 4B).

Figure 4C:
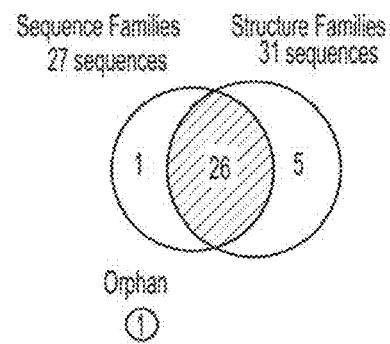

Next, single representative RNA aptamer sequences were selected from each sequence (FIG. 4A) or each structure family (FIG. 4B) based on the following parameters: (1) fold enrichment (8, 46) (2) 'rising', defined by the increasing trend in read number over progressive rounds of selection, (3) read number, defined by total reads in a given round and (4) rate enrichment, defined by the change in read number over change in round number. These parameters were applied to the following rounds: rounds 1-8, 1-3, 3 through 8 and 6 through 8, based on the selection conditions described in Table 1. The analysis of the rounds based on the above parameters resulted in a total of 27 representative aptamer sequences derived from the 13 edit distance sequence families and a total of 31 representative aptamer sequences derived from the eight tree distance structure families (FIG. 4C). Interestingly, while 26 out of 32 the RNA sequences were identified by both methods, some aptamer sequences were only identified by the edit distance analysis (1 out of 32) or the tree distance analysis (5 out of 32) (FIG. 4C). In addition, a single highly represented sequence denoted as 'orphan' (FIG. 4C) did not group with any of the families derived from the edit distance or tree distance analyses. This sequence comprised a total of 506 reads and was chosen, along with the other 32 sequences, for a total of 33 single RNA aptamers for subsequent analysis.

Internalization of Single Aptamers into VSMCs

Figure 5A:
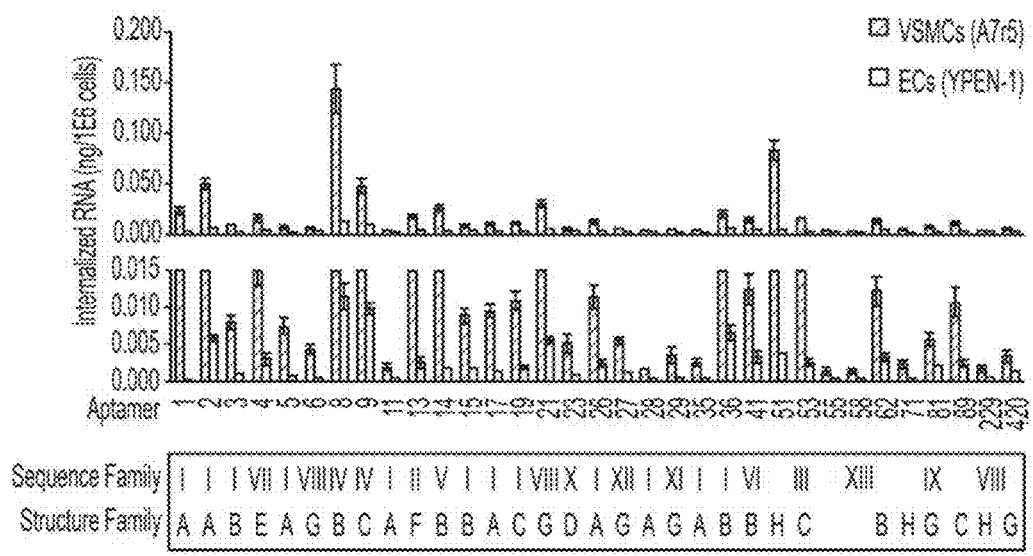
FIGS. 5A-5B. VSMC-specific internalization of candidate RNA aptamers. (A) Internalization of individual RNA aptamer sequences derived from the bioinformatics analysis in FIG. 4 was assessed in both VSMCs and ECs by RT-PCR (RT-qPCR). The data are normalized to a reference control RNA and to cell number. Internalized RNA data (ng/1,000,000 cells) are plotted on a full scale (top panel) as well as on an expanded scale (middle panel). Table (bottom panel) indicates the sequence and/or structure family of each RNA aptamer sequence. (B) Relative fold internalization (VSMCs/ECs) was determined for each RNA aptamer sequence.
Figure 5B:
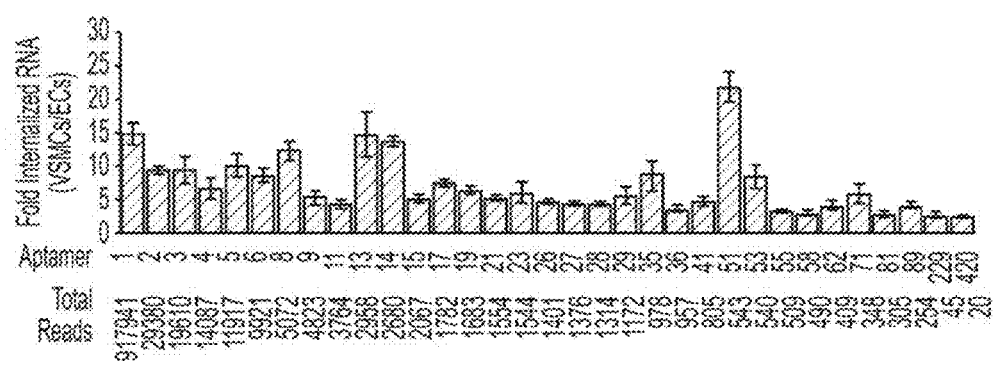

To evaluate aptamer internalization, the 33 individual RNA aptamers identified in FIGS. 4A-4C were incubated with either VSMCs (A7r5) or EC (YPEN-1) cells and the RT-qPCR fold internalization into VSMCs over ECs was calculated after recovery of aptamers (FIGS. 5A, 5B). All tested aptamers internalized preferentially into VSMCs (A7r5) compared to ECs (YPEN-1) (FIG. 5A), though it should be noted that the degree of internalization varied from aptamer to aptamer. Approximately 82% of all screened aptamers displayed in a 4-fold greater internalization into VSMCs compared to ECs. Many of the highest internalizing aptamers were identified by both the edit distance and the tree distance analyses (FIG. 5A). The most represented aptamer, #01 (917,941 total reads) was among the better internalizing sequences (14.8±1.7 fold) (FIG. 5B). Interestingly, the aptamer with the highest fold internalization, #51 (21.8±2.2 fold) was identified only by the tree distance analysis but not the edit distance analysis (FIG. 5A). The 'orphan' aptamer #55 displayed the poorest internalization (fold internalization <4). Together, these data highlight the importance of performing a tree distance analysis in addition to categorizing aptamers based on sequence similarity. Importantly, these data also suggest that aptamers that do not fit into either edit distance or tree distance families are likely to be 'junk' sequences and should not be included in further analyses.

Figure 10:
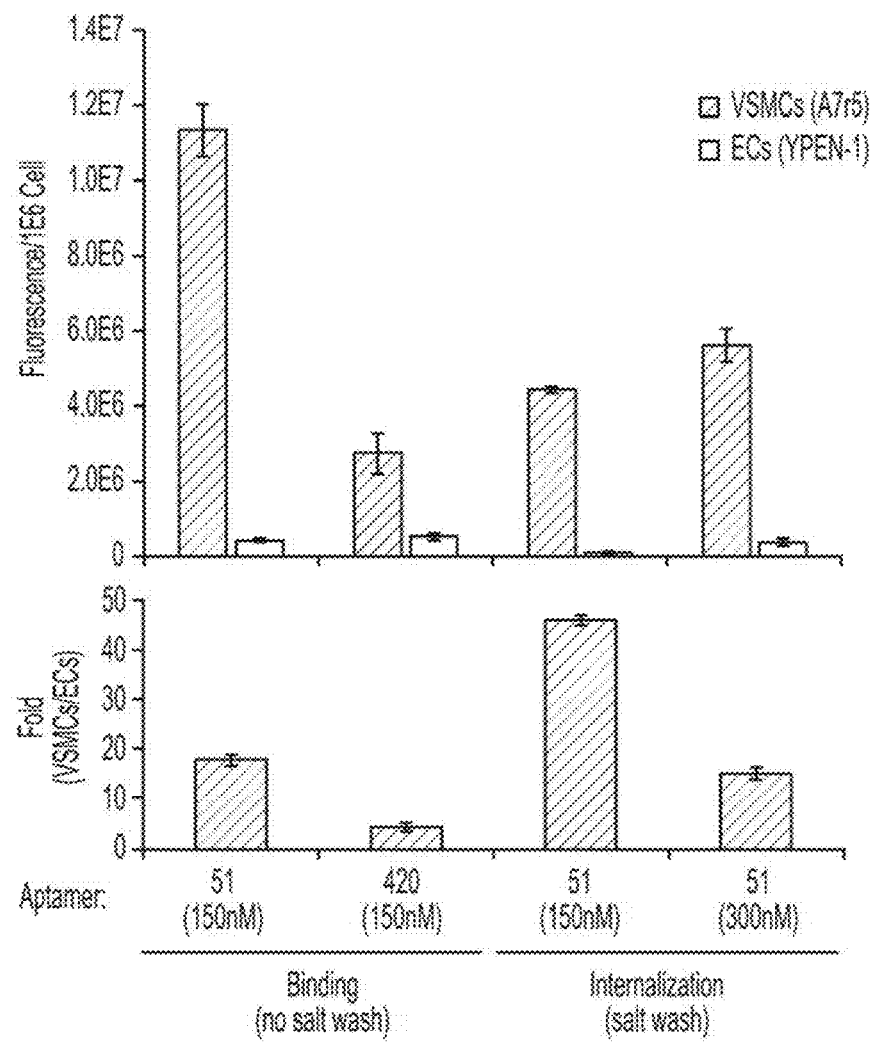
FIG. 10. Binding and internalization of Fam-GTP labeled aptamers. RNA aptamers #51 and #420 were labeled during in vitro transcription with a Fam-GTP. Binding of aptamers #51 and #420 was determined by fluorescence after several PBS washes without high salt. Internalization of aptamer #51 was determined at 150 nM and 300 nM by fluorescence following several PBS washes that included a high salt wash.

Next, we performed a fluorescent-based 'plate reader' assay to confirm specific binding and internalization of our selected aptamers into VSMCs (FIG. 10). We assessed binding/internalization of two independent fluorescently-labeled aptamers (#51 and #420). As observed with the RT-qPCR assay, aptamer #51 is a strong cell-specific internalizer, while aptamer #420 is a weak cell-specific internalizer (FIG. 10). Together, these data confirm that the aptamers selectively internalize into VSMCs vs.ECs.

We used correlation analysis to determine the dependence of fold internalization (into VSMCs) and the following parameters: (1) fold enrichment (8, 46), (2) rising (trend of increasing read number across progressive rounds), (3) rate enrichment and (4) read number (Tables 2 and 3). The correlation analysis determines the dependence between two variables as defined by a correlation coefficient (r) that has a value between −1.0 and 1.0. For example, two variables with a cooperative dependence will have a positive correlation coefficient (r>0), whereas two variables with an opposing dependence will have a negative correlation coefficient (r<0). The correlation analysis also calculates the statistical significance (p-value) of the relationship between two variables as described by the correlation coefficient.

Significant positive correlation coefficients (r>0 and p<0.05) were obtained when comparing fold internalization to fold enrichment for rounds 1 through 8 and rounds 3 through 8 but not for rounds 1 through 3 and rounds 6 through 8. Similar results were obtained when comparing fold internalization to rate enrichment (Table 2). These results suggest that cell-specific internalizing aptamers are enriched after the inclusion of a negative selection step (round 4) and that further enrichment occurs after the selection has converged (rounds 6 through 8) (Table 2 and FIGS. 1B and 1C). In general, fold internalization positively correlated with fold enrichment (Table 2), read number (Table 3) and rate enrichment (Table 2) only after round 3 of selection, when the negative selection (performed against ECs) was introduced (Table 1). In contrast, no significant correlation was found between fold internalization and rising (Table 2). These data suggest increasing read number between rounds is not sufficient to denote specific internalization. These data collectively suggest that the above parameters coupled to selection conditions should be analyzed in order to facilitate the identification of 'winner' sequences.

TABLE 2

Correlation coefficient (r) for fold internalization vs. fold enrichment, 'rising' and rate enrichment.

| Rounds | Fold enrichment | | 'Rising' | | Rate enrichment | |
| --- | --- | --- | --- | --- | --- | --- |
| | r | p | r | p | r | p |
| 1-3 | 0.20 | 0.341 | | | 0.02 | 0.916 |
| 1-8 | 0.52* | 0.010 | 0.27 | 0.195 | 0.54* | 0.007 |
| 3-8 | 0.47* | 0.021 | 0.36 | 0.084 | 0.50* | 0.013 |
| 6-8 | 0.35 | 0.095 | 0.18 | 0.397 | 0.26 | 0.215 |

*p < 0.05

TABLE 3

Correlation coefficient (r) for fold internalization vs. read number

| Round | r | p |
| --- | --- | --- |
| 1 | −0.07 | 0.739 |
| 3 | 0.00 | 0.995 |
| 5 | 0.43* | 0.037 |
| 6 | 0.55* | 0.005 |
| 7 | 0.69* | 0.000 |
| 8 | 0.62* | 0.001 |
| Total | 0.70* | 0.0001 |

*p < 0.05

Discussion

The identification of candidate aptamer sequences within an enriched library is slowly shifting from traditional cloning and sequencing approaches to the use of HTS (8, 18, 24, 45-48). In spite of this trend towards more sophisticated aptamer identification approaches, the computational tools for the downstream analysis of millions of sequence reads, which result from HTS efforts, are still being streamlined. Here we describe a novel approach that couples HTS with bioinformatics tools to facilitate the identification of over 30 'winner' RNA sequences from a complex, cell-internalization aptamer selection. To identify candidate aptamer sequences, high-throughput sequence data from eight rounds of negative and positive selection were analyzed using these novel methods. Metrics for determining % Enrichment confirmed the experimental cell-internalization data suggesting the selection was complete after eight rounds of selection. Millions of 'true-selected' sequences were separated from the non-selected ones using metrics based on the number of rounds a sequence was present in and on the cluster size for each sequence. The metrics analysis for selection enrichment made it possible to sort through millions of reads and rapidly eliminate those sequences that were not selected or were present in the dataset as a result of sequencing errors. All the unique reads that comprised the 'true-selected' sequences were then clustered based on either sequence similarity using edit distance analysis or structural similarity using tree distance analysis. Importantly, these analyses resulted in the identification of sequences that would otherwise have been missed by conventional means, that is, by selecting only the top sequence reads.

The approach described herein, is of importance in light of the rise in complex target SELEX, in which aptamers are directly selected against complex protein mixtures, cells, or even whole organisms (24, 33, 36, 49-53). Many of the cell-specific aptamers generated so far have served well as neutralizing ligands (21), real-time detection probes (54, 55), as well as internalizing escorts (24). Particularly impressive, are selections performed against whole organisms (in vivo-SELEX) that include the isolation of RNA aptamers that recognize African trypanosomes (51) and *Mycobacterium tuberculosis* (52). These aptamers have the potential to target biomarkers on the surface of the parasite or bacterium and as such might be modified to function as novel drugs against these unicellular organisms. While African trypanosomes and *Mycobacterium* tuberculosis are examples of simple, unicellular organisms, complex in vivo-selections have also been attempted in order to isolate aptamers against intrahepatic carcinomas in mice (53). In this work, the authors performed intravenous injections of chemically modified RNA pools into tumor bearing mice. Those aptamers that localized to the tumors were extracted and amplified. These efforts resulted in two RNA sequences that target an intracellular, RNA binding protein (P68) overexpressed in the hepatic tumor.

Despite the complex nature of published aptamer selections, the resulting 'winner' aptamer sequences are typically few in number and, in most cases, only one sequence is identified and further characterized. The likely reason for the "one selection-one aptamer" phenomenon is that only the most highly represented sequences are sequenced using the traditional chain terminator method, i.e., Sanger sequencing (33, 36, 49-52, 56). Recently, the advent of HTS technologies has streamlined the sequencing process, allowing researchers to obtain a more comprehensive picture of all selected sequences after only a few rounds of selection (8, 18, 45, 46). Although these published studies were performed against purified, recombinant proteins, the authors observed that the sequences with the highest read number were not necessarily the highest affinity binders (8, 46). By contrast, high affinity binders had the highest fold enrichment during the course of the selection (8, 46). These findings are in agreement with our data demonstrating that cell-specific internalization of 'winner' sequences positively correlated with fold enrichment. Interestingly, although we also observed a positive correlation between fold internalization and read number, this association occurred only after the introduction of a negative selection step. Together, these studies highlight the importance of performing HTS on all rounds of selection in order to assess fold enrichment of specific sequences over the course of a selection. In addition, our data identify the negative-selection step as a key criterion to successfully enrich for cell-specific sequences (24).

To date, bioinformatics analyses performed on aptamer selections have relied predominantly on an arbitrary cutoff, typically based on read number, to identify aptamers sequences that are subsequently analyzed experimentally (8, 24, 45). While this strategy has proven effective, candidate sequences with a low read number are have a high probability of being missed or disregarded. In order to identify all possible 'winner' sequences, including those that were not highly-represented, we performed pairwise comparisons using edit distance and tree distance analyses to identify sequences that are related based on sequence or structure. These analyses resulted in the identification of 27 sequences (out of 32) that were among the best cell-specific internalizing aptamers (fold internalization≥4). Of particular importance, the aptamer with the highest fold internalization (#51) was not among the aptamers with the highest read number. Aptamer #51 was identified only through the tree distance analysis, highlighting that RNA structure should also be considered when choosing sequences for experimental validations.

A potential current limitation of the tree distance analysis is that it is based on the assumption that each sequence has only a single predicted structure. While RNA molecules can assume multiple breathing dynamics, our data seem to indicate that structural diversity decreases over the course of a selection. However, the inclusion of all possible RNA structures may improve the outcome of current tree distance analyses, though this type of analysis is currently hindered by the existing algorithms for structure prediction. Indeed, we anticipate these multi-structure analyses are likely to become more feasible as predictive RNA structural algorithms evolve and as computational algorithms become more complex.

In conclusion, our studies highlight the utility of combining HTS with bioinformatics analysis for the identification of 'winner' sequences from an aptamer selection performed against a complex target. These efforts have yielded (1) predictive tools that are broadly applicable to all aptamer selections for target sequence identification; and (2) several VSMC-specific RNA aptamers that can subsequently be used for targeted delivery.

Materials & Methods

Cell Culture

All cell lines were cultured at 37° C. under 5% $CO_2$. The A7r5 (ATCC, CRL-1444) cell line was cultured in DMEM (Gibco, 11965) supplemented with 10% heat inactivated FBS (Atlanta biologicals, S11550) and the YPEN-1 (ATCC, CRL-2222) cell line was cultured in MEM (Gibco, 11095)

supplemented with 5% heat inactivated FBS (Atlanta biologicals, S11550), 1.5 g/L Na bicarbonate (Gibco, 25080), 0.1 mM MEM NEAA (Gibco, 11140), 1.0 mM Na pyruvate (Gibco, 11360) and 0.03 mg/mL heparin (Sigma, H4784). All cell lines were screened for contamination by mycoplasma, which is known to degrade 2'-fluoro pyrimidine modified RNA aptamers (57). Both cell lines were split 1:3 or 1:4 upon reaching confluence by washing with DPBS (Gibco, 14190-144) and detaching cells using 0.25% Trypsin-EDTA (Gibco, 25200) as recommended for each cell line by ATCC. Each cell line was carried for no more than 5-6 passages. For selection rounds and internalization assays, confluent P150 (Nunc, 168381) plates of A7r5 and YPEN-1 were detached as described. Cells were counted by staining an aliquot of cells with 0.4% trypan blue (Gibco, 0618) and using a hemocytometer to count the number of live cells. A7r5 and YPEN-1 cells were plated at 5 million and 8 million cells per P150 respectively for selection rounds and 500,000 and 800,000 cells per well of a 6-well plate respectively for internalization assays. For internalization assay, extra A7r5 and YPEN-1 cells were plated in order to count the number of cells after 24 hrs in culture to normalize internalization assay data to cell number.

Cell Internalization SELEX

Generation of the Initial (Round 0) RNA Library

The duplex DNA library was generated as follows. The Sel2N20 single stranded DNA (ssDNA) template oligo, 5'-TCGGGCGAGTCGTCTG-N20-CCGCATCGTC-CTCCC-3' (SEQ ID NO: 3) (IDT, Coralville, Iowa) was extended using Choice Taq Polymerase (Denville Scientific Inc., CB4050-2) in the presence of Sel2 5' primer, 5'-TAATACGACTCACTATAGGGAGGACGATGCGG-3' (SEQ ID NO: 4). The extension reaction was performed in a thermocyler by heating the Sel2N20 ssDNA template oligo and the primer at 95° C. for 3 min, annealing at 25° C. for 10 min and extending at 72° C. for 30 min, followed by a 10 min incubation at 25° C. The duplex DNA library was in vitro transcribed for 16 hrs at 37° C. using Y639F mutant T7 RNAP (58-59) to enable incorporation of 2'-OH purines (Roche; GTP, 14611221; ATP, 14919320) and 2'-Fluoro pyrimidines (TriLink BioTechnologies; 2'-Fluoro-2'-dCTP, N-1010-020509; 2f-Fluoro-2'-dUTP, N-1008-013008) in the Round 0 RNA library. During the transcription reaction, the final concentration of rNTPs for targeted selections was 4 mM with a 3:1 ratio of 2'-F pyrimidines to 2'-OH purines (3 mM 2'-F pyrimidines and 1 mM 2'-OH purines). Duplex DNA was removed from the transcription reaction using DNase I (Roche, 04716728001) and the RNA from the transcription reaction was run on a denaturing gel (10% acrylamide; 7M urea). The band of RNA was detected by UV shadowing and excised from the gel. The excised gel fragment containing the RNA was incubated with TE buffer to elute the RNA from the gel. Eluted RNA was collected using a 10,000 MWCO centrifugal filter (Amicon Ultra-4, UFC801024) and washed with additional TE buffer. The concentration and purity of the extracted RNA was determined by OD 260/280.

Cell-Internalization SELEX for VSMC Specific Internalizling Aptamer Selection

We applied a modified cell-based SELEX (21) termed cell-internalization SELEX as previously described (24). A7r5 and YPEN-1 cells were cultured as described under cell culture methods. For each round of selection, 150 nM RNA was folded in Opti-MEM (1500 pmoles in 10 mL) by heating to 65° C. for 10 min followed by a 20 min incubation at 37° C. Folded RNA was then supplemented with 100 μg/mL yeast tRNA (Invitrogen). A7r5 and YPEN-1 cells were washed 3× with Opti-MEM (Gibco, 31985) and incubated in Opti-MEM with 100 μg/mL tRNA (Invitrogen, 15401-029) in Opti-MEM for 15 min. For rounds 1 through 3, the RNA library was added to A7r5 cells for 90 min. For rounds 4 through 6, the RNA library was pre-cleared against a single plate of YPEN-1 cells for 15 min. For rounds 7 through 8, the RNA library was pre-cleared against two plates of YPEN-1 for 15 min sequentially. For rounds 4 through 6 and 7 through 8, the unbound RNA (from pre-clear step) was collected, centrifuged (1,500 rpm, 5 min.) to pellet cell debris and added to A7r5 cells for 60 min and 30 min respectively. YPEN-1 pre-clear conditions (time and number of plates) and A7r5 selection conditions (internalization time) are summarized in Table 1.

Following incubation of the RNA library, A7r5 cells were washed 3 times with ice cold DPBS to remove unbound RNA. Cell-surface bound RNA was removed by washing cells once with ice cold 0.5 M NaCl DPBS, incubating cells 5 min at 4° C. with ice cold 0.5 M NaCl DPBS and washing once with ice cold DPBS. Internalized RNA was recovered by TRIzol (Invitrogen, 15596-026) extraction by following the manufacturer's instructions. The recovered RNA aptamers were reverse transcribed (RT) (Invitrogen, Superscript III, 56575) using the Sel2 3' primer: 5'-TCGGGC-GAGTCGTCTG-3' (SEQ ID NO: 5). The RT protocol is as follows: 55° C. for 60 min followed by a 15 min incubation at 72° C. The RT product was PCR-amplified using Choice Taq DNA polymerase (Denville Scientific Inc., CB4050-2) in the presence of the Sel2 5' and Sel2 3' primers. The dNTP concentration in the PCR reaction was 2.5 mM (10 mM dNTP mix, Invitrogen, 100004893). The PCR amplification protocol is as follows. 95° C. for 2 min, followed by 25 cycles of heating to 95° C. for 30 sec, 55° C. for 30 sec and 72° C. 30 sec. A final extension step was performed for 5 min at 72° C. The DNA duplex library was in vitro transcribed as described above.

DNA Melt Assay

We used a modified DiStRO method (42) DNA melt assay to determine library complexity. SYBR green (BioRad, 170-8882) was added at a 1:1 volume to 0.5 μM DNA duplex library of each selection round in triplicate. These samples were run on a real-time PCR machine (Eppendorf, Mastercycler epgradient S with realplex$^2$) using a DNA melt assay protocol (95° C. for 15 min; 95° C. for 15 sec; 95° C.-25° C. ramp for 20 min and 25° C. for 15 sec; 4° C. hold). The raw DNA melt assay data (performed in triplicate) was averaged and plotted as fluorescence intensity (SYBR) vs. temperature (C°). Higher library complexity was indicated by a relative shift of the DNA melt curve towards lower temperatures, whereas, lower library complexity was a shift to higher temperatures.

Internalization Assay by Quantitative Reverse Transcription-PCR (RT-qPCR)

Figure 7:
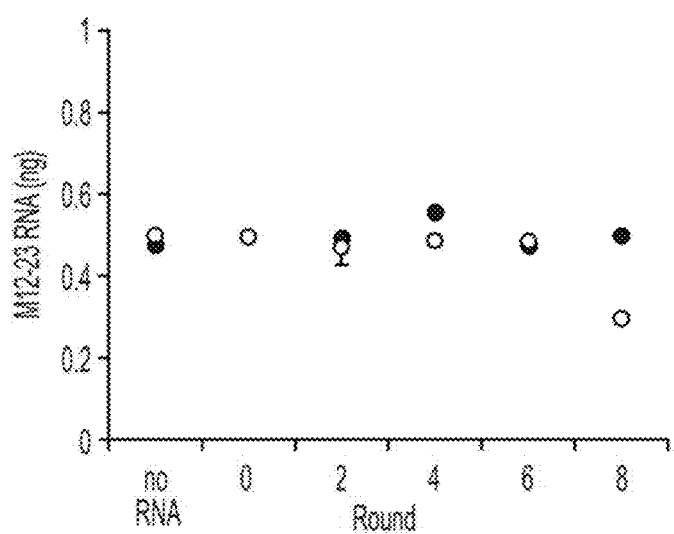
FIG. 7. Recovery of RNA processing control. The M12-23 reference control RNA was added to TRIzol prior to cell lysis as a control for processing of internalized RNA. The reference control M12-23 RNA was measured by RT-qPCR. Internalized RNA data was normalized to each paired processing M12-23 reference control RNA.

We applied similar RT-qPCR methods to detect internalized RNA as described previously (24, 60). A7r5 and YPEN-1 cells were incubated with 150 nM RNA aptamer library (rounds 0 through 8) or 150 nM RNA aptamer for 30 min. at 37° C. with 5% $CO_2$. Unbound and cell-surface bound RNA was removed by washing with ice-cold 0.5M NaCl DPBS. Internalized RNA was recovered by TRIzol containing 0.5 pmoles/mL M12-23 aptamer (61) as a reference control. The amount of recovered RNA was determined by performing a two-step RT-qPCR protocol. In Step one, recovered RNA was reverse transcribed using MMuLV, NEB, M0253L. The primers for the RT step were either the Sel2 3' primer or M12-23 aptamer reference control primer (5'-GGGGGGATCCAGTACTATCGACCTCTGGGT- TATG-3') (SEQ ID NO: 6). The RT protocol is as follows. The recovered RNA and the primers were heated at 65° C. for 5 min, annealed at 22° C. for 5 min and extended at 42° C. for 30 min followed by and extension at 48° C. for 30 min. In Step two, the product from the RT reaction was PCR amplified with iQ SYBR Green Supermix (BioRad, 170-8882) using a Eppendorf Mastercycler epgradient S with realplex[2]. The qPCR protocol is as follows. The RT product was heated at 95° C. for 2 min, followed by 50 cycles of heating at 95° C. for 30 sec, annealing at 55° C. for 30 sec, and extending at 72° C. for 30 sec. A melt curve was performed by heating at 60° C.-95° C. for 20 min. Reactions were all done in 50 μL volume in triplicate with either the Sel2 5' and 3' primers or M12-23 aptamer reference control 5' (5'-GGGGGAATTCTAATACGACTCACTATAGGGA-GAGAGGAAGAGGGATGGG-3') (SEQ ID NO: 7) and 3' primers. Data were normalized to the M12-23 reference control (FIG. 7) and to cell number as determined by counting cells cultured in conjunction with each experiment.

Illumina High-Throughput Sequencing Sample Preparation

Illumina High-Throughput Sequencing Sample Preparation

The RNA pools for selection rounds 0 (in duplicate), 1, 3, 5, 6, 7 and 8 were reverse transcribed using Superscript III (Invitrogen, 56575) in the presence of the Sel2 3' primer. The RT protocol is as follows. The round RNA was heated at 55° C. for 60 min and extended at 72° C. for 15 min. The product from the RT reaction was PCR amplified using Choice Taq DNA Polymerase (Denville Scientific Inc., CB4050-2) in the presence of Illumina primers (5'-AATGATACGGCGAC-CACCGAGATCTACACTCTTTCCCTACAC-GACGCTCTTCCGATC T-8nt Barcode-GGGAGGAC-GATGCGG-3' (SEQ ID NO: 8); 5'-CAAGCAGAAGACGGCATACGAGCTCTTC-CGATCTTCGGGCGAGTCGTCTG-3' (SEQ ID NO: 9)). The PCR Protocol is as follows. The RT product was heated at 95° C. for 2 min, followed by 10 cycles of heating at 95° C. for 30 sec, annealing at 55° C. for 30 sec and extending at 72° C. for 30 sec and a final extension step at 72° C. for 5 min. The PCR product was run on a 2.5% agarose gel and the appropriate band (~151 bp) was excised, gel purified and quantitated using a UV spectrophotometer (OD 260). Samples were combined at equal molar amounts and submitted for Illumina sequencing (Iowa State University DNA Facility, Ames, Iowa; Illumina Genome Analyzer II).

Illumina High-Throughput Sequencing Data Pre-Processing

The Illumina base calls were pre-processed and filtered to identify the variable region sequence as previously described (24, 48). These data (total sequences) included all variable region sequences, including replicates, for a given round of selection. The total sequences were collapsed to individual sequences with total associated reads for each individual sequence. These data (unique sequences) include the different variable region sequences for a given round and the read number (cluster size) associated with each sequence. The unique sequences and total sequences were then converted from DNA code to RNA code and the 5'/3' constant regions were added to give the full length RNA aptamer sequence. Table 4 summarizes the Illumina data obtained and the data filtered during pre-processing (Table 4).

Bioinformatics Analyses

Sequence Complexity and Sequence Enrichment

Sequence complexity was determined using the equation; sequence complexity=unique sequences/total sequences. Sequence enrichment was calculated by taking the complement of % sequence complexity using the equation; sequence enrichment=1-(unique sequences/total sequences). Unique sequences and total sequences refer to the data obtained during Illumina high-throughput sequencing data pre-processing.

Minimum Free Energy, Ensemble Free Energy, Ensemble Probability and Ensemble Diversity The set of unique sequences found within each round were analyzed with RNAfold (43, 62-64) (-T 30, -noLP, -noGU, -d2) from Vienna Package v2.0.0 (43, 44). A program (process_seqs_rnaFold) was created to allow for batch processing of sequences with RNAfold and included RNAfold data output in a comma delimited format. The average and SEM for minimum free energy (kcal/mol), ensemble free energy (kcal/mol), ensemble probability (Probability, %) and ensemble diversity (Diversity, #) were calculated. For the set of total sequences the averages and SEM were recalculated using the read number for each unique sequence.

Variable Region Length, Frequency of Sequences Between Rounds and Frequency of Cluster Sizes A non-redundant database was created of all unique sequences found within the rounds of selection (rounds 0, 1, 3, 5, 6, 7, 8). For each sequence, this database tracked the variable region nucleotide (nt) length (minimum=1 nt, maximum=56 nt), the number of rounds the sequence was identified in (minimum=1 round; maximum=7 rounds) and the read number (cluster size) of the sequence (minimum=1 read, maximum=956,532 reads). Using this database; the average, SEM, mode, maximum, minimum and frequency of the variable region nucleotide length was determined for each round; the frequency of the number of rounds sequences were found was determined for round 0 and rounds 1 through 8; the frequency of cluster sizes was determined for round 0 and rounds 1 through 8.

Sequence Families and Structure Families

A program (process.seqs) was created that used RNAfold and RNAdistance from the Vienna Package (v 2.0.0) (43, 44) to first predict the most likely structure and to second determine the edit/tree distance of all sequences/structures to each other. The program process.seqs filtered these data using a predefined limit on either edit distance (FIG. 8; data output for edit distance=1) or tree distance (FIG. 9; data output for tree distance=3). Process.seqs was run using increasing values of edit/tree distance to determine the maximum edit/tree distance where all sequences/structures connected. Clusters of sequences/structures interconnected at each edit/tree distance were determined and separated using the program Cytoscape (v 2.8.1). Using these data, a dendrogram of sequence/structure relatedness by edit/tree distance was created and the resulting dendrogram was evaluated using Cytoscape. The edit/tree distance dendrogram indicates the edit/tree distance that the unique sequences interconnect. Sequence/structure families were evaluated at each edit/tree distance using the multiple sequence alignment program ClustalX (v 2.1) or multiple RNA structure alignment program LocARNA (webserver).

Calculations for Rising, Fold Enrichment and Rate Enrichment

The previously described non-redundant database was used to normalize the read number of each sequence from a given round to the total reads from all rounds. To avoid dividing by 0 and simplify calculations, a read number of 1 was assumed with sequences with a read number of 0. The rising, fold enrichment and rate enrichment was determined for all unique sequence between rounds 1 through 3, 1 through 8, 3 through 8 and 6 through 8. 'Rising' was determined by calculating the correlation coefficient (−1.0 through 1.0) for each sequence using the read number and round number. Fold enrichment was determined by dividing the number of reads in a given rounds with the read number in a previous round. Rate enrichment was calculated by dividing the change in number of reads by the change in round number.

Plotting and Statistics

Data were plotted using either Microsoft Excel 2010 or GraphPad Prism 5. Average, SEM, mode and correlation were determined using Microsoft Excel 2010. Curve fitting was done using GraphPad Prism 5. Student's t-test was done using Microsoft Excel 2010 with significance set at a p value of <0.05. Correlation coefficients were determined using GraphPad Prism 5 by first determining normality and then the Spearman's correlation coefficient. Significance of the correlation coefficient was determined at a two-tailed p-value of <0.05.

Binding and Internalization Assay by Fluorescence of Fam-G Labeled RNA Aptamers

We used a modified version of the quantitative uptake method previously described (65). Fam-G labeled RNA was in vitro transcribed with the addition of 3 mM 6-FaM GTP (TriLink BioTechnologies) and purified using the same methods as previously described (24,66). Cells (A7r5 and YPEN-1) were prepared and blocked with tRNA as described for under the internalization assay by RT-qPCR methods. A "no RNA" control was included for each cell type to determine background fluorescence of the cell lysate. The Fam-G labeled RNA aptamers were folded in OPTI-MEM at 150 nM using the following modified RNA folding protocol; 98° C. for 10 min.; 65° C. for 15 min.; 37° C. for 20 min. The tRNA block was discarded and Fam-G labeled aptamers were added to cells for 30 minutes. Following RNA aptamer incubation, all samples, including the "no RNA" control, were washed 4× using one of two protocols to determine either binding or internalization. Washes for binding assay (no salt wash): 2× ice cold DPBS, 1× ice cold DPBS with 5 min. 4° C. incubation, 1× ice cold DPBS. Washes for internalization assay (salt wash): 1× ice cold DPBS, 1× ice cold 0.5M NaCl DPBS, 1× ice cold 0.5M NaCl DPBS with 5 min. 4° C. incubation, 1× ice cold DPBS. Following washes all samples had 600 uL 0.1M NaOH added to lyse cells. During lysis, the cell number control was collected and counted for each cell type as described previously. Cell lysate was collected using a cell scraper into 1.5 mL microcentrofuge tubes. Genomic DNA was sheared by sonication, level 2 for 10 seconds (Fisher Scientific Sonic Dimembrator Model 100). Insoluble protein was pelleted by centrifugation for 10 minutes at 10,000 g at room temperature. Lysate was aliquoted (100 uL) into a black 96-well plate (Nunc #237105) and fluorescence (LjL BioSciences Analyst HT 96.384; Fluorescein Protocol: 1 mm depth, 485-20 excitation, 530-25 emission) of each sample was determined. Fluorescence data was analyzed by subtracting background fluorescence measured from the "no RNA" control, normalizing to cell number, calculating the average and calculating the SEM.

TABLE 4

High-throughput sequencing data summary

| Round | Unfiltered (#) | Removed (#) | Filtered (%) | Total Reads (#) | Unique Reads (#) | Sequence Enrichment (%) |
|---|---|---|---|---|---|---|
| 0 | 285,103 | 5,775 | 2.03 | 279,328 | 278,929 | 0.14 |
| 0 | 528,852 | 11,405 | 2.16 | 517,447 | 516,475 | 0.19 |
| 1 | 366,528 | 8,856 | 2.42 | 357,672 | 353,246 | 1.24 |
| 3 | 286,540 | 7,016 | 2.45 | 279,524 | 224,842 | 19.56 |
| 5 | 319,642 | 6,806 | 2.13 | 312,836 | 33,259 | 89.37 |
| 6 | 321,715 | 6,940 | 2.16 | 314,775 | 8,264 | 97.37 |
| 7 | 260,986 | 6,330 | 2.43 | 254,656 | 6,836 | 97.32 |
| 8 | 235,673 | 5,141 | 2.18 | 230,532 | 4,113 | 98.22 |
| Total | 2,605,039 | 58,269 | 2.23 | 2,546,770 | 1,425,964 | |

REFERENCES

1. Thiel K W, Giangrande P H (2009) Therapeutic Applications of DNA and RNA Aptamers. Oligonucleotides 19: 209-222.
2. Keefe A D, Pai S, Ellington A (2010) Aptamers as therapeutics. Nat Rev Drug Discov 9: 537-550.
3. Tuerk C, Gold L (1990) Systematic evolution of ligands by exponential enrichment: RNA ligands to bacteriophage T4 DNA polymerase. Science 249: 505-510.
4. Ellington A D, Szostak J W (1990) In vitro selection of RNA molecules that bind specific ligands. Nature 346: 818-822.
5. Martell R E, Nevins J R, Sullenger B A (2002) Optimizing aptamer activity for gene therapy applications using expression cassette SELEX. Mol Ther 6: 30-34.
6. Giangrande P H, Zhang J, Tanner A, Eckhart A D, Rempel R E, et al. (2007) Distinct roles of E2F proteins in vascular smooth muscle cell proliferation and intimal hyperplasia. Proceedings of the National Academy of Sciences 104: 12988-12993.
7. Lebruska L L, Maher L J, 3rd (1999) Selection and characterization of an RNA decoy for transcription factor NF-kappa B. Biochemistry 38: 3168-3174.
8. Cho M, Xiao Y, Nie J, Stewart R, Csordas A T, et al. (2010) Quantitative selection of DNA aptamers through microfluidic selection and high-throughput sequencing. Proc Natl Acad Sci USA 107: 15373-15378.
9. Kubik M F, Bell C, Fitzwater T, Watson S R, Tasset D M (1997) Isolation and characterization of 2'-fluoro-, 2'-amino-, and 2'-fluoro-/amino-modified RNA ligands to human IFN-gamma that inhibit receptor binding. J Immunol 159: 259-267.
10. Jellinek D, Lynott C K, Rifkin D B, Janjic N (1993) High-affinity RNA ligands to basic fibroblast growth factor inhibit receptor binding. Proc Natl Acad Sci USA 90: 11227-11231.

11. Binkley J, Allen P, Brown D M, Green L, Tuerk C, et al. (1995) RNA ligands to human nerve growth factor. Nucleic Acids Res 23: 3198-3205.
12. Green L S, Jellinek D, Jenison R, Ostman A, Heldin C H, et al. (1996) Inhibitory DNA ligands to platelet-derived growth factor B-chain. Biochemistry 35: 14413-14424.
13. Ruckman J, Green L S, Beeson J, Waugh S, Gillette W L, et al. (1998) 2'-Fluoropyrimidine RNA-based Aptamers to the 165-Amino Acid Form of Vascular Endothelial Growth Factor (VEGF165). Journal of Biological Chemistry 273: 20556-20567.
14. Fukuda K, Vishnuvardhan D, Sekiya S, Hwang J, Kakiuchi N, et al. (2000) Isolation and characterization of RNA aptamers specific for the hepatitis C virus nonstructural protein 3 protease. Eur J Biochem 267: 3685-3694.
15. Charlton J, Kirschenheuter G P, Smith D (1997) Highly potent irreversible inhibitors of neutrophil elastase generated by selection from a randomized DNA-valine phosphonate library. Biochemistry 36: 3018-3026.
16. Bock L C, Griffin L C, Latham J A, Vermaas E H, Toole J J (1992) Selection of single-stranded DNA molecules that bind and inhibit human thrombin. Nature 355: 564-566.
17. Rusconi C P, Scardino E, Layzer J, Pitoc G A, Ortel T L, et al. (2002) RNA aptamers as reversible antagonists of coagulation factor IXa. Nature 419: 90-94.
18. Ahmad K M, Oh S S, Kim S, McClellen F M, Xiao Y, et al. (2011) Probing the limits of aptamer affinity with a microfluidic SELEX platform. PLoS ONE 6: e27051.
19. Lupoid S E, Hicke B J, Lin Y, Coffey D S (2002) Identification and Characterization of Nuclease-stabilized RNA Molecules That Bind Human Prostate Cancer Cells via the Prostate-specific Membrane Antigen. Cancer Research 62: 4029-4033.
20. Chen ChB (2003) Inhibition of heregulin signaling by an aptamer that preferentially binds to the oligomeric form of human epidermal growth factor receptor-3. Proceedings of the National Academy of Sciences 100: 9226-9231.
21. Cerchia L, Ducongé F, Pestourie C, Boulay J, Aissouni Y, et al. (2005) Neutralizing aptamers from whole-cell SELEX inhibit the RET receptor tyrosine kinase. PLoS Biol 3: e123.
22. Liu Y, Sun Q A, Chen Q, Lee T H, Huang Y, et al. (2009) Targeting inhibition of GluR1 Ser845 phosphorylation with an RNA aptamer that blocks AMPA receptor trafficking. J Neurochem 108: 147-157.
23. Kraus E, James W, Barclay A N (1998) Cutting edge: novel RNA ligands able to bind CD4 antigen and inhibit CD4+ T lymphocyte function. J Immunol 160: 5209-5212.
24. Thiel K W, Hernandez L I, Dassie J P, Thiel W H, Liu X, et al. (2012) Delivery of chemo-sensitizing siRNAs to HER2+-breast cancer cells using RNA aptamers. Nucl Acids Res. 40(13):6319-37.
25. Theis M G, Knorre A, Kellersch B, Moelleken J, Wieland F, et al. (2004) Discriminatory aptamer reveals serum response element transcription regulated by cytohesin-2. Proc Natl Acad Sci USA 101: 11221-11226.
26. Mayer G, Blind M, Nagel W, Bohm T, Knorr T, et al. (2001) Controlling small guanine-nucleotide-exchange factor function through cytoplasmic RNA intramers. Proc Natl Acad Sci USA 98: 4961-4965.
27. Mi J, Zhang X, Giangrande P H, McNamara J O, 2nd, Nimjee S M, et al. (2005) Targeted inhibition of alphavbeta3 integrin with an RNA aptamer impairs endothelial cell growth and survival. Biochem Biophys Res Commun 338: 956-963.
28. Hicke B J, Marion C, Chang Y F, Gould T, Lynott C K, et al. (2001) Tenascin-C aptamers are generated using tumor cells and purified protein. J Biol Chem 276: 48644-48654.
29. Khati M, Schuman M, Ibrahim J, Sattentau Q, Gordon S, et al. (2003) Neutralization of infectivity of diverse R5 clinical isolates of human immunodeficiency virus type 1 by gp120-binding 2'F-RNA aptamers. J Virol 77: 12692-12698.
30. Giver L, Bartel D P, Zapp M L, Green M R, Ellington A D (1993) Selection and design of high-affinity RNA ligands for HIV-1 Rev. Gene 137: 19-24.
31. Allen P, Worland S, Gold L (1995) Isolation of high-affinity RNA ligands to HIV-1 integrase from a random pool. Virology 209: 327-336.
32. Blank M, Weinschenk T, Priemer M, Schluesener H (2001) Systematic evolution of a DNA aptamer binding to rat brain tumor microvessels. selective targeting of endothelial regulatory protein pigpen. J Biol Chem 276: 16464-16468.
33. Daniels D A, Chen H, Hicke B J, Swiderek K M, Gold L (2003) A tenascin-C aptamer identified by tumor cell SELEX: systematic evolution of ligands by exponential enrichment. Proc Natl Acad Sci USA 100: 15416-15421.
34. Shamah S M, Healy J M, Cload S T (2008) Complex Target SELEX. Accounts of Chemical Research 41: 130-138.
35. Sefah K, Tang Z W, Shangguan D H, Chen H, Lopez-Colon D, et al. (2009) Molecular recognition of acute myeloid leukemia using aptamers. Leukemia 23: 235-244.
36. Shangguan D, Meng L, Cao Z C, Xiao Z, Fang X, et al. (2008) Identification of liver cancer-specific aptamers using whole live cells. Anal Chem 80: 721-728.
37. Guo K T, Ziemer G, Paul A, Wendel H P (2008) CELL-SELEX: Novel perspectives of aptamer-based therapeutics. Int J Mol Sci 9: 668-678.
38. Morris K N, Jensen K B, Julin C M, Weil M, Gold L (1998) High affinity ligands from in vitro selection: complex targets. Proc Natl Acad Sci USA 95: 2902-2907.
39. Cerchia L, de Franciscis V (2010) Targeting cancer cells with nucleic acid aptamers. Trends Biotechnol 28: 517-525.
40. Meyer C, Hahn U, Rentmeister A (2011) Cell-specific aptamers as emerging therapeutics. J Nucleic Acids 2011: 904750.
41. Wullner U, Neef I, Eller A, Kleines M, Tur M K, et al. (2008) Cell-specific induction of apoptosis by rationally designed bivalent aptamer-siRNA transcripts silencing eukaryotic elongation factor 2. Curr Cancer Drug Targets 8: 554-565.
42. Schutze T, Arndt P F, Menger M, Wochner A, Vingron M, et al. (2010) A calibrated diversity assay for nucleic acid libraries using DiStRO-a Diversity Standard of Random Oligonucleotides. Nucleic Acids Res 38: e23.
43. Hofacker I L, Fontana W, Stadler P F, Bonhoeffer L S, Tacker M, et al. (1994) Fast folding and comparison of RNA secondary structures. Monatshefte für Chemie/Chemical Monthly 125: 167-188.
44. Lorenz R, Bernhart S H, Honer Zu Siederdissen C, Tafer H, Flamm C, et al. (2011) ViennaRNA Package 2.0. Algorithms Mol Biol 6: 26.
45. Berezhnoy A, Stewart C A, McNamara Ii J O, Thiel W, Giangrande P, et al. (2012) Isolation and Optimization of Murine IL-10 Receptor Blocking Oligonucleotide Aptamers Using High-throughput Sequencing. Mol Ther.

46. Schutze T, Wilhelm B, Greiner N, Braun H, Peter F, et al. (2011) Probing the SELEX Process with Next-Generation Sequencing. PLoS ONE 6: e29604.
47. Zimmermann B, Gesell T, Chen D, Lorenz C, Schroeder Re (2010) Monitoring Genomic Sequences during SELEX Using High-Throughput Sequencing: Neutral SELEX. PLoS ONE 5: e9169.
48. Thiel W H, Bair T, Wyatt Thiel K, Dassie J P, Rockey W M, et al. (2011) Nucleotide bias observed with a short SELEX RNA aptamer library. Nucleic Acid Ther 21: 253-263.
49. Layzer J M, Sullenger B A (2007) Simultaneous generation of aptamers to multiple gamma-carboxyglutamic acid proteins from a focused aptamer library using DeSELEX and convergent selection. Oligonucleotides 17: 1-11.
50. Cerchia L, Esposito C L, Jacobs A H, Tavitian B, de Franciscis V (2009) Differential SELEX in human glioma cell lines. PLoS ONE 4: e7971.
51. Homann M, Goringer H U (1999) Combinatorial selection of high affinity RNA ligands to live African trypanosomes. Nucleic Acids Res 27: 2006-2014.
52. Chen F, Zhou J, Luo F, Mohammed A B, Zhang X L (2007) Aptamer from whole-bacterium SELEX as new therapeutic reagent against virulent *Mycobacterium tuberculosis*. Biochem Biophys Res Commun 357: 743-748.
53. Mi J, Liu Y, Rabbani Z N, Yang Z, Urban J H, et al. (2010) In vivo selection of tumor-targeting RNA motifs. Nat Chem Biol 6: 22-24.
54. Mallikaratchy P, Stahelin R V, Cao Z, Cho W, Tan W (2006) Selection of DNA ligands for protein kinase C-delta. Chem Commun (Camb): 3229-3231.
55. Li L, Li B, Qi Y, Jin Y (2009) Label-free aptamer-based colorimetric detection of mercury ions in aqueous media using unmodified gold nanoparticles as colorimetric probe. Anal Bioanal Chem 393: 2051-2057.
56. Mi Z, Guo H, Russell M B, Liu Y, Sullenger B A, et al. (2009) RNA aptamer blockade of osteopontin inhibits growth and metastasis of MDA-MB231 breast cancer cells. Mol Ther 17: 153-161.
57. Hernandez F J, Stockdale K R, Huang L, Horswill A R, Behlke M A, et al. (2012) Degradation of nuclease-stabilized RNA oligonucleotides in Mycoplasma-contaminated cell culture media. Nucleic Acid Ther 22: 58-68.
58. Huang Y, Eckstein F, Padilla R, Sousa R (1997) Mechanism of ribose 2'-group discrimination by an RNA polymerase. Biochemistry 36: 8231-8242.
59. Sousa R, Padilla R (1995) A mutant T7 RNA polymerase as a DNA polymerase. EMBO J 14: 4609-4621.
60. Rockey W M, Hernandez F J, Huang S Y, Cao S, Howell C A, et al. (2011) Rational truncation of an RNA aptamer to prostate-specific membrane antigen using computational structural modeling. Nucleic Acid Ther 21: 299-314.
61. McNamara J O, Kolonias D, Pastor F, Mittler R S, Chen L, et al. (2008) Multivalent 4-1BB binding aptamers costimulate CD8+ T cells and inhibit tumor growth in mice. Journal of Clinical Investigation 118: 376-386.
62. Zuker M, Stiegler P (1981) Optimal computer folding of large RNA sequences using thermodynamics and auxiliary information. Nucleic Acids Res 9: 133-148.
63. McCaskill J S (1990) The equilibrium partition function and base pair binding probabilities for RNA secondary structure. Biopolymers 29: 1105-1119.
64. Bompfunewerer A F, Backofen R, Bernhart S H, Hertel J, Hofacker I L, et al. (2008) Variations on RNA folding and alignment: lessons from Benasque. J Math Biol 56: 129-144.
65. Lundberg P, El-Andaloussi S, Sutlu T, Johansson H, Langel U (2007) Delivery of short interfering RNA using endosomolytic cell-penetrating peptides. FASEB J 21: 2664-2671.
66. McNamara J O, Andrechek E R, Wang Y, Viles K D, Rempel R E, et al. (2006) Cell type-specific delivery of siRNAs with aptamer-siRNA chimeras. Nature Biotechnology 24: 1005-1015.

Example 2

Figures 12, 13, 14, 15, 16, 16A:
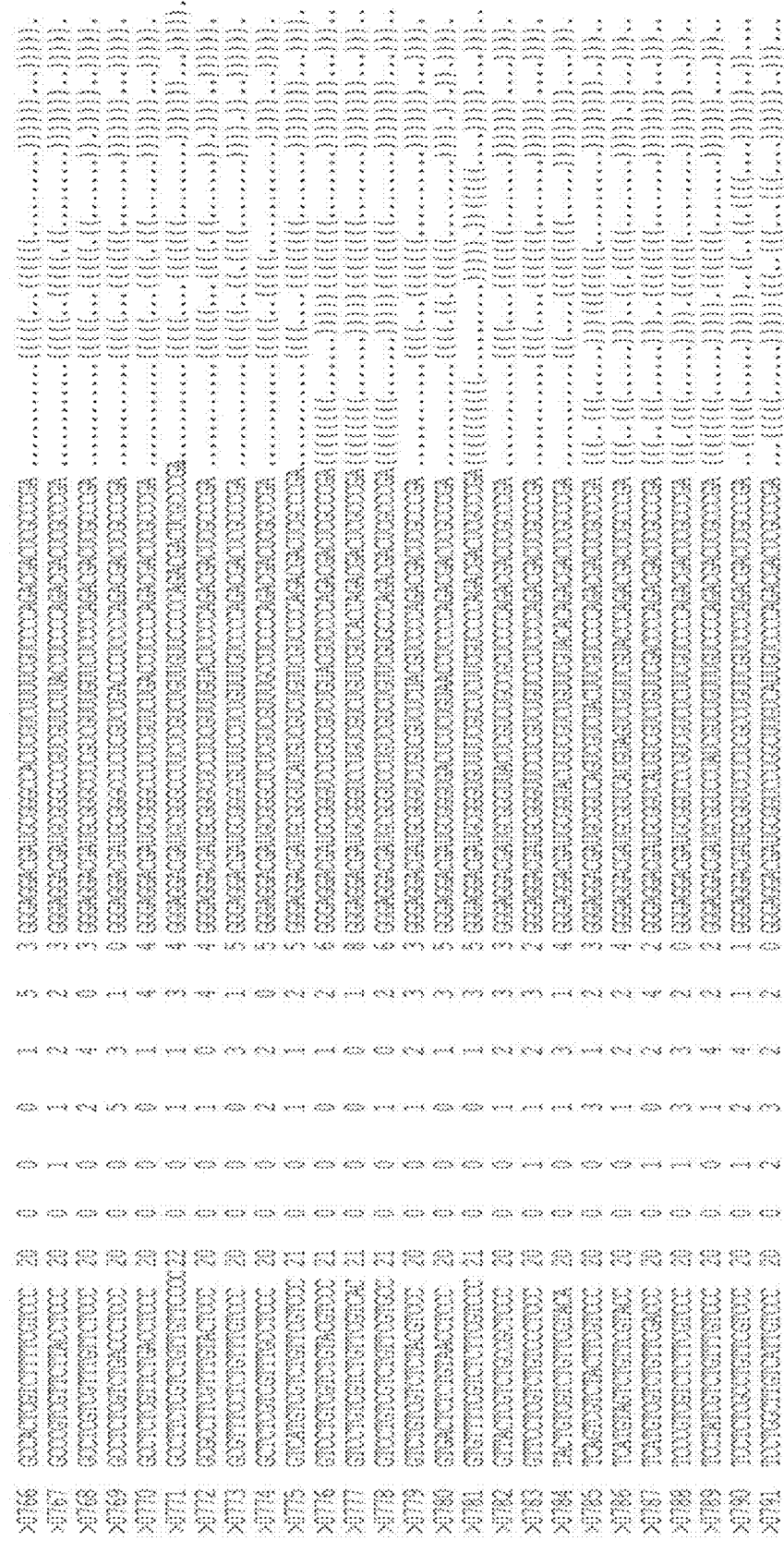
Figures 12, 13, 14, 15, 16, 16B:
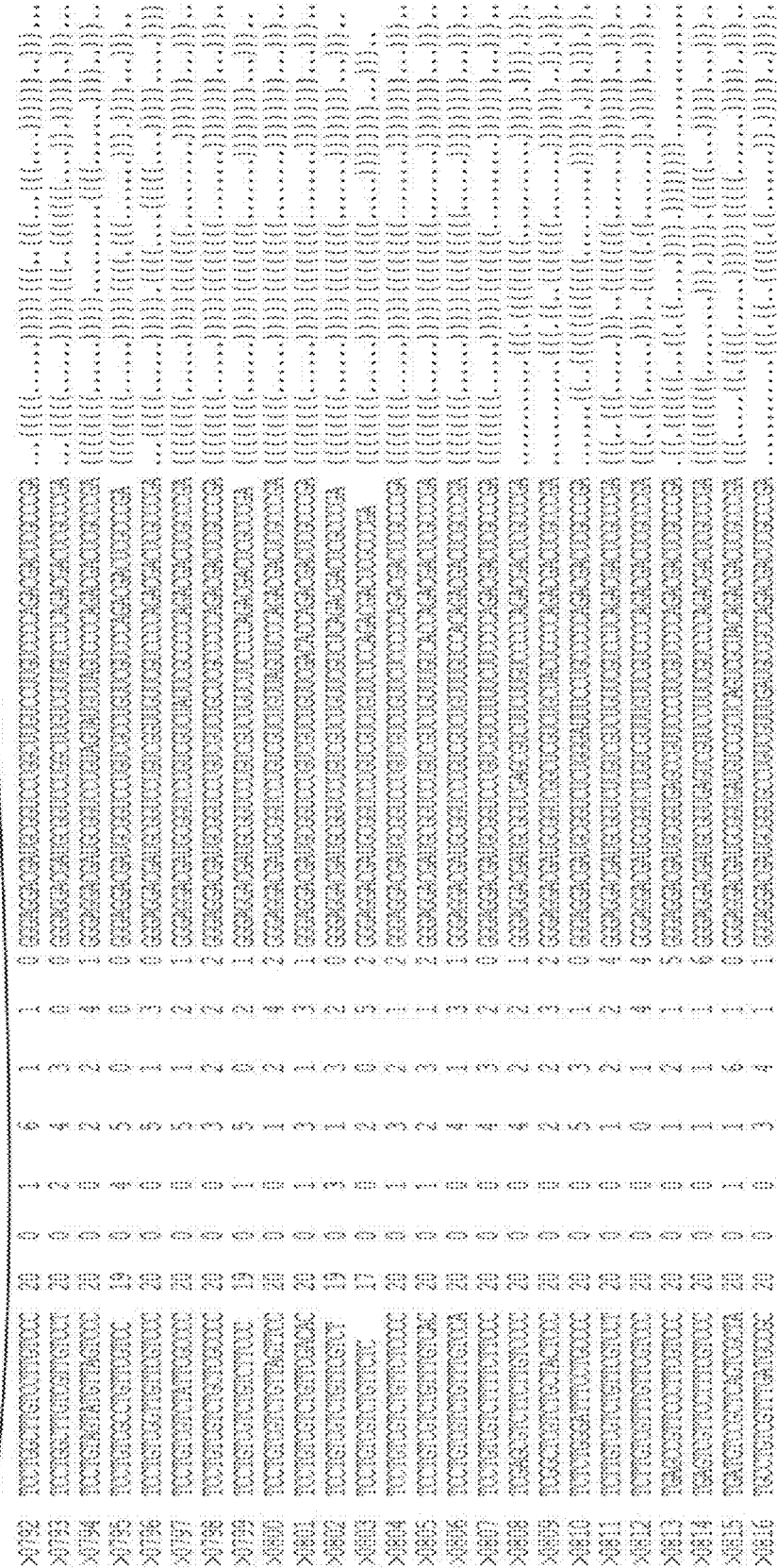
Figures 12, 13, 14, 15, 16, 17, 17B:
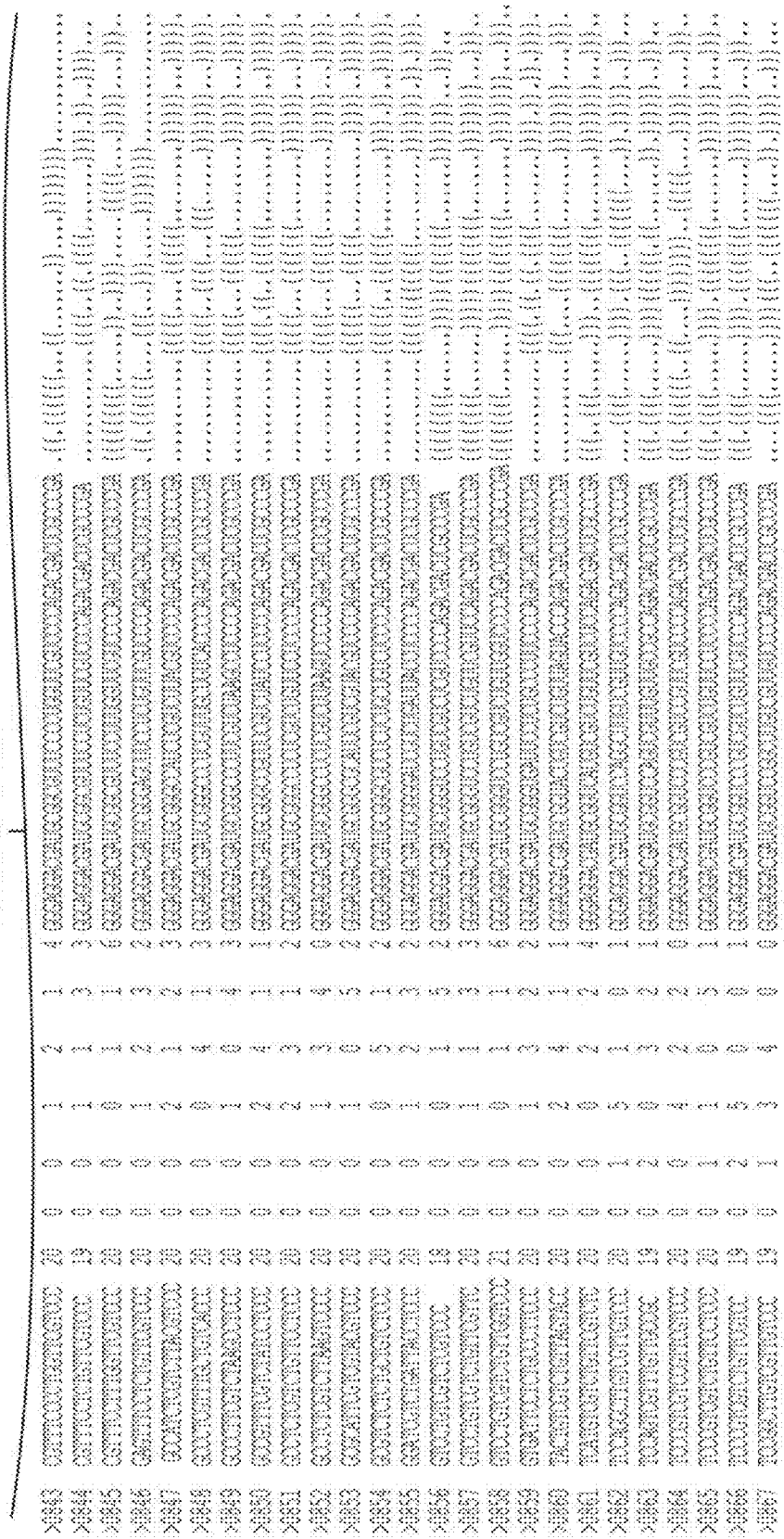
Figures 12, 13, 14, 15, 16, 17, 18, 18B:
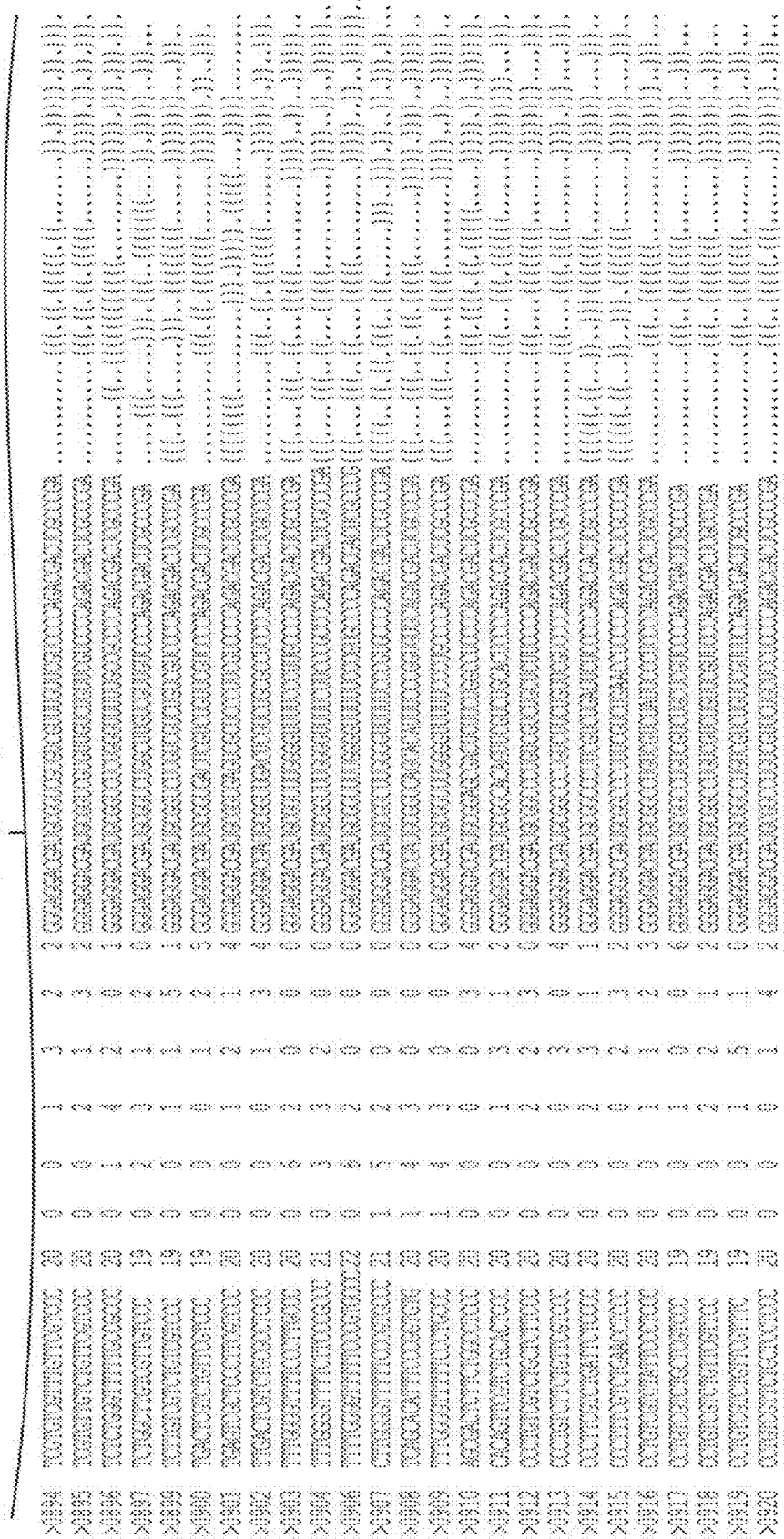
Figure 16A:
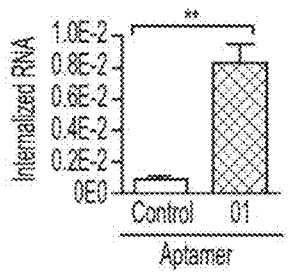
Figure 16B:
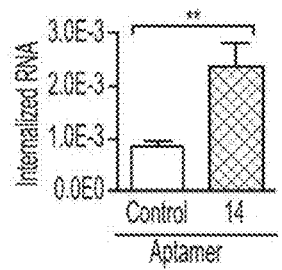
Figure 16C:
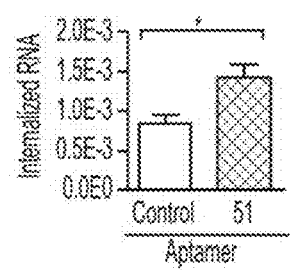
Figure 17A:
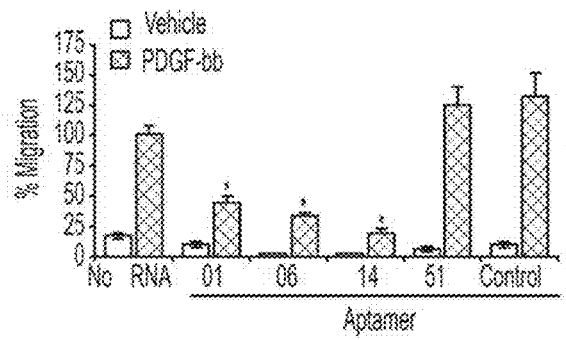
FIGS. 17A-17B: Aptamer antagonism of PDGF-BB dependent VSMC migration but not EC migration. PDGF-BB (10 ng/mL) dependent migration was measured for A) VSMCs and B) ECs by transwell migration assay in the presence of aptamers. ($*p<0.05$).
Figure 17B:
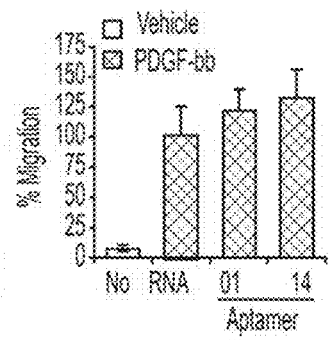
Figure 18A:
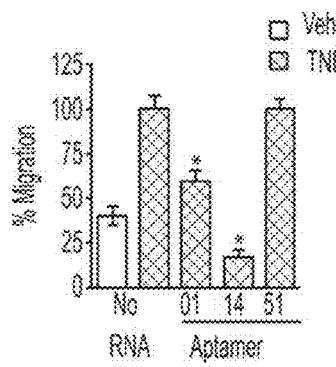
FIGS. 18A-18B: Aptamer antagonism of TNF-α and thrombin dependent VSMC migration. A) TNF-α and B) thrombin dependent VSMC migration was measured by transwell migration assay in the presence of aptamers. ($*p<0.05$)
Figure 18B:
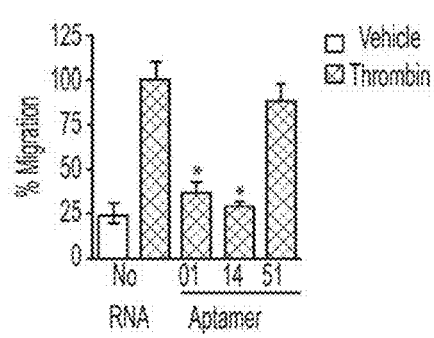
Figure 19:
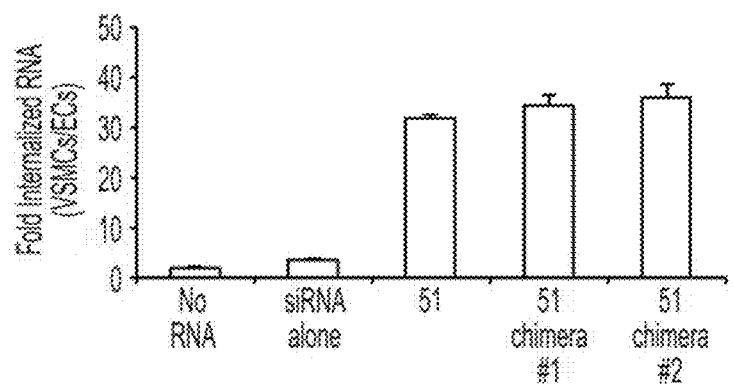
Figure 20:
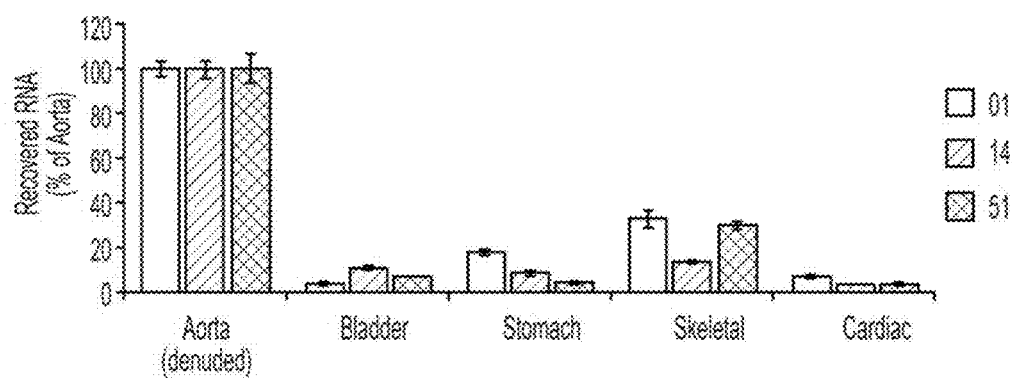

It has now been shown that the aptamers selected on VSMCs in culture bind to rat and human vessel segments ex-vivo (FIGS. 14A-14B, 15A-15C and 17A-17B). Several of the aptamers (01, 14 and 51) bind to denuded vessels (exposed smc layer) ex vivo (FIGS. 16A-16C. Other figures show evaluating the functional effects of several of these aptamers on migration and proliferation of VSMCs (FIGS. 13A-13B, 18A-18B, 19). Effects of aptamer 14 and 01 were seen on inhibiting VSMC migration but not proliferation. These experiments were carried out in the present of two agonists (PDGF and TNFalpha) showing that the aptamers can inhibit multiple agonists and are probably affecting pathways downstream of the target receptor.

Figures 12, 13, 14, 15, 16, 17, 18, 19, 20, 20B:
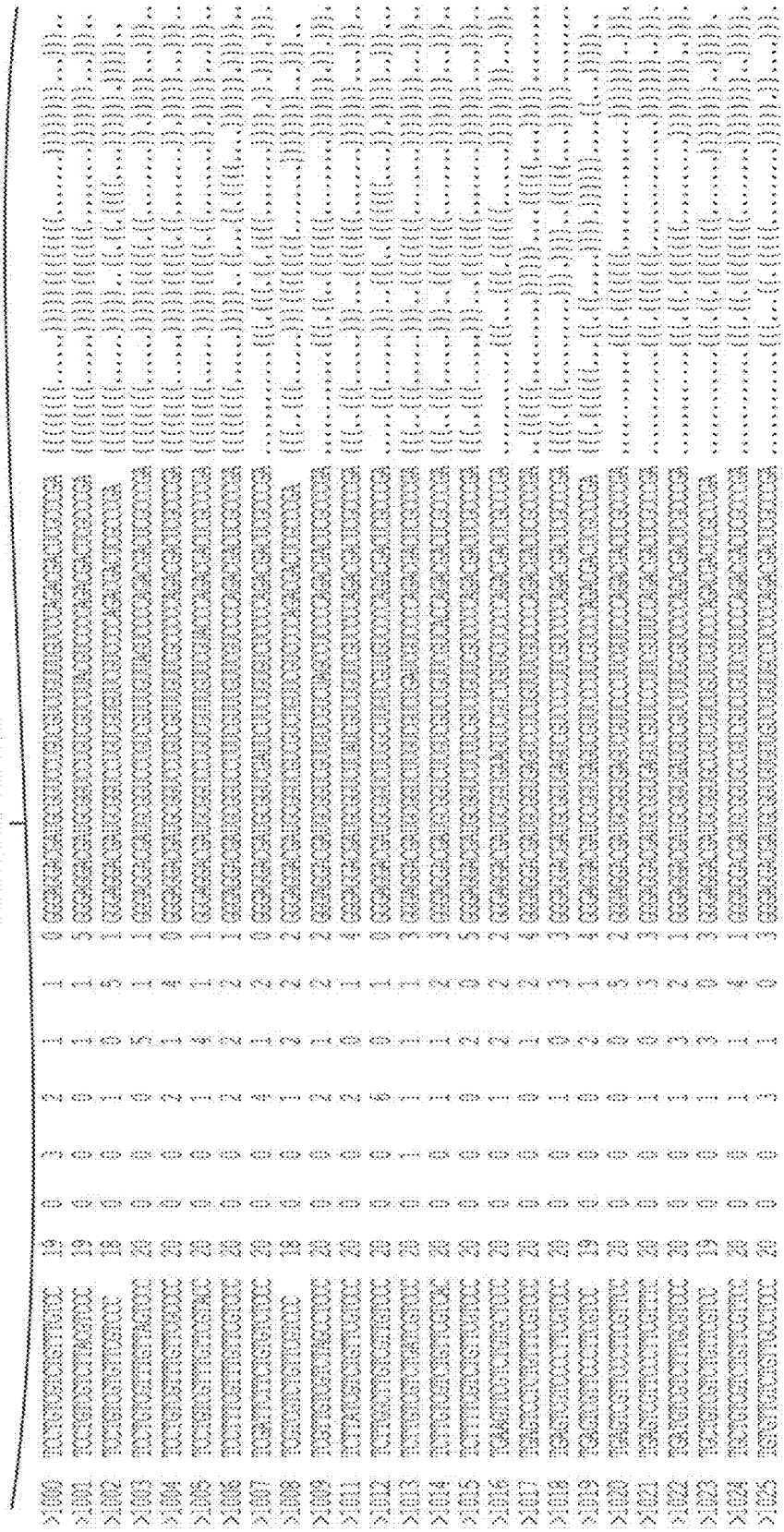
Figures 12, 13, 14, 15, 16, 17, 18, 19, 20, 21:
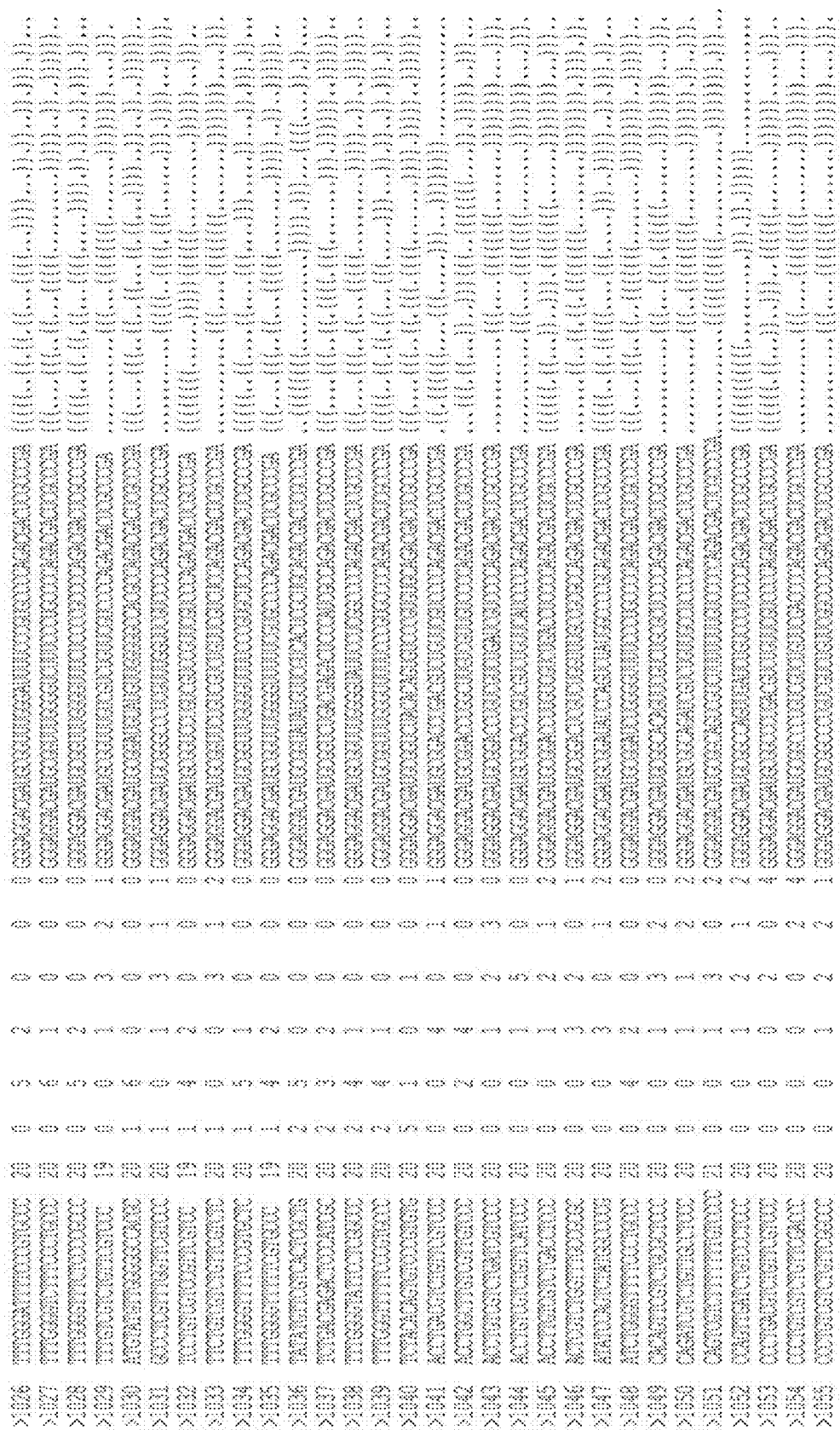
Figures 12, 13, 14, 15, 16, 17, 18, 19, 20, 21, 22, 23, 23B:
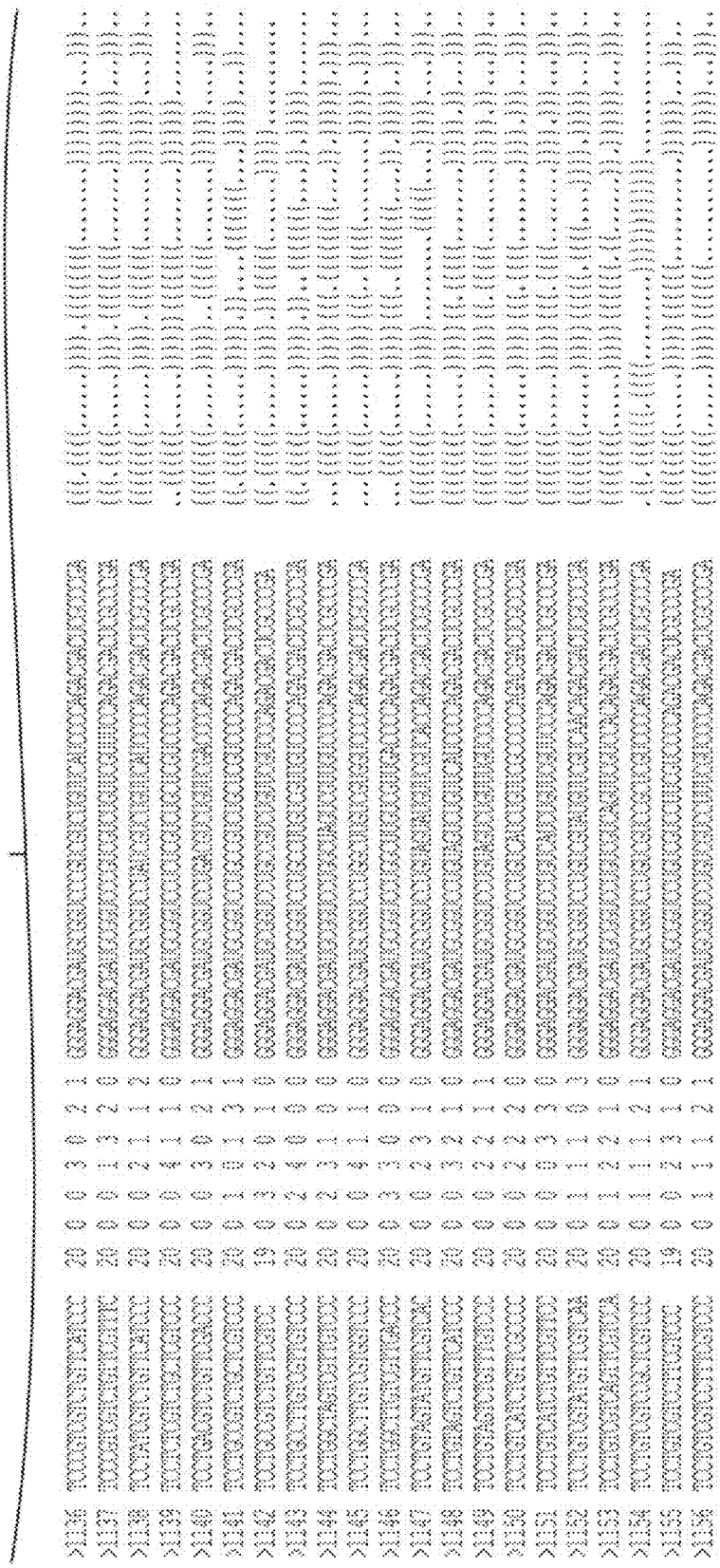
Figures 12, 13, 14, 15, 16, 17, 18, 19, 20, 21, 22, 23, 24, 24B:
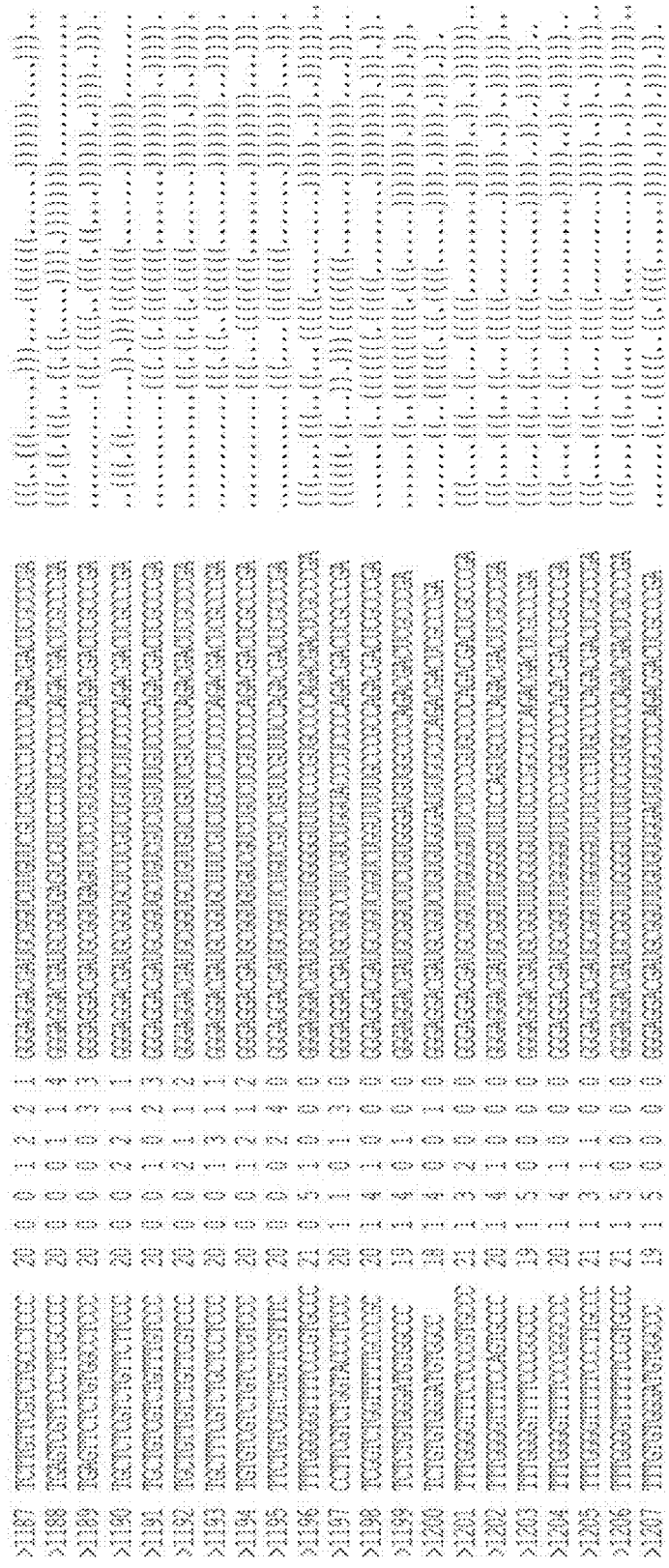
Figures 12, 13, 14, 15, 16, 17, 18, 19, 20, 21, 22, 23, 24, 25, 25B:
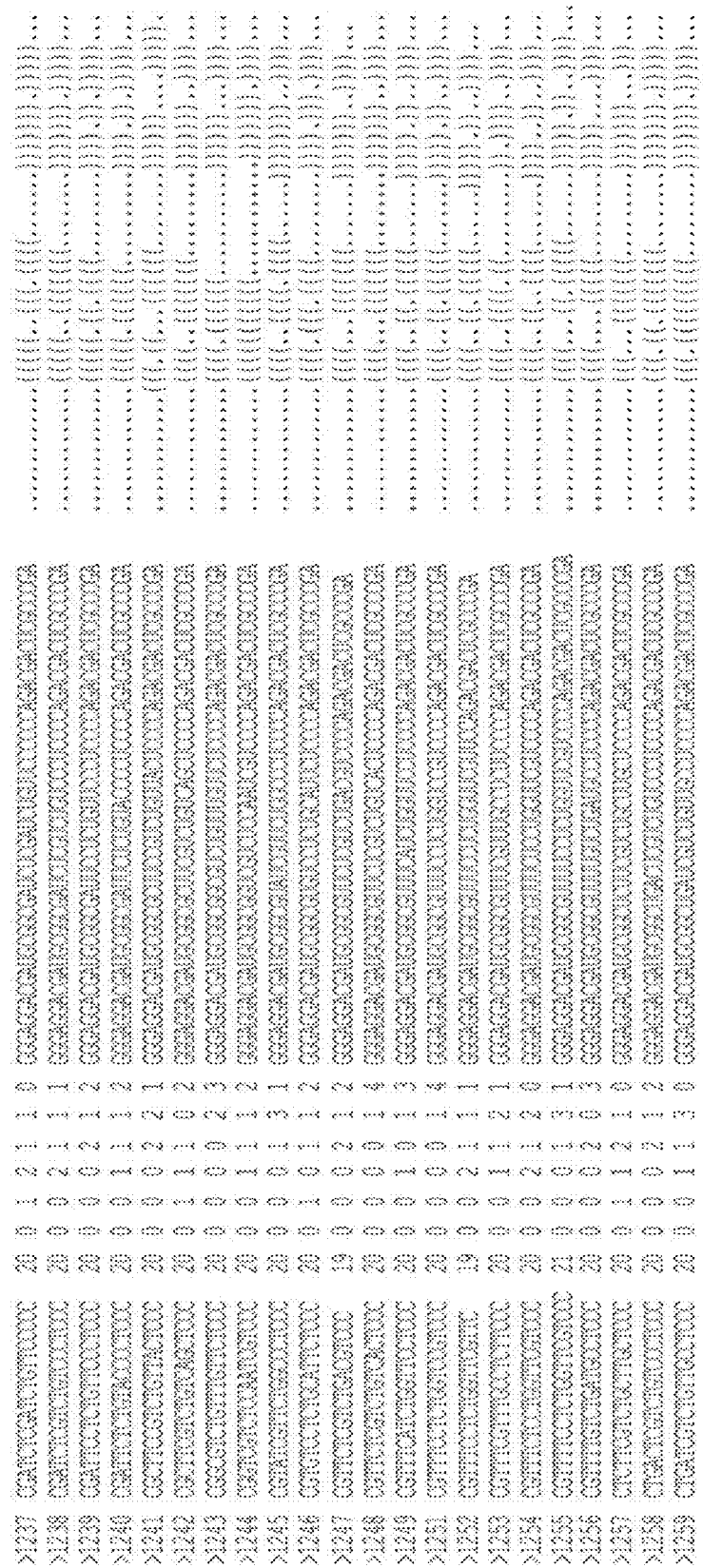
Figures 12, 13, 14, 15, 16, 17, 18, 19, 20, 21, 22, 23, 24, 25, 26, 26B:
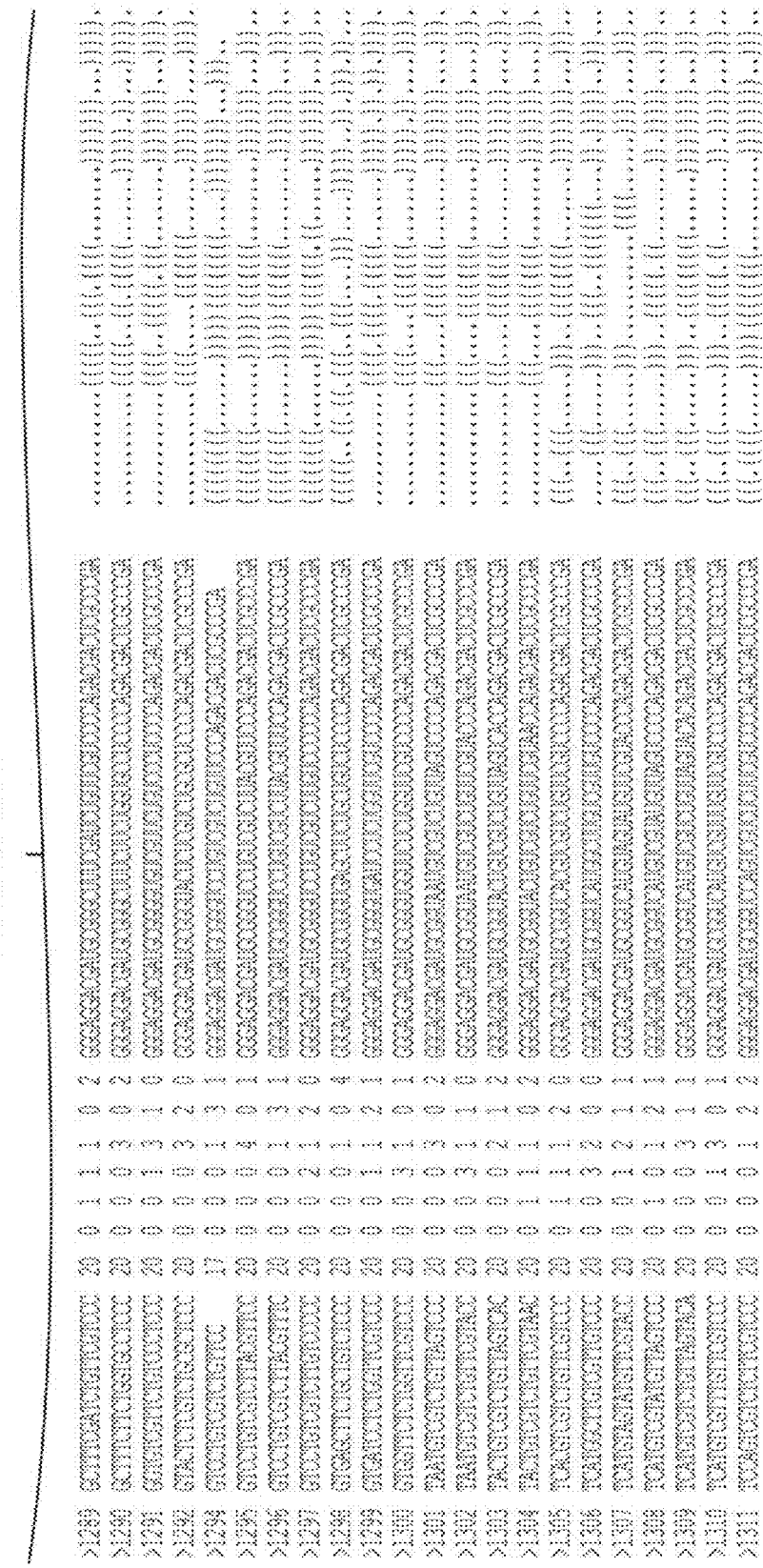
Figures 12, 13, 14, 15, 16, 17, 18, 19, 20, 21, 22, 23, 24, 25, 26, 27, 28, 28B:
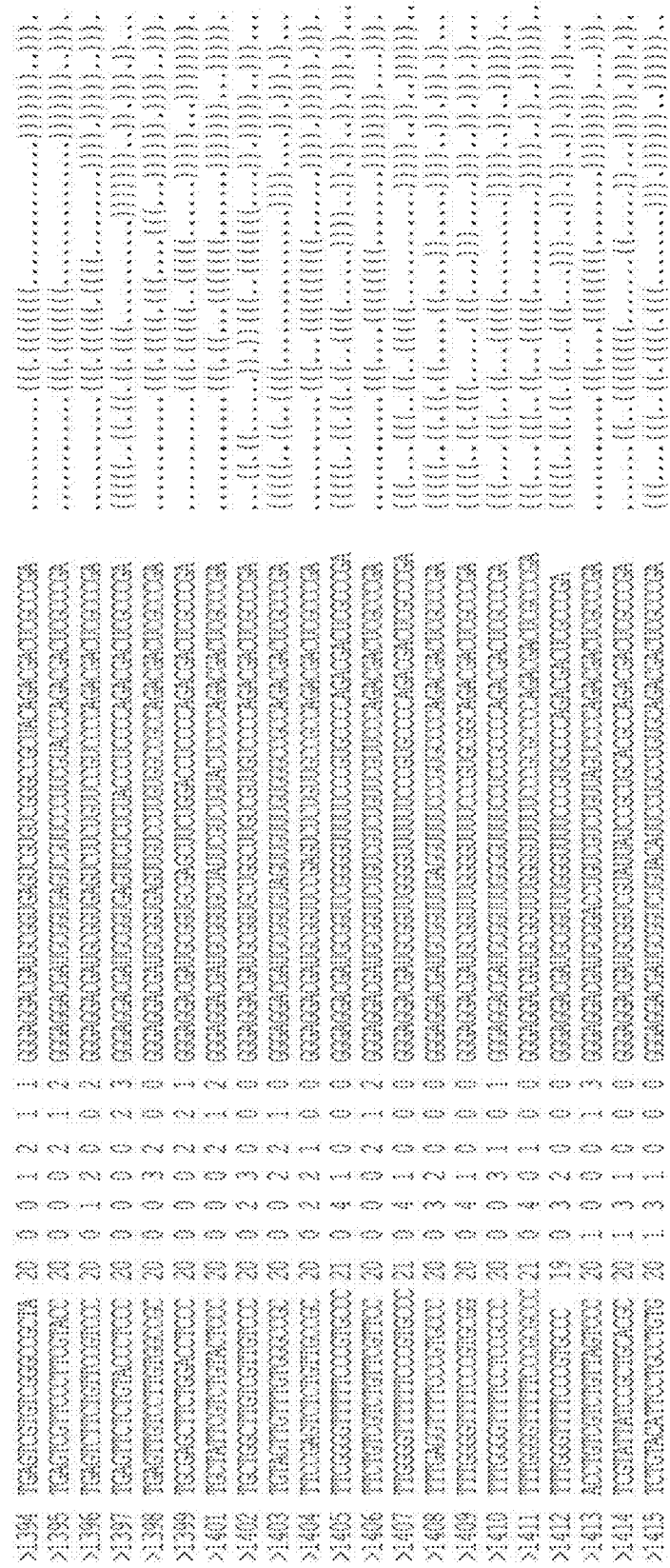
Figures 12, 13, 14, 15, 16, 17, 18, 19, 20, 21, 22, 23, 24, 25, 26, 27, 28, 29, 29B:
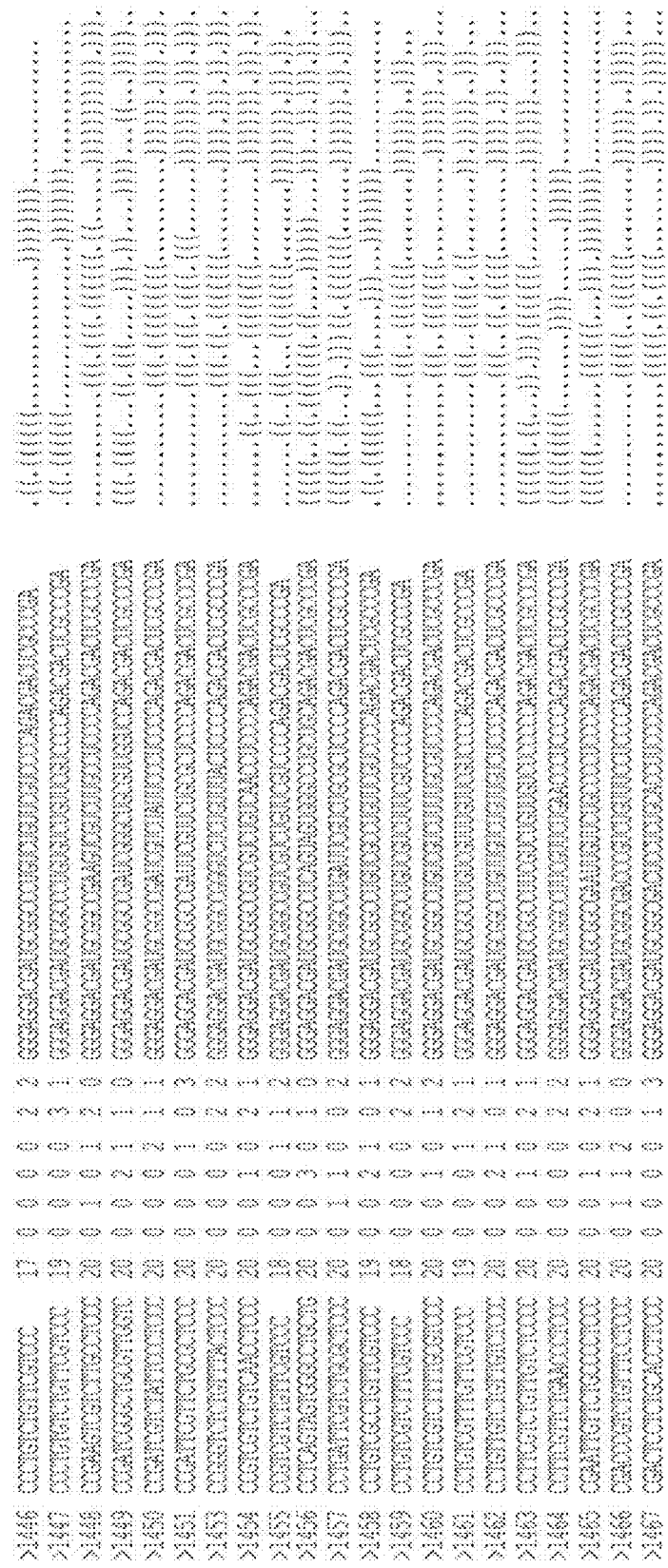
Figures 12, 13, 14, 15, 16, 17, 18, 19, 20, 21, 22, 23, 24, 25, 26, 27, 28, 29, 30, 31, 31B:
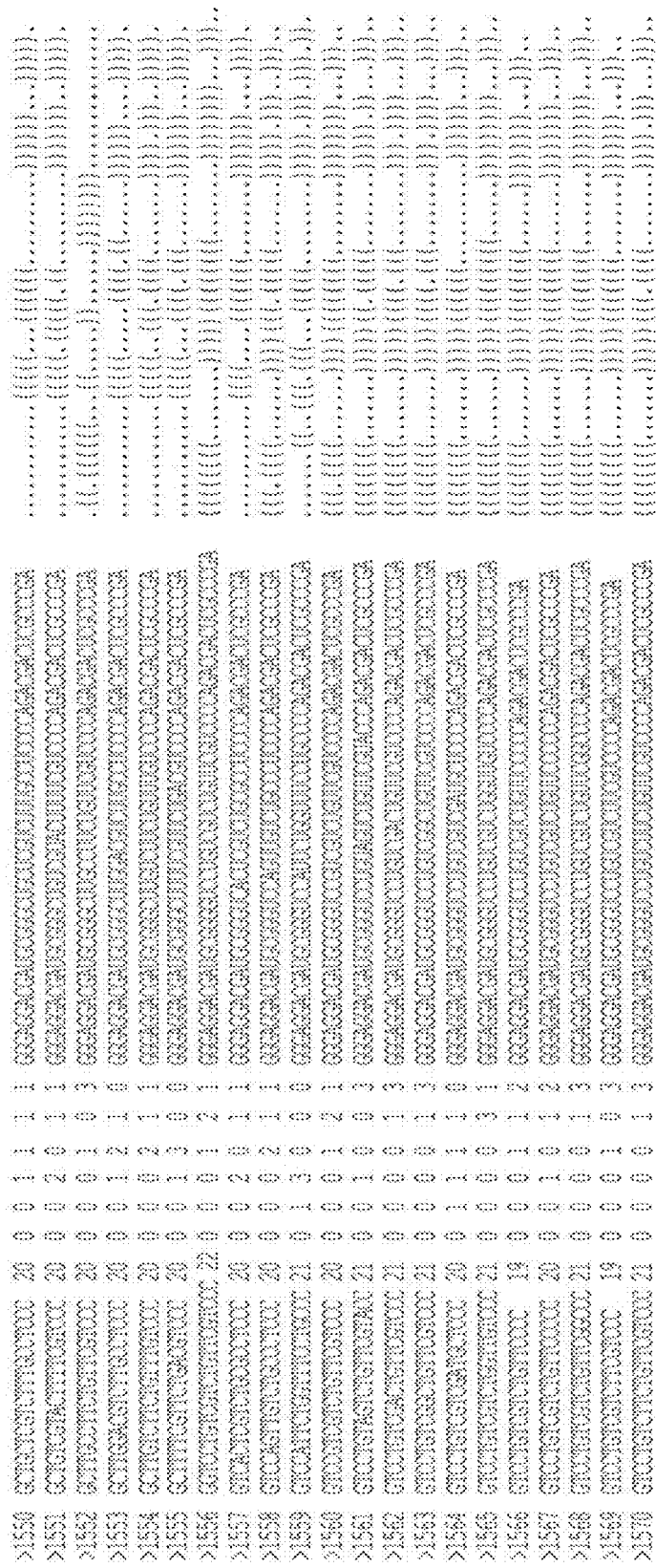
Figures 12, 13, 14, 15, 16, 17, 18, 19, 20, 21, 22, 23, 24, 25, 26, 27, 28, 29, 30, 31, 32, 32B:
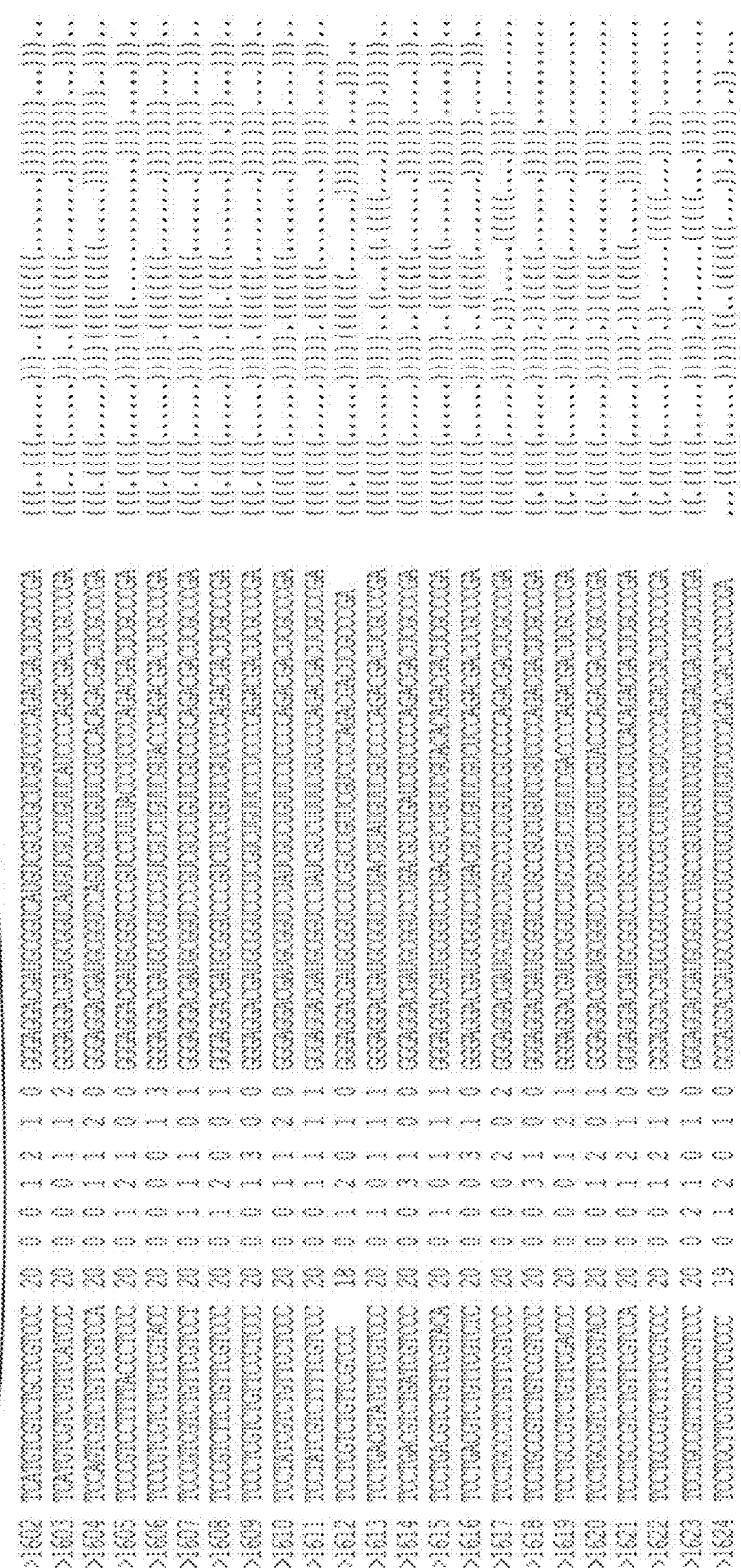
Figures 12, 13, 14, 15, 16, 17, 18, 19, 20, 21, 22, 23, 24, 25, 26, 27, 28, 29, 30, 31, 32, 33, 33A:
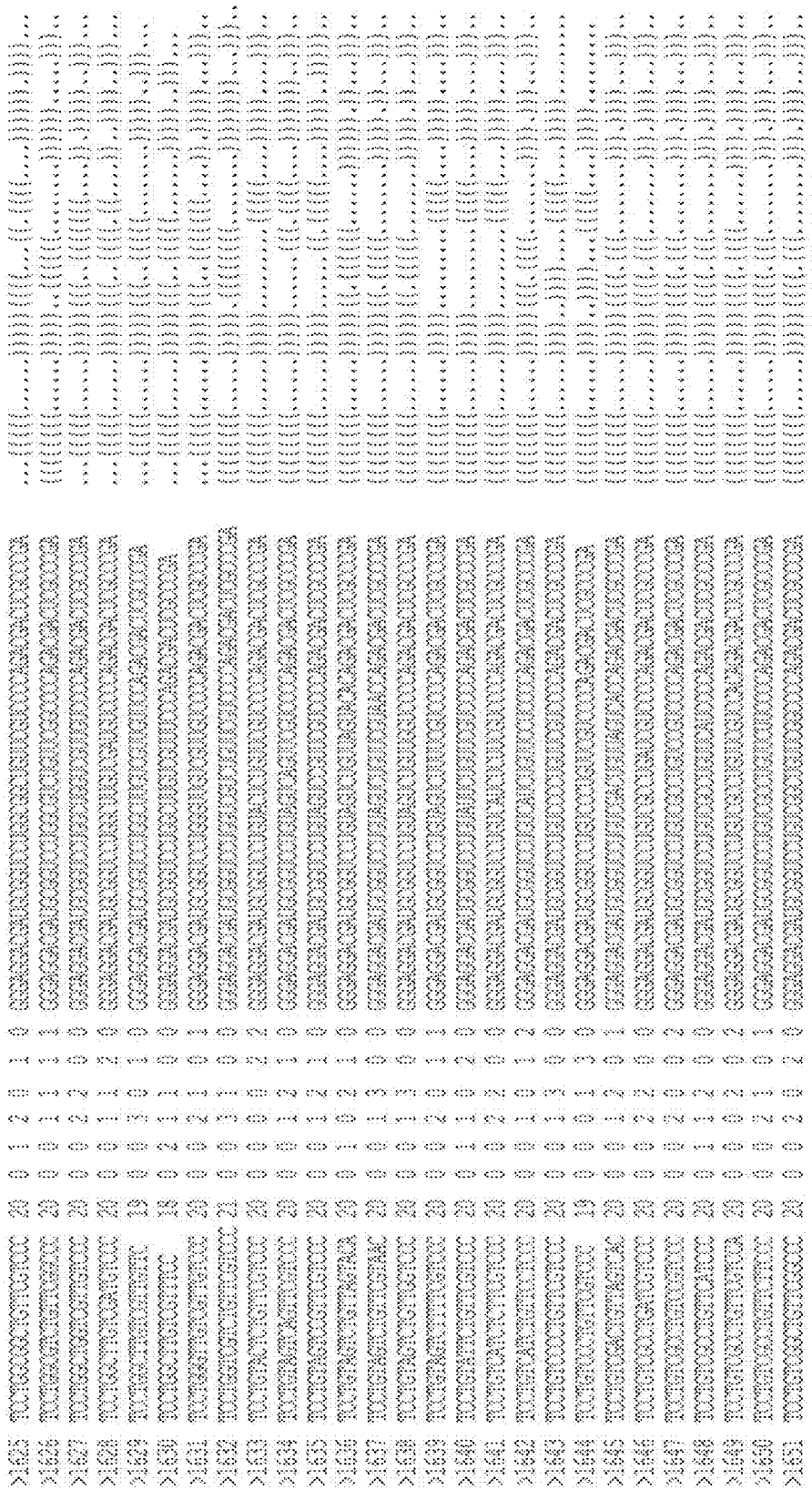
Figures 12, 13, 14, 15, 16, 17, 18, 19, 20, 21, 22, 23, 24, 25, 26, 27, 28, 29, 30, 31, 32, 33, 34, 35, 36, 37, 38, 38B:
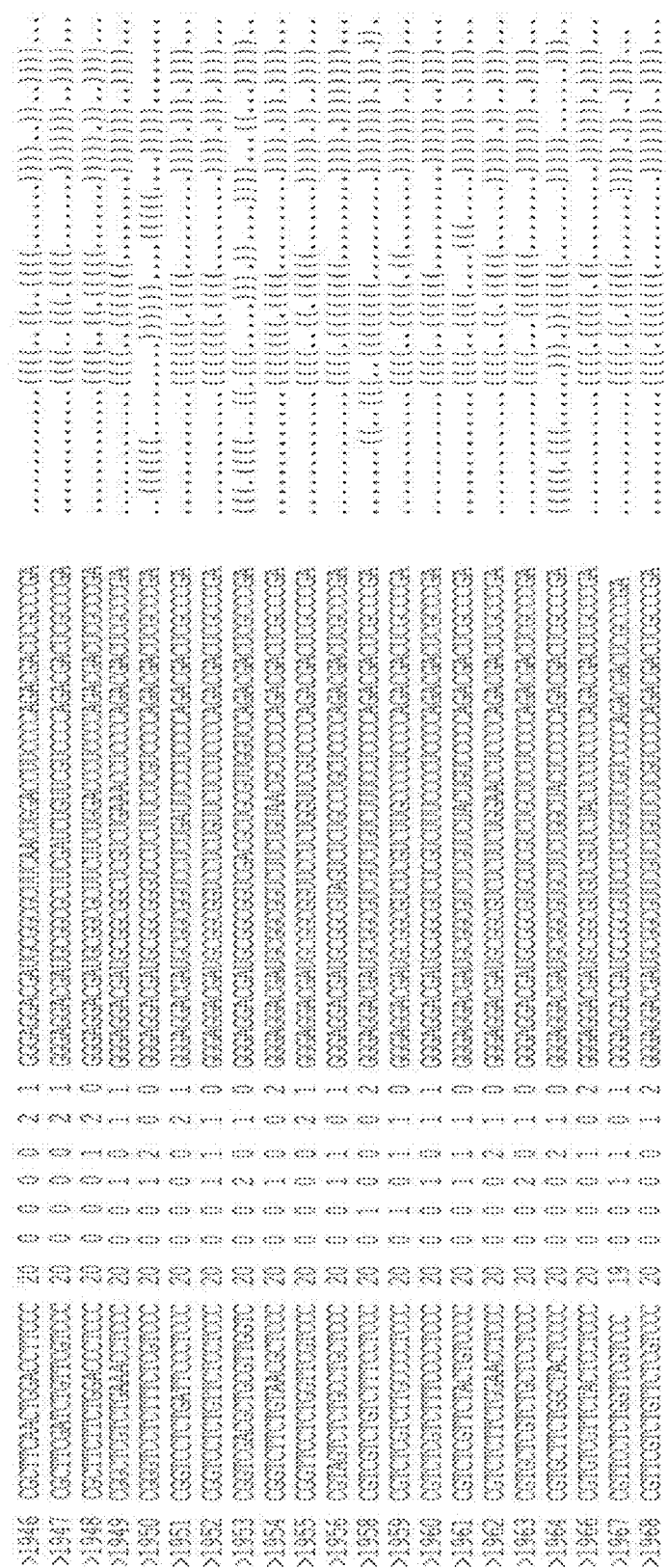
Figures 12, 13, 14, 15, 16, 17, 18, 19, 20, 21, 22, 23, 24, 25, 26, 27, 28, 29, 30, 31, 32, 33, 34, 35, 36, 37, 38, 39, 39B:
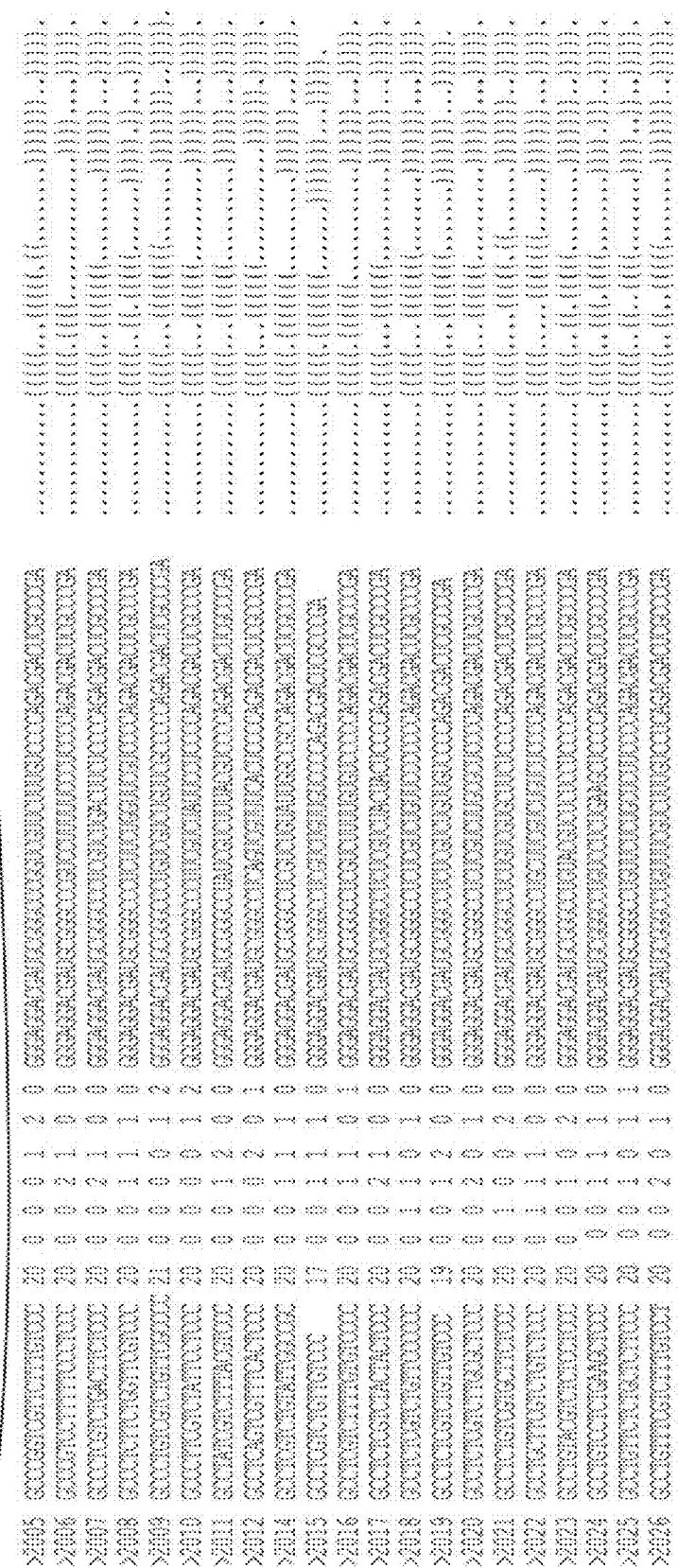
Figures 12, 13, 14, 15, 16, 17, 18, 19, 20, 21, 22, 23, 24, 25, 26, 27, 28, 29, 30, 31, 32, 33, 34, 35, 36, 37, 38, 39, 40, 40B:
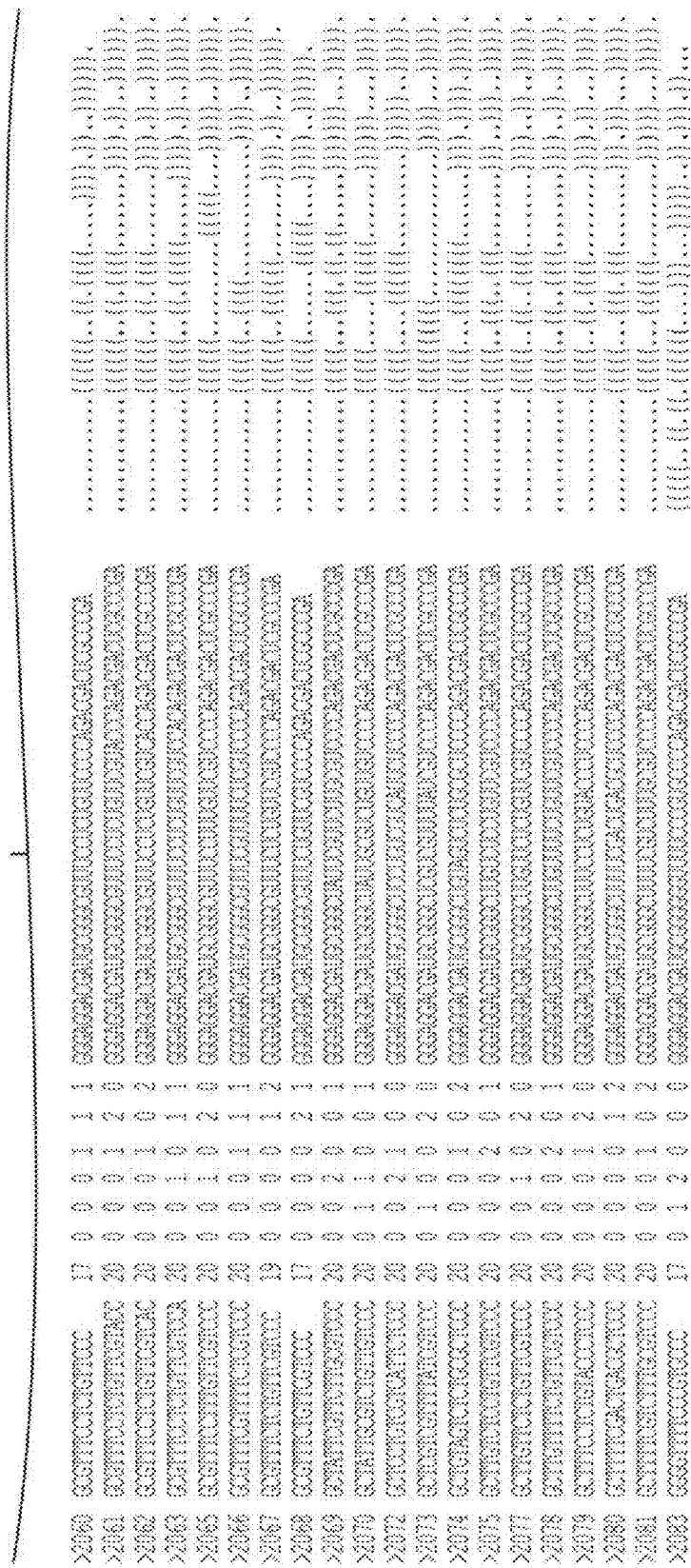
Figures 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 46B:
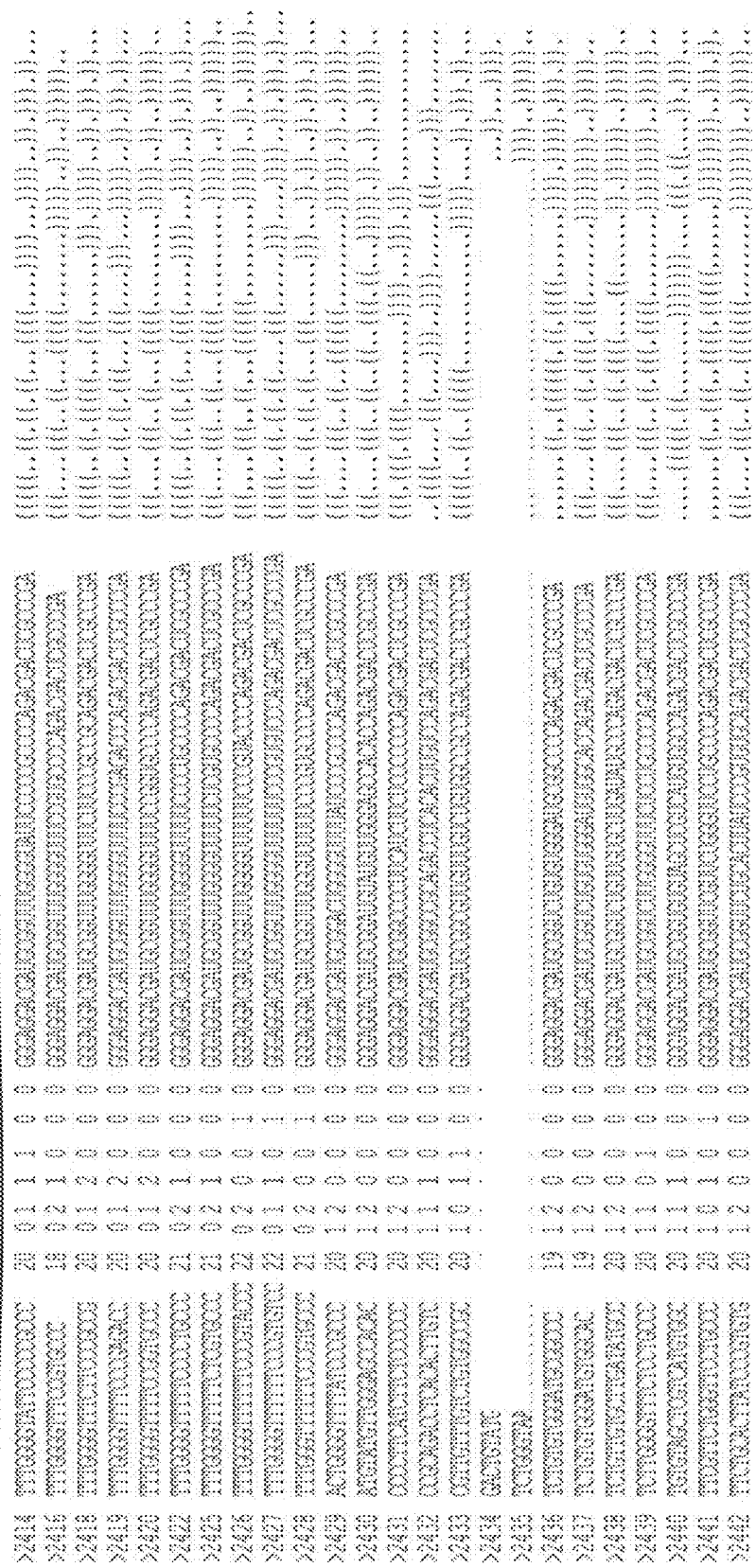
Figures 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
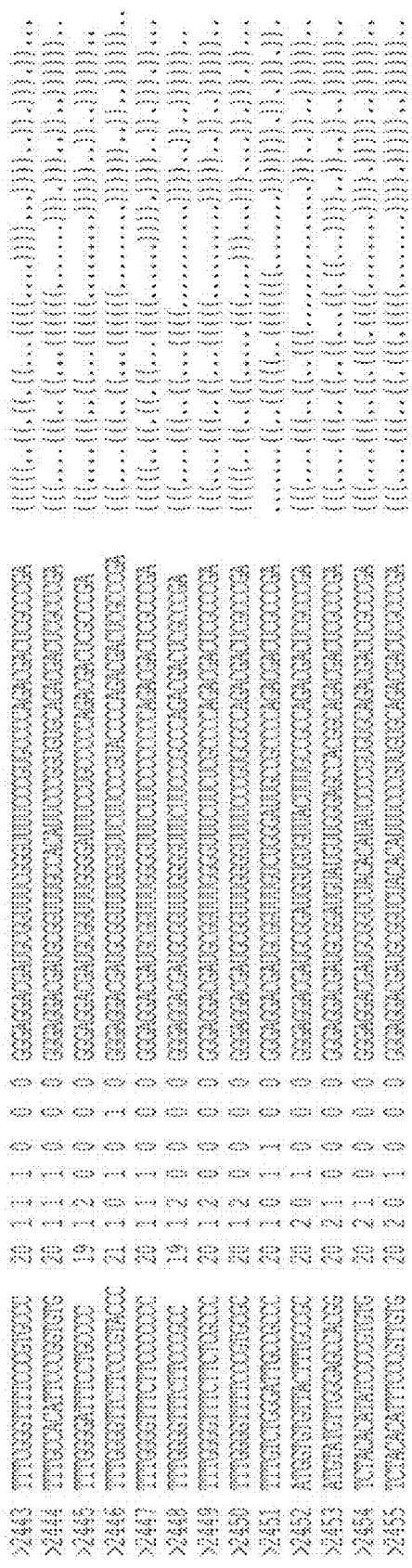
Figure 15B:
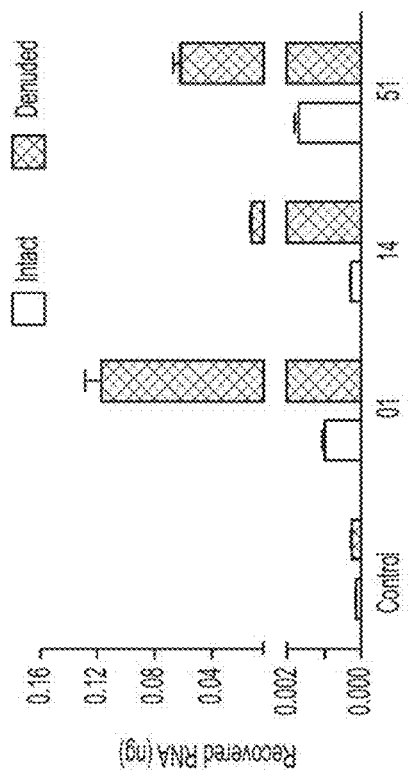
FIGS. 15A-15C: Internalization of VSMC aptamers in an in vivo model of arterial injury. A) Schematic of in vivo aptamer internalization assay. The illiac and femoral arteries were clamped and epigastric ligated. The deep femoral was cannulated to allow access to the illiac and femoral arteries for endothelium denuding by balloon angioplasty and subsequent exposure of aptamers. Denuded endothelium or intact arteries were perfused with 150 nM non-internalizing control aptamer or VSMC-specific aptamers (01, 14, and 51) for 30 min. Following stringent washes to remove surface-bound aptamers, arteries were isolated and aptamers recovered and quantitated by RT-qPCR. B) Raw data of recovered internalized aptamers. Endothelium denuded and endothelium intact arteries were exposed to either a non-internalizing control aptamer (Control), aptamers 01, aptamer 14, or aptamer 51. Non-internalized aptamer was removed by high salt wash and internalized aptamer, recovered by TRIzol extraction and measured by RT-qPCR. ($*p<<0.05$) C) Internalization into endothelium denuded relative to intact vessels.
Figure 15C:
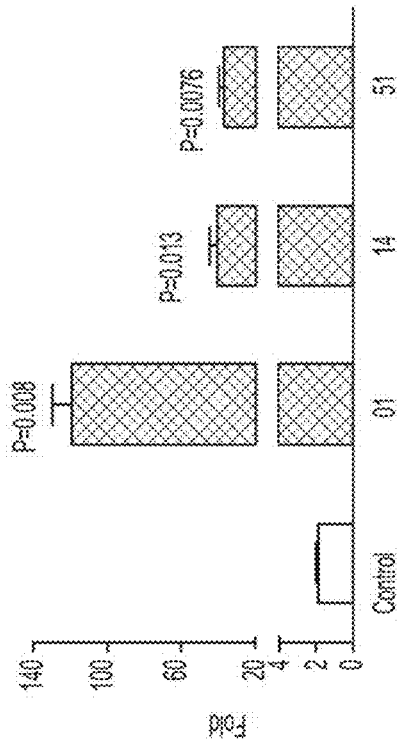
Figure 15A:
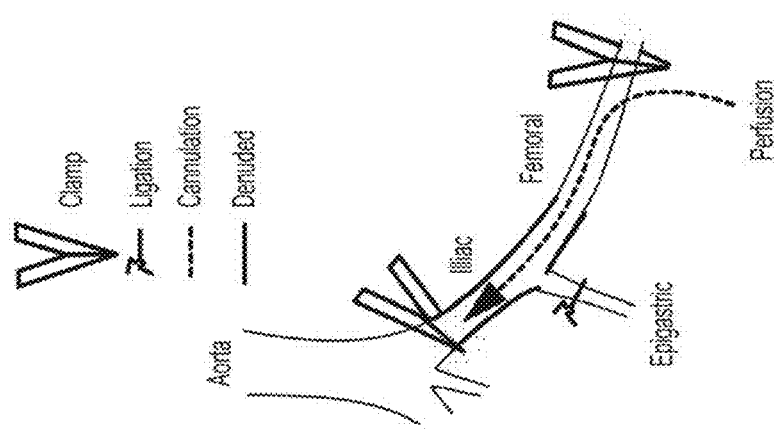

It was shown that aptamers are specific for vascular smooth muscle over muscle types (FIG. 20). Aptamers (150 nM) were incubated with tissue segments ex vivo for 30 min and recovered RNA measured by RT-qPCR. Data were normalized to tissue mass and expressed relative to denuded aorta.

Figure 21A:
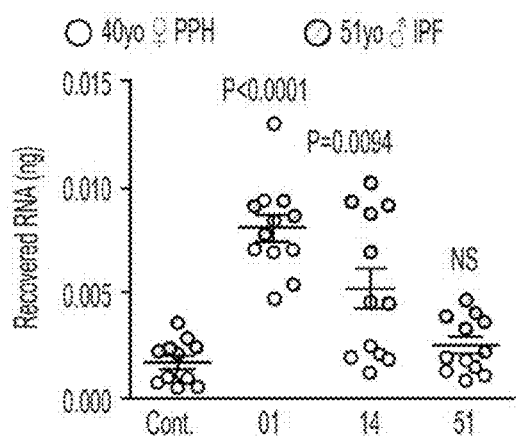
FIGS. 21A-21B: Cross-reactivity with human arterial segments and VSMCs. Amount of recovered RNA by RT-qPCR after incubation of aptamers (150 nM) for 30 min on A) segments of human pulmonary artery (PPH=primary pulmonary hypertension; IPF=Idiopathic pulmonary fibrosis); or B) $1.25 \times 10^5$ cultured primary human aortic VSMCs (ATCC #PCS-100-012).
Figure 21B:
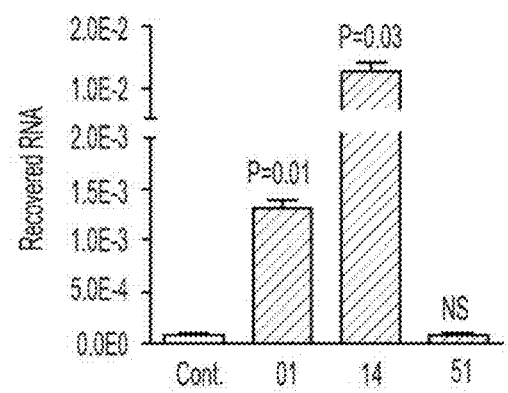

The cross-reactivity of aptamers with human arterial segments and VSMCs was studied (FIGS. 21A-21B). The amount of recovered RNA by RT-qPCR after incubation of aptamers (150 nM) for 30 min was measured on A) segments of human pulmonary artery (PPH=primary pulmonary hypertension; IPF=Idiopathic pulmonary fibrosis); or B) $1.25 \times 10^5$ cultured primary human aortic VSMCs (ATCC #PCS-100-012).

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10113172B2). An electronic copy of the "Sequence Listing" will also be available from the USPTO upon request and payment of the fee set forth in 37 CFR 1.19(b)(3).

What is claimed is:

1. A nucleic acid molecule not more than 90 nucleotides in length comprising an aptamer, wherein the aptamer is aptamer-1 (SEQ ID NO:2322), aptamer-35 (SEQ ID NO:2356), aptamer-41 (SEQ ID NO:2362) or aptamer-51 (SEQ ID NO:2372).

2. The nucleic acid molecule of claim 1, wherein the aptamer is aptamer-1 (SEQ ID NO:2322).

3. The nucleic acid molecule of claim 1, wherein the aptamer is aptamer-35 (SEQ ID NO:2356).

4. The nucleic acid molecule of claim 1, wherein the aptamer is aptamer-41 (SEQ ID NO:2362).

5. The nucleic acid molecule of claim 1, wherein the aptamer is aptamer-51 (SEQ ID NO:2372).

6. The nucleic acid molecule of claim 1, wherein the nucleotides are RNA.

7. The nucleic acid molecule of claim 6, wherein the RNA includes a modified nucleotide.

8. The nucleic acid molecule of claim 7, wherein the RNA is chemically modified (2'-fluoropyridines).

9. A conjugate comprising the nucleic acid molecule of claim 1 linked to a therapeutic or diagnostic molecule.

10. The conjugate of claim 9, wherein the therapeutic molecule is an RNAi molecule.

11. The conjugate of claim 10, wherein the RNAi molecule is an siRNA molecule or an miRNA molecule.

12. The conjugate of claim 11, wherein the siRNA specifically targets Nx1 NADPH oxidase.

13. A method for delivering a therapeutic or diagnostic molecule to a vascular smooth muscle cell, comprising contacting the cell with the conjugate of claim 9.

14. A pharmaceutical composition comprising a pharmaceutically acceptable carrier and
  (i) a nucleic acid molecule not more than 90 nucleotides in length comprising an aptamer, wherein the aptamer is aptamer-1 (SEQ ID NO:2322), aptamer-35 (SEQ ID NO:2356), aptamer-41 (SEQ ID NO:2362) or aptamer-51 (SEQ ID NO:2372); or
  (ii) a conjugate comprising a nucleic acid molecule not more than 90 nucleotides in length comprising an aptamer, wherein the aptamer is aptamer-1 (SEQ ID NO:2322), aptamer-35 (SEQ ID NO:2356), aptamer-41 (SEQ ID NO:2362) or aptamer-51 (SEQ ID NO:2372) operably linked to a therapeutic or diagnostic molecule.

15. An article of manufacture comprising a solid substrate coated with the molecule of claim 1.

16. The article of claim 15, wherein the solid substrate is a stent, catheter, a catheter hub, a catheter port, or a non-degradable implant.

* * * * *